(12) United States Patent
Tada et al.

(10) Patent No.: US 9,349,601 B2
(45) Date of Patent: May 24, 2016

(54) RUTHENIUM COMPLEX, METHOD FOR PRODUCING SAME, AND METHOD FOR PRODUCING RUTHENIUM-CONTAINING THIN FILM

(71) Applicants: TOSOH CORPORATION, Shunan-shi, Yamaguchi (JP); SAGAMI CHEMICAL RESEARCH INSTITUTE, Ayase-shi, Kanagawa (JP)

(72) Inventors: Kenichi Tada, Kanagawa (JP); Toshiki Yamamoto, Kanagawa (JP); Hiroyuki Oike, Kanagawa (JP); Atsushi Maniwa, Kanagawa (JP); Hirokazu Chiba, Kanagawa (JP); Kohei Iwanaga, Kanagawa (JP); Kazuhisa Kawano, Kanagawa (JP)

(73) Assignees: TOSOH CORPORATION, Shunan (JP); SAGAMI CHEMICAL RESEARCH INSTITUTE, Ayase (JP)

(*) Notice: Subject to any disclaimer, the term of this patent is extended or adjusted under 35 U.S.C. 154(b) by 0 days.

(21) Appl. No.: 14/650,274

(22) PCT Filed: Dec. 6, 2013

(86) PCT No.: PCT/JP2013/082889
§ 371 (c)(1),
(2) Date: Jun. 5, 2015

(87) PCT Pub. No.: WO2014/088108
PCT Pub. Date: Jun. 12, 2014

(65) Prior Publication Data
US 2015/0303063 A1    Oct. 22, 2015

(30) Foreign Application Priority Data

Dec. 7, 2012  (JP) ................................ 2012-268396
Jun. 26, 2013  (JP) ................................ 2013-133480
Jul. 29, 2013  (JP) ................................ 2013-156294

(51) Int. Cl.
*C07F 15/00*  (2006.01)
*H01L 21/285*  (2006.01)
*C23C 16/18*  (2006.01)
(Continued)

(52) U.S. Cl.
CPC ............ *H01L 21/28568* (2013.01); *C07F 7/02* (2013.01); *C07F 15/0046* (2013.01); *C23C 16/18* (2013.01); *H01L 21/28556* (2013.01);
(Continued)

(58) Field of Classification Search
CPC .................. H01L 21/28568; H01L 21/28562; H01L 21/28556; H01L 21/76871; H01L 21/76843; C01F 7/02; C07F 15/0046; C23C 16/18

USPC .................................. 556/136, 137; 438/681
See application file for complete search history.

(56) References Cited

U.S. PATENT DOCUMENTS

2003/0088116 A1  5/2003  Kawano et al.
2006/0083857 A1  4/2006  Meiere
(Continued)

FOREIGN PATENT DOCUMENTS

JP  2003-342286  12/2003
JP  2008-516956  5/2008
(Continued)

OTHER PUBLICATIONS

International Search Report for PCT/JP2013/082889, mailed Feb. 25, 2014, 4 pages (w/ trans).
(Continued)

*Primary Examiner* — Porfirio Nazario Gonzalez
(74) *Attorney, Agent, or Firm* — Nixon & Vanderhye P.C.

(57) ABSTRACT

The present invention is to provide a ruthenium complex represented by formula (1a), (2), (3), etc., which is useful for producing a ruthenium-containing thin film both under the conditions using an oxidizing gas as the reaction gas and under the conditions using a reducing gas as the reaction gas:

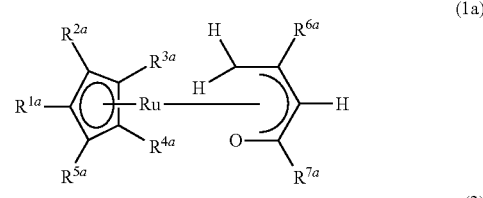

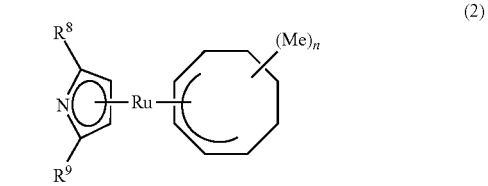

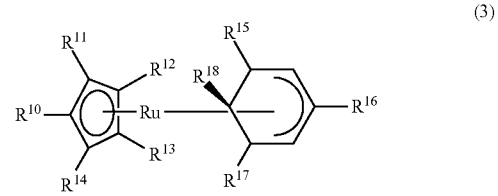

wherein $R^{1a}$ to $R^{7a}$, $R^8$, $R^9$ and $R^{10}$ to $R^{18}$ represents an alkyl group having a carbon number of 1 to 6, etc., and n represents an integer of 0 to 2.

29 Claims, 6 Drawing Sheets

(51) Int. Cl.
 *C07F 7/02* (2006.01)
 *H01L 21/768* (2006.01)
(52) U.S. Cl.
 CPC .... *H01L 21/28562* (2013.01); *H01L 21/76843* (2013.01); *H01L 21/76871* (2013.01)

(56) References Cited

U.S. PATENT DOCUMENTS

| | | |
|---|---|---|
| 2010/0028535 A1 | 2/2010 | Meiere |
| 2010/0034971 A1 | 2/2010 | Gatineau et al. |
| 2011/0206845 A1 | 8/2011 | Meiere |

FOREIGN PATENT DOCUMENTS

| | | |
|---|---|---|
| JP | 2009-046440 | 3/2009 |
| JP | 2010-513467 | 4/2010 |
| JP | 2011-106008 | 6/2011 |

OTHER PUBLICATIONS

Trakarnpruk, et al., "Half-Open Ruthenocenes Derived from [Ru(C$_5$Me$_5$)Cl]$_4$: Syntheses, Characterizations, and Solid-State Structures", *Oraganometallics* 1992, vol. 11, No. 4, pp. 1686-1692.

Clemente et al., "Syntheses, Structures, and Reactivity Studies of Half-Open Ruthenocenes and Their Oxodienyl Analogues", *Organometallics* 2002, vol. 21, No. 4, pp. 592-605.

Trost et al., "A Convenient Synthetic Route to [CpRu(CH$_3$CN)$_3$]PF$_6$", *Organometallics* 2002, vol. 21, No. 21, pp. 2544-2546.

Kündig, et al., Efficient Synthesis of Tris(acetonitrile)—($\eta^5$-cyclopentadienyl)—ruthenium (II) Hexafluorophosphate via Ruthenocene, *Advanced Synthesis & Catalysis*, 2004, vol. 346, pp. 901-904.

Duraczyńska et al., "Diphenylvinylphosphine (DPVP) complexes containing the ($\eta^5$—MeC$_5$H$_4$)Ru(II) moiety: synthesis, characterization and reactions", *The Royal Society of Chemistry* 2003, Dalton Transactions, 2003, pp. 449-457.

Schrenk et al., "Effect of Arene Methylation on Photochemical Arene Replacement Reactions of [($\eta^5$—C$_5$(CH$_3$)$_5$)M(n$^6$—arene)]$^+$ (M=Fe, Ru) Complexes", *Inorganic Chemistry* 1986, vol. 25, No. 19, pp. 3501-3504.

Ando et al., "Ru cyclooctatetraene precursors for MOCVD", *The Royal Society of Chemistry* 2012, Dalton Transactions, 2012, vol. 41, pp. 1678-1682.

McComas et al., "Neutral Ru($\eta^5$-pyrrole) Complexes. Synthesis and Structure of Diazaruthenocenes and Ru(1-3:5,6-$\eta^5$—C$_8$H$_{11}$) ($\eta^5$-pyrrole ) Complexes", *Organometallics* 2000, vol. 19, No. 15, pp. 2853-2857.

Older et al., "The Mechanism of Carbon—Carbon Bond Activation in Cationic 6-Alkylcyclohexadienyl Ruthenium Hydride Complexes", *Journal of the American Chemical Society*, 2000, vol. 122, No. 12, pp. 2784-2797.

RUTHENIUM COMPLEX, METHOD FOR PRODUCING SAME, AND METHOD FOR PRODUCING RUTHENIUM-CONTAINING THIN FILM

This application is the U.S. national phase of International Application No. PCT/JP2013/082889 filed 6 Dec. 2013 which designated the U.S. and claims priority to JP Patent Application No. 2012-268396 filed 7 Dec. 2012, JP Patent Application No. 2013-133480 filed 26 Jun. 2013 and JP Patent Application No. 2013-156294 filed 29 Jul. 2013, the entire contents of each of which are hereby incorporated by reference.

TECHNICAL FIELD

The present invention relates to a ruthenium complex useful as a raw material for the production of a semiconductor element, a production method thereof, and a method for producing a ruthenium-containing thin film using the ruthenium complex.

BACKGROUND ART

Ruthenium has features, e.g., exhibiting high electrical conductivity, permitting the formation of an electrically conductive oxide, having a high work function, and ensuring excellent etching characteristics and excellent lattice matching with copper and therefore, is attracting attention as a material for a memory electrode such as DRAM, a gate electrode, a copper-wiring seed layer/adhesion layer, etc. In the next-generation semiconductor device, a highly miniaturized and highly three-dimensional design is employed for the purpose of more enhancing the memory capacity or responsiveness. Accordingly, in order to use ruthenium as a material constituting the next-generation semiconductor device, it is required to establish a technique of uniformly forming a ruthenium-containing thin film with a thickness of approximately from a few nanometers to a few tens of nanometers on a three-dimensional substrate. As the technique for producing a metal thin film on a three-dimensional substrate, use of a vapor deposition method based on a chemical reaction, such as atomic layer deposition method (ALD method) and chemical vapor deposition method (CVD method), is believed promising. For example, in the case of depositing metallic ruthenium as a next-generation DRAM upper electrode by using this vapor deposition method, a metal oxide such as $ZrO_2$ is used as a capacitor insulating film for the underlying base and therefore, the deposition may be performed under the conditions using an oxidizing gas. In the case of using ruthenium as a next-generation DRAM lower electrode or a copper-wiring seed layer/adhesion layer, titanium nitride, tantalum nitride, etc. is expected to be employed as a barrier metal for the underlying base. When a barrier metal is oxidized at the time of production of a ruthenium-containing thin film, there arises a problem such as deterioration of the barrier performance, defective conduction to a transistor due to rise in the resistance value, and reduction in the responsiveness resulting from an increased interconnection capacity. For the purpose of avoiding such a problem, a material enabling the production of a ruthenium-containing thin film even under the conditions without using an oxidizing gas such as oxygen and ozone is demanded.

In Non-Patent Document 1 and Non-Patent Document 2, ($\eta^5$-2,4-dimethyl-1-oxa-2,4-pentadienyl)($\eta^5$-1,2,3,4,5-pentamethylcyclopentadienyl)ruthenium and ($\eta^5$-2,4-di-tert-butyl-1-oxa-2,4-pentadienyl)($\eta^5$-1,2,3,4,5-pentamethylcyclopentadienyl)ruthenium are described as a compound having a structure similar to that of the ruthenium complex (1a) of the present invention. However, the compounds described in those documents are limited to a complex having an $\eta^5$-1,2,3,4,5-pentamethylcyclopentadienyl ligand. In addition, the synthesis methods described in those documents are based on a reaction of chloro($\eta^5$-1,2,3,4,5-pentamethylcyclopentadienyl)ruthenium with lithium enolate or a reaction of chloro($\eta^5$-1,2,3,4,5-pentamethylcyclopentadienyl)ruthenium with an enone derivative and potassium carbonate and are different from the production method of the present invention. Furthermore, those documents are absolutely silent as to using such a complex as a material for the production of a ruthenium-containing thin film.

A cationic ruthenium complex [($\eta^5$-cyclopentadienyl)tris(nitrile)ruthenium]$^+$ is useful as a raw material for synthesis of various ruthenium complexes including the ruthenium complex of the present invention. Non-Patent Document 3 describes a method for producing [Ru($\eta^5$-C$_5$H$_5$)(MeCN)$_3$][PF$_6$] by irradiating [Ru($\eta^5$-C$_5$H$_5$)($\eta^6$-C$_6$H$_6$)][PF$_6$] with light in acetonitrile. In addition, Non-Patent Document 4 describes a method for producing [Ru($\eta^5$-C$_5$H$_5$)(MeCN)$_3$][PF$_6$] by reacting ruthenocene with aluminum chloride, aluminum, titanium chloride, naphthalene and potassium borofluoride to prepare an $\eta^6$-naphthalene complex and further reacting acetonitrile therewith.

However, the synthesis methods of a cationic tris(nitrile) complex described in Non-Patent Document 3 and Non-Patent Document 4 have a problem, for example, that equipment for intense ultraviolet irradiation is necessary or an expensive raw material or a large amount of a reactive agent is used, and these methods can hardly be a practical production method excellent in the cost benefit.

As a cationic tris(nitrile)ruthenium complex having a monosubstituted cyclopentadienyl ligand, [($\eta^5$-methylcyclopentadienyl)tris(acetonitrile)ruthenium]$^+$ is described in Non-Patent Document 5. In addition, as a cationic ruthenium complex having a pentasubstituted cyclopentadienyl ligand, [($\eta^5$-1,2,3,4,5-pentamethylcyclopentadienyl)tris(acetonitrile)ruthenium]$^+$ is described in Non-Patent Document 6. However, there is no report on a cationic tris(nitrile)ruthenium complex having a monosubstituted cyclopentadienyl ligand containing an alkyl group having a carbon number of 2 to 6.

In Non-Patent Document 7, tricarbonyl($\eta^4$-1,3,5,7-cyclooctatetraene)ruthenium (Ru($\eta^4$-C$_8$H$_8$)(CO)$_3$), tricarbonyl($\eta^4$-methyl-1,3,5,7-cyclooctatetraene)ruthenium (Ru($\eta^4$-C$_8$H$_7$Me)(CO)$_3$), and tricarbonyl($\eta^4$-ethyl-1,3,5,7-cyclooctatetraene)ruthenium (Ru($\eta^4$-C$_8$H$_7$Et)(CO)$_3$) are described as a compound capable of producing a metallic ruthenium thin film under the conditions using a reducing gas as the reaction gas. However, the metallic ruthenium thin films produced using these compounds have a high resistivity of 93, 152 and 125 µΩ·cm, respectively, and can be hardly a practical material.

In Non-Patent Document 8, (1-3:5-6-$\eta^5$-cyclooctadienyl)($\eta^5$-2,3,4,5-tetramethylpyrrolyl)ruthenium (Ru(1-3:5-6-$\eta^5$-C$_8$H$_{11}$)($\eta^5$-NC$_4$Me$_4$)) is described as a compound having a structure similar to that of the ruthenium complex (2) of the present invention. However, the compound described in this document is limited to a complex having a 1-3:5-6-$\eta^5$-cyclooctadienyl ligand. In addition, the synthesis method described in the document is based on a reaction of di-µ-chloro-($\eta^4$-1,5-cyclooctadiene)ruthenium ([Ru($\eta^4$-C$_8$H$_{12}$)Cl$_2$]$_x$) with 2,3,4,5-tetramethylpyrrolyl-lithium and is different from the production method of the present invention.

Furthermore, the document is absolutely silent as to using this complex as a material for the production of a ruthenium-containing thin film.

In Non-Patent Document 9, ($\eta^5$-6-exo-methylcyclohexadienyl)($\eta^5$-1,2,3,4,5-pentamethylcyclopentadienyl)ruthenium is described as a compound having a structure similar to that of the ruthenium complex (3) of the present invention, but the compound described in this document is limited to a complex having an $\eta^5$-1,2,3,4,5-pentamethylcyclopentadienyl ligand. Furthermore, the document is absolutely silent as to using this complex as a material for the production of a ruthenium-containing thin film.

BACKGROUND ART DOCUMENT

Non-Patent Document

Non-Patent Document 1: Organometallics, Vol. 11, page 1686 (1992)
Non-Patent Document 2: Organometallics, Vol. 21, page 592 (2002)
Non-Patent Document 3: Organometallics, Vol. 21, page 2544 (2002)
Non-Patent Document 4: Advanced Synthesis & Catalysis, Vol. 346, page 901 (2004)
Non-Patent Document 5: Dalton Transactions, page 449 (2003)
Non-Patent Document 6: Inorganic Chemistry, Vol. 25, page 3501 (1986)
Non-Patent Document 7: Dalton Transactions, Vol. 41, page 1678 (2012)
Non-Patent Document 8: Organometallics, Vol. 19, page 2853 (2000)
Non-Patent Document 9: Journal of the American Chemical Society, Vol. 122, page 2784 (2000)

SUMMARY OF INVENTION

Problem that Invention is to Solve

An object of the present invention is to provide a production method capable of producing a ruthenium-containing thin film both under the conditions using an oxidizing gas as the reaction gas and under the conditions using a reducing gas as the reaction gas, a ruthenium complex useful as a material for the production method, and a method for producing the ruthenium complex.

Means for Solving Problem

As a result of intensive studies to attain the above-described object, the present inventors have found that a specific ruthenium complex is useful as a material for producing a ruthenium-containing thin film both under the conditions using an oxidizing gas as the reaction gas and under the conditions using a reducing gas as the reaction gas. The present invention has been accomplished based on this finding.

That is, the present invention relates to a ruthenium complex represented by formula (A), more specifically, ruthenium complexes represented by formulae (1a), (2) and (3), a production method of the ruthenium complex, a method for producing a ruthenium-containing thin film using the ruthenium complex, and a semiconductor device using the ruthenium-containing thin film:

[Chem. 1]

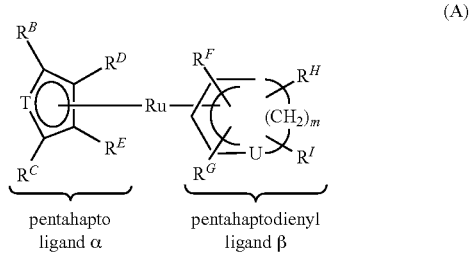

(A)

pentahapto ligand α    pentahaptodienyl ligand β

(wherein T represents $CR^A$ or a nitrogen atom; U represents an oxygen atom or CH; each of $R^A$, $R^B$, $R^C$, $R^D$, $R^E$, $R^F$, $R^G$, $R^H$ and $R^I$ independently represents a hydrogen atom or an alkyl group having a carbon number of 1 to 6; m represents any one integer of 0, 1 and 3; and the pentahaptodienyl ligand β has a cyclic structure when m is 1 or 3, and has a non-cyclic structure when m is 0, provided that when m is 0, T is $CR^A$, U is an oxygen atom, $R^F$ and $R^G$ are an alkyl group having a carbon number of 1 to 6, and $R^H$ and $R^I$ are a hydrogen atom, excluding a case where all of $R^A$, $R^B$, $R^C$, $R^D$ and $R^E$ are a methyl group at the same time, that when m is 1, T is $CR^A$, U is CH and $R^I$ is an alkyl group having a carbon number of 1 to 6, excluding a case where all of $R^F$, $R^G$ and $R^H$ are a hydrogen atom at the same time and all of $R^A$, $R^B$, $R^C$, $R^D$, $R^E$ and $R^I$ are a methyl group at the same time, and that when m is 3, T is a nitrogen atom, U is CH, $R^B$ and $R^C$ are an alkyl group having a carbon number of 1 to 6, $R^D$, $R^E$, $R^F$ and $R^G$ are a hydrogen atom, and $R^H$ and $R^I$ are a hydrogen atom or a methyl group):

[Chem. 2]

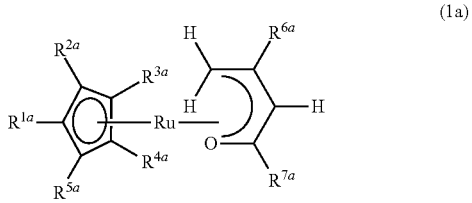

(1a)

(wherein each of $R^{1a}$, $R^{2a}$, $R^{3a}$, $R^{4a}$ and $R^{5a}$ independently represents a hydrogen atom or an alkyl group having a carbon number of 1 to 6, excluding a case where all of $R^{1a}$, $R^{2a}$, $R^{3a}$, $R^{4a}$ and $R^{5a}$ are a methyl group at the same time; and each of $R^{6a}$ and $R^{7a}$ independently represents an alkyl group having a carbon number of 1 to 6):

[Chem. 3]

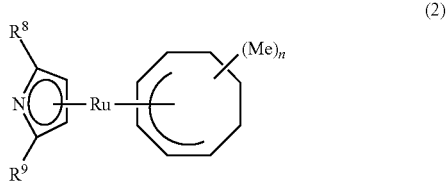

(2)

(wherein each of $R^8$ and $R^9$ independently represents an alkyl group having a carbon number of 1 to 6; and n represents an integer of 0 to 2):

[Chem. 4]

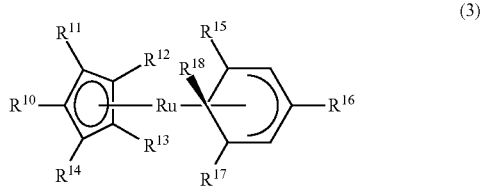

(3)

(wherein each of $R^{10}$, $R^{11}$, $R^{12}$, $R^{13}$, $R^{14}$, $R^{15}$, $R^{16}$ and $R^{17}$ independently represents a hydrogen atom or an alkyl group having a carbon number of 1 to 6; and $R^{18}$ represents an alkyl group having a carbon number of 1 to 6, excluding a case where all of $R^{15}$, $R^{16}$ and $R^{17}$ are a hydrogen atom at the same time and all of $R^{10}$, $R^{11}$, $R^{12}$, $R^{13}$, $R^{14}$ and $R^{18}$ are a methyl group at the same time).

Another aspect of the present invention relates to a method for producing a ruthenium complex, involving reacting a cationic tris(nitrile) complex represented by formula (4):

[Chem. 5]

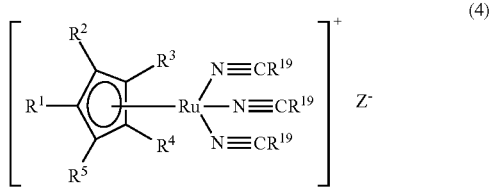

(4)

(wherein each of $R^1$, $R^2$, $R^3$, $R^4$ and $R^5$ independently represents a hydrogen atom or an alkyl group having a carbon number of 1 to 6; $R^{19}$ represents an alkyl group having a carbon number of 1 to 4; and $Z^-$ represents a counter anion) with an enone derivative represented by formula (5):

[Chem. 6]

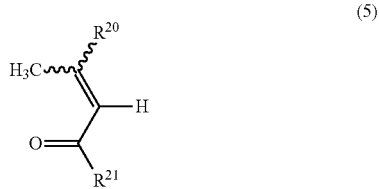

(5)

(wherein each of $R^{20}$ and $R^{21}$ independently represents an alkyl group having a carbon number of 1 to 6) in the presence of a base to produce a ruthenium complex represented by formula (1):

[Chem. 7]

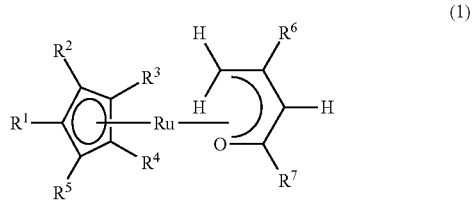

(1)

(wherein each of $R^1$, $R^2$, $R^3$, $R^4$ and $R^5$ independently represents a hydrogen atom or an alkyl group having a carbon number of 1 to 6; and each of $R^6$ and $R^7$ independently represents an alkyl group having a carbon number of 1 to 6).

Effects of Invention

By virtue of using a novel ruthenium complex represented by formula (A) of the present invention, more specifically, a ruthenium complex represented by each of formulae (1a), (2) and (3) or a ruthenium complex represented by each of formulae (1) and (3a) as a material, a ruthenium-containing thin film can be produced both under the conditions using an oxidizing gas and under the conditions using a reducing gas.

MODE FOR CARRYING OUT INVENTION

Figure 1:
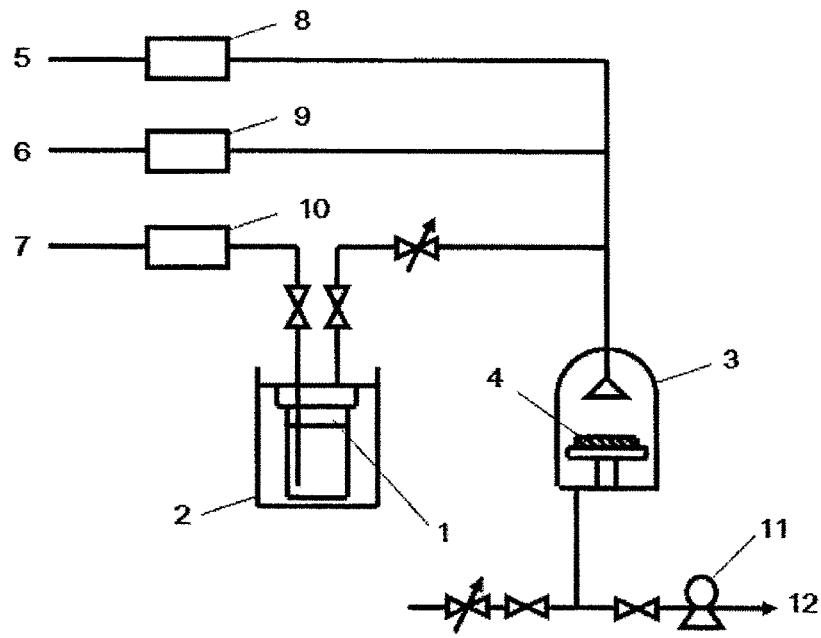
FIG. 1 is a view showing a CVD apparatus used in Examples 14 to 37, 40 to 45 and 55 to 65, Evaluation Examples 1 and 2 and Comparative Examples 1 to 10.

The present invention is described in more detail below.

The ruthenium complex of the present invention is a ruthenium complex represented by formula (A), and among others, ruthenium complexes represented by formulae (1a), (2) and (3) are preferred.

The ruthenium complex represented by formula (1a) corresponds to a subordinate concept of the ruthenium complex represented by formula (1). The ruthenium complex represented by formula (1a) does not encompass a case where all of $R^{1a}$, $R^{2a}$, $R^{3a}$, $R^{4a}$ and $R^{5a}$ are a methyl group at the same time. On the other hand, the ruthenium complex represented by formula (1) encompasses a case where all of $R^1$, $R^2$, $R^3$, $R^4$ and $R^5$ are a methyl group at the same time.

Definitions of $R^{1a}$, $R^{2a}$, $R^{3a}$, $R^{4a}$, $R^{5a}$, $R^{6a}$ and $R^{7a}$ in formula (1a) are described below. The alkyl group having a carbon number of 1 to 6 represented by $R^{1a}$, $R^{2a}$, $R^{3a}$, $R^{4a}$ and $R^{5a}$ may be any of a linear alkyl group, a branched alkyl group and a cyclic alkyl group, and specific examples thereof include a methyl group, an ethyl group, a propyl group, an isopropyl group, a cyclopropyl group, a butyl group, an isobutyl group, a sec-butyl group, a tert-butyl group, a cyclobutyl group, a pentyl group, a 1-methylbutyl group, a 2-methylbutyl group, an isopentyl group, a neopentyl group, a tert-pentyl group, a cyclopentyl group, a cyclobutylmethyl group, a hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a cyclohexyl group, a cyclopentylmethyl group, a 1-cyclobutylethyl group, and a 2-cyclobutylethyl group. From the standpoint that the ruthenium complex (1a) of the present invention has vapor pressure and thermal stability suitable as a CVD material or an ALD material, preferably, $R^{1a}$ is an alkyl group having a carbon number of 1 to 6 and $R^{2a}$, $R^{3a}$, $R^{4a}$ and $R^{5a}$ are a hydrogen atom; and more preferably, $R^{1a}$ is a methyl group or an ethyl group and $R^{2a}$, $R^{3a}$, $R^{4a}$ and $R^{5a}$ are a hydrogen atom.

The alkyl group having a carbon number of 1 to 6 represented by $R^{6a}$ and $R^{7a}$ may be any of a linear alkyl group, a branched alkyl group and a cyclic alkyl group, and specific examples thereof include a methyl group, an ethyl group, a propyl group, an isopropyl group, a cyclopropyl group, a butyl group, an isobutyl group, a sec-butyl group, a tert-butyl group, a cyclobutyl group, a pentyl group, a 1-methylbutyl group, a 2-methylbutyl group, an isopentyl group, a neopentyl group, a tert-pentyl group, a cyclopentyl group, a cyclobutylmethyl group, a hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a cyclohexyl group, a cyclopentylmethyl group, a 1-cyclobutylethyl group, and a 2-cyclobutylethyl group. From the standpoint that the ruthenium complex (1a) of the present invention has vapor pressure and thermal stability suitable as a CVD material or an ALD material, $R^{6a}$ and $R^{7a}$ are preferably a methyl group.

Specific examples of the ruthenium complex (1a) of the present invention are shown in Tables 1-1 to 1-6. Here, Me, Et, Pr, $^i$Pr, Bu, $^i$Bu, $^s$Bu, $^t$Bu, Pe, $^c$Pe and Hx stand for a methyl group, an ethyl group, a propyl group, an isopropyl group, a butyl group, an isobutyl group, a sec-butyl group, a tert-butyl group, a pentyl group, a cyclopentyl group and a hexyl group, respectively.

[Table 1]

TABLE 1-1

| (1a) Compound No. | $R^{1a}$ | $R^{2a}$ | $R^{3a}$ | $R^{4a}$ | $R^{5a}$ | $R^{6a}$ | $R^{7a}$ |
|---|---|---|---|---|---|---|---|
| 1a-1 | H | H | H | H | H | Me | Me |
| 1a-2 | Me | H | H | H | H | Me | Me |
| 1a-3 | Et | H | H | H | H | Me | Me |
| 1a-4 | Pr | H | H | H | H | Me | Me |
| 1a-5 | $^i$Pr | H | H | H | H | Me | Me |
| 1a-6 | Bu | H | H | H | H | Me | Me |
| 1a-7 | $^i$Bu | H | H | H | H | Me | Me |
| 1a-8 | $^s$Bu | H | H | H | H | Me | Me |
| 1a-9 | $^t$Bu | H | H | H | H | Me | Me |
| 1a-10 | Pe | H | H | H | H | Me | Me |
| 1a-11 | $^c$Pe | H | H | H | H | Me | Me |
| 1a-12 | Hx | H | H | H | H | Me | Me |
| 1a-13 | Me | Me | H | H | H | Me | Me |
| 1a-14 | Me | H | Me | H | H | Me | Me |
| 1a-15 | $^t$Bu | H | $^t$Bu | H | H | Me | Me |
| 1a-16 | Me | Me | Me | H | H | Me | Me |
| 1a-17 | Me | Me | H | Me | H | Me | Me |
| 1a-18 | $^i$Pr | $^i$Pr | H | $^i$Pr | H | Me | Me |
| 1a-19 | Me | Me | Me | Me | H | Me | Me |
| 1a-20 | Et | Me | Me | Me | Me | Me | Me |
| 1a-21 | Pr | Me | Me | Me | Me | Me | Me |
| 1a-22 | H | H | H | H | H | Me | Et |
| 1a-23 | Me | H | H | H | H | Me | Et |
| 1a-24 | Et | H | H | H | H | Me | Et |
| 1a-25 | Pr | H | H | H | H | Me | Et |
| 1a-26 | $^i$Pr | H | H | H | H | Me | Et |
| 1a-27 | Bu | H | H | H | H | Me | Et |
| 1a-28 | $^i$Bu | H | H | H | H | Me | Et |

TABLE 1-1-continued

| (1a) Compound No. | $R^{1a}$ | $R^{2a}$ | $R^{3a}$ | $R^{4a}$ | $R^{5a}$ | $R^{6a}$ | $R^{7a}$ |
|---|---|---|---|---|---|---|---|
| 1a-29 | $^s$Bu | H | H | H | H | Me | Et |
| 1a-30 | $^t$Bu | H | H | H | H | Me | Et |
| 1a-31 | Pe | H | H | H | H | Me | Et |
| 1a-32 | $^c$Pe | H | H | H | H | Me | Et |
| 1a-33 | Hx | H | H | H | H | Me | Et |
| 1a-34 | Me | Me | H | H | H | Me | Et |
| 1a-35 | Me | H | Me | H | H | Me | Et |
| 1a-36 | $^t$Bu | H | $^t$Bu | H | H | Me | Et |
| 1a-37 | Me | Me | Me | H | H | Me | Et |
| 1a-38 | Me | Me | H | Me | H | Me | Et |

[Table 2]

TABLE 1-2

| (1a) Compound No. | $R^{1a}$ | $R^{2a}$ | $R^{3a}$ | $R^{4a}$ | $R^{5a}$ | $R^{6a}$ | $R^{7a}$ |
|---|---|---|---|---|---|---|---|
| 1a-39 | $^i$Pr | H | $^i$Pr | H | $^i$Pr | Me | Et |
| 1a-40 | Me | Me | Me | Me | H | Me | Et |
| 1a-41 | Et | Me | Me | Me | Me | Me | Et |
| 1a-42 | Pr | Me | Me | Me | Me | Me | Et |
| 1a-43 | H | H | H | H | H | Et | Me |
| 1a-44 | Me | H | H | H | H | Et | Me |
| 1a-45 | Et | H | H | H | H | Et | Me |
| 1a-46 | Pr | H | H | H | H | Et | Me |
| 1a-47 | $^i$Pr | H | H | H | H | Et | Me |
| 1a-48 | Bu | H | H | H | H | Et | Me |
| 1a-49 | $^i$Bu | H | H | H | H | Et | Me |
| 1a-50 | $^s$Bu | H | H | H | H | Et | Me |
| 1a-51 | $^t$Bu | H | H | H | H | Et | Me |
| 1a-52 | Pe | H | H | H | H | Et | Me |
| 1a-53 | $^c$Pe | H | H | H | H | Et | Me |
| 1a-54 | Hx | H | H | H | H | Et | Me |
| 1a-55 | Me | Me | H | H | H | Et | Me |
| 1a-56 | Me | H | Me | H | H | Et | Me |
| 1a-57 | $^t$Bu | H | $^t$Bu | H | H | Et | Me |
| 1a-58 | Me | Me | Me | H | H | Et | Me |
| 1a-59 | Me | Me | H | Me | H | Et | Me |
| 1a-60 | $^i$Pr | H | $^i$Pr | H | $^i$Pr | Et | Me |
| 1a-61 | Me | Me | Me | Me | H | Et | Me |
| 1a-62 | Et | Me | Me | Me | Me | Et | Me |
| 1a-63 | Pr | Me | Me | Me | Me | Et | Me |
| 1a-64 | H | H | H | H | H | Me | $^i$Pr |
| 1a-65 | Me | H | H | H | H | Me | $^i$Pr |
| 1a-66 | Et | H | H | H | H | Me | $^i$Pr |
| 1a-67 | Pr | H | H | H | H | Me | $^i$Pr |
| 1a-68 | $^i$Pr | H | H | H | H | Me | $^i$Pr |
| 1a-69 | Bu | H | H | H | H | Me | $^i$Pr |
| 1a-70 | $^i$Bu | H | H | H | H | Me | $^i$Pr |
| 1a-71 | $^s$Bu | H | H | H | H | Me | $^i$Pr |
| 1a-72 | $^t$Bu | H | H | H | H | Me | $^i$Pr |
| 1a-73 | Pe | H | H | H | H | Me | $^i$Pr |
| 1a-74 | $^c$Pe | H | H | H | H | Me | $^i$Pr |
| 1a-75 | Hx | H | H | H | H | Me | $^i$Pr |
| 1a-76 | Me | Me | H | H | H | Me | $^i$Pr |

[Table 3]

TABLE 1-3

| (1a) Compound No. | $R^{1a}$ | $R^{2a}$ | $R^{3a}$ | $R^{4a}$ | $R^{5a}$ | $R^{6a}$ | $R^{7a}$ |
|---|---|---|---|---|---|---|---|
| 1a-77 | Me | H | Me | H | H | Me | $^i$Pr |
| 1a-78 | $^t$Bu | H | $^t$Bu | H | H | Me | $^i$Pr |
| 1a-79 | Me | Me | Me | H | H | Me | $^i$Pr |
| 1a-80 | Me | Me | H | Me | H | Me | $^i$Pr |
| 1a-81 | $^i$Pr | H | $^i$Pr | H | $^i$Pr | Me | $^i$Pr |
| 1a-82 | Me | Me | Me | Me | H | Me | $^i$Pr |
| 1a-83 | Et | Me | Me | Me | Me | Me | $^i$Pr |

TABLE 1-3-continued

| (1a) Compound No. | $R^{1a}$ | $R^{2a}$ | $R^{3a}$ | $R^{4a}$ | $R^{5a}$ | $R^{6a}$ | $R^{7a}$ |
|---|---|---|---|---|---|---|---|
| 1a-84 | Pr | Me | Me | Me | Me | Me | $^i$Pr |
| 1a-85 | H | H | H | H | H | $^i$Pr | Me |
| 1a-86 | Me | H | H | H | H | $^i$Pr | Me |
| 1a-87 | Et | H | H | H | H | $^i$Pr | Me |
| 1a-88 | Pr | H | H | H | H | $^i$Pr | Me |
| 1a-89 | $^i$Pr | H | H | H | H | $^i$Pr | Me |
| 1a-90 | Bu | H | H | H | H | $^i$Pr | Me |
| 1a-91 | $^i$Bu | H | H | H | H | $^i$Pr | Me |
| 1a-92 | $^s$Bu | H | H | H | H | $^i$Pr | Me |
| 1a-93 | $^t$Bu | H | H | H | H | $^i$Pr | Me |
| 1a-94 | Pe | H | H | H | H | $^i$Pr | Me |
| 1a-95 | $^c$Pe | H | H | H | H | $^i$Pr | Me |
| 1a-96 | Hx | H | H | H | H | $^i$Pr | Me |
| 1a-97 | Me | Me | H | H | H | $^i$Pr | Me |
| 1a-98 | Me | H | Me | H | H | $^i$Pr | Me |
| 1a-99 | $^t$Bu | H | $^t$Bu | H | H | $^i$Pr | Me |
| 1a-100 | Me | Me | Me | H | H | $^i$Pr | Me |
| 1a-101 | Me | Me | H | Me | H | $^i$Pr | Me |
| 1a-102 | $^i$Pr | H | $^i$Pr | H | $^i$Pr | $^i$Pr | Me |
| 1a-103 | Me | Me | Me | Me | H | $^i$Pr | Me |
| 1a-104 | Et | Me | Me | Me | Me | $^i$Pr | Me |
| 1a-105 | Pr | Me | Me | Me | Me | $^i$Pr | Me |
| 1a-106 | H | H | H | H | H | Me | $^t$Bu |
| 1a-107 | Me | H | H | H | H | Me | $^t$Bu |
| 1a-108 | Et | H | H | H | H | Me | $^t$Bu |
| 1a-109 | Pr | H | H | H | H | Me | $^t$Bu |
| 1a-110 | $^i$Pr | H | H | H | H | Me | $^t$Bu |
| 1a-111 | Bu | H | H | H | H | Me | $^t$Bu |
| 1a-112 | $^i$Bu | H | H | H | H | Me | $^t$Bu |
| 1a-113 | $^s$Bu | H | H | H | H | Me | $^t$Bu |
| 1a-114 | $^t$Bu | H | H | H | H | Me | $^t$Bu |

[Table 4]

TABLE 1-4

| (1a) Compound No. | $R^{1a}$ | $R^{2a}$ | $R^{3a}$ | $R^{4a}$ | $R^{5a}$ | $R^{6a}$ | $R^{7a}$ |
|---|---|---|---|---|---|---|---|
| 1a-115 | Pe | H | H | H | H | Me | $^t$Bu |
| 1a-116 | $^c$Pe | H | H | H | H | Me | $^t$Bu |
| 1a-117 | Hx | H | H | H | H | Me | $^t$Bu |
| 1a-118 | Me | Me | H | H | H | Me | $^t$Bu |
| 1a-119 | Me | H | Me | H | H | Me | $^t$Bu |
| 1a-120 | $^t$Bu | H | $^t$Bu | H | H | Me | $^t$Bu |
| 1a-121 | Me | Me | Me | H | H | Me | $^t$Bu |
| 1a-122 | Me | Me | H | Me | H | Me | $^t$Bu |
| 1a-123 | $^i$Pr | H | $^i$Pr | H | $^i$Pr | Me | $^t$Bu |
| 1a-124 | Me | Me | Me | Me | H | Me | $^t$Bu |
| 1a-125 | Et | Me | Me | Me | Me | Me | $^t$Bu |
| 1a-126 | Pr | Me | Me | Me | Me | Me | $^t$Bu |
| 1a-127 | H | H | H | H | H | $^t$Bu | Me |
| 1a-128 | Me | H | H | H | H | $^t$Bu | Me |
| 1a-129 | Et | H | H | H | H | $^t$Bu | Me |
| 1a-130 | Pr | H | H | H | H | $^t$Bu | Me |
| 1a-131 | $^i$Pr | H | H | H | H | $^t$Bu | Me |
| 1a-132 | Bu | H | H | H | H | $^t$Bu | Me |
| 1a-133 | $^i$Bu | H | H | H | H | $^t$Bu | Me |
| 1a-134 | $^s$Bu | H | H | H | H | $^t$Bu | Me |
| 1a-135 | $^t$Bu | H | H | H | H | $^t$Bu | Me |
| 1a-136 | Pe | H | H | H | H | $^t$Bu | Me |
| 1a-137 | $^c$Pe | H | H | H | H | $^t$Bu | Me |
| 1a-138 | Hx | H | H | H | H | $^t$Bu | Me |
| 1a-139 | Me | Me | H | H | H | $^t$Bu | Me |
| 1a-140 | Me | H | Me | H | H | $^t$Bu | Me |
| 1a-141 | $^t$Bu | H | $^t$Bu | H | H | $^t$Bu | Me |
| 1a-142 | Me | Me | Me | H | H | $^t$Bu | Me |
| 1a-143 | Me | Me | H | Me | H | $^t$Bu | Me |
| 1a-144 | $^i$Pr | H | $^i$Pr | H | $^i$Pr | $^t$Bu | Me |
| 1a-145 | Me | Me | Me | Me | H | $^t$Bu | Me |
| 1a-146 | Et | Me | Me | Me | Me | $^t$Bu | Me |
| 1a-147 | Pr | Me | Me | Me | Me | $^t$Bu | Me |
| 1a-148 | H | H | H | H | H | Et | Et |
| 1a-149 | Me | H | H | H | H | Et | Et |
| 1a-150 | Et | H | H | H | H | Et | Et |
| 1a-151 | Pr | H | H | H | H | Et | Et |
| 1a-152 | $^i$Pr | H | H | H | H | Et | Et |

[Table 5]

TABLE 1-5

| (1a) Compound No. | $R^{1a}$ | $R^{2a}$ | $R^{3a}$ | $R^{4a}$ | $R^{5a}$ | $R^{6a}$ | $R^{7a}$ |
|---|---|---|---|---|---|---|---|
| 1a-153 | Bu | H | H | H | H | Et | Et |
| 1a-154 | $^i$Bu | H | H | H | H | Et | Et |
| 1a-155 | $^s$Bu | H | H | H | H | Et | Et |
| 1a-156 | $^t$Bu | H | H | H | H | Et | Et |
| 1a-157 | Pe | H | H | H | H | Et | Et |
| 1a-158 | $^c$Pe | H | H | H | H | Et | Et |
| 1a-159 | Hx | H | H | H | H | Et | Et |
| 1a-160 | Me | Me | H | H | H | Et | Et |
| 1a-161 | Me | H | Me | H | H | Et | Et |
| 1a-162 | $^t$Bu | H | $^t$Bu | H | H | Et | Et |
| 1a-163 | Me | Me | Me | H | H | Et | Et |
| 1a-164 | Me | Me | H | Me | H | Et | Et |
| 1a-165 | $^i$Pr | H | $^i$Pr | H | $^i$Pr | Et | Et |
| 1a-166 | Me | Me | Me | Me | H | Et | Et |
| 1a-167 | Et | Me | Me | Me | Me | Et | Et |
| 1a-168 | Pr | Me | Me | Me | Me | Et | Et |
| 1a-169 | H | H | H | H | H | $^i$Pr | $^i$Pr |
| 1a-170 | Me | H | H | H | H | $^i$Pr | $^i$Pr |
| 1a-171 | Et | H | H | H | H | $^i$Pr | $^i$Pr |
| 1a-172 | Pr | H | H | H | H | $^i$Pr | $^i$Pr |
| 1a-173 | $^i$Pr | H | H | H | H | $^i$Pr | $^i$Pr |
| 1a-174 | Bu | H | H | H | H | $^i$Pr | $^i$Pr |
| 1a-175 | $^i$Bu | H | H | H | H | $^i$Pr | $^i$Pr |
| 1a-176 | $^s$Bu | H | H | H | H | $^i$Pr | $^i$Pr |
| 1a-177 | $^t$Bu | H | H | H | H | $^i$Pr | $^i$Pr |
| 1a-178 | Pe | H | H | H | H | $^i$Pr | $^i$Pr |
| 1a-179 | $^c$Pe | H | H | H | H | $^i$Pr | $^i$Pr |
| 1a-180 | Hx | H | H | H | H | $^i$Pr | $^i$Pr |
| 1a-181 | Me | Me | H | H | H | $^i$Pr | $^i$Pr |
| 1a-182 | Me | H | Me | H | H | $^i$Pr | $^i$Pr |
| 1a-183 | $^t$Bu | H | $^t$Bu | H | H | $^i$Pr | $^i$Pr |
| 1a-184 | Me | Me | Me | H | H | $^i$Pr | $^i$Pr |
| 1a-185 | Me | Me | H | Me | H | $^i$Pr | $^i$Pr |
| 1a-186 | $^i$Pr | H | $^i$Pr | H | $^i$Pr | $^i$Pr | $^i$Pr |
| 1a-187 | Me | Me | Me | Me | H | $^i$Pr | $^i$Pr |
| 1a-188 | Et | Me | Me | Me | Me | $^i$Pr | $^i$Pr |
| 1a-189 | Pr | Me | Me | Me | Me | $^i$Pr | $^i$Pr |
| 1a-190 | H | H | H | H | H | $^t$Bu | $^t$Bu |

[Table 6]

TABLE 1-6

| (1a) Compound No. | $R^{1a}$ | $R^{2a}$ | $R^{3a}$ | $R^{4a}$ | $R^{5a}$ | $R^{6a}$ | $R^{7a}$ |
|---|---|---|---|---|---|---|---|
| 1a-191 | Me | H | H | H | H | $^t$Bu | $^t$Bu |
| 1a-192 | Et | H | H | H | H | $^t$Bu | $^t$Bu |
| 1a-193 | Pr | H | H | H | H | $^t$Bu | $^t$Bu |
| 1a-194 | $^i$Pr | H | H | H | H | $^t$Bu | $^t$Bu |
| 1a-195 | Bu | H | H | H | H | $^t$Bu | $^t$Bu |
| 1a-196 | $^i$Bu | H | H | H | H | $^t$Bu | $^t$Bu |
| 1a-197 | $^s$Bu | H | H | H | H | $^t$Bu | $^t$Bu |
| 1a-198 | $^t$Bu | H | H | H | H | $^t$Bu | $^t$Bu |
| 1a-199 | Pe | H | H | H | H | $^t$Bu | $^t$Bu |
| 1a-200 | $^c$Pe | H | H | H | H | $^t$Bu | $^t$Bu |
| 1a-201 | Hx | H | H | H | H | $^t$Bu | $^t$Bu |
| 1a-202 | Me | Me | H | H | H | $^t$Bu | $^t$Bu |
| 1a-203 | Me | H | Me | H | H | $^t$Bu | $^t$Bu |

TABLE 1-6-continued

| (1a) Compound No. | $R^{1a}$ | $R^{2a}$ | $R^{3a}$ | $R^{4a}$ | $R^{5a}$ | $R^{6a}$ | $R^{7a}$ |
|---|---|---|---|---|---|---|---|
| 1a-204 | $^t$Bu | H | $^t$Bu | H | H | $^t$Bu | $^t$Bu |
| 1a-205 | Me | Me | Me | H | H | $^t$Bu | $^t$Bu |
| 1a-206 | Me | Me | H | Me | H | $^t$Bu | $^t$Bu |
| 1a-207 | $^i$Pr | H | $^i$Pr | H | $^i$Pr | $^t$Bu | $^t$Bu |
| 1a-208 | Me | Me | Me | Me | H | $^t$Bu | $^t$Bu |
| 1a-209 | Et | Me | Me | Me | Me | $^t$Bu | $^t$Bu |
| 1a-210 | Pr | Me | Me | Me | Me | $^t$Bu | $^t$Bu |

Among those exemplified in Tables 1-1 to 1-6, ($\eta^5$-cyclopentadienyl)($\eta^5$-2,4-dimethyl-1-oxa-2,4-pentadienyl)ruthenium (1a-1), ($\eta^5$-2,4-dimethyl-1-oxa-2,4-pentadienyl)($\eta^5$-methylcyclopentadienyl)ruthenium (1a-2), ($\eta^5$-2,4-dimethyl-1-oxa-2,4-pentadienyl)($\eta^5$-ethylcyclopentadienyl)ruthenium (1a-3), ($\eta^5$-2,4-dimethyl-1-oxa-2,4-pentadienyl)($\eta^5$-propylcyclopentadienyl)ruthenium (1a-4), ($\eta^5$-2,4-dimethyl-1-oxa-2,4-pentadienyl)($\eta^5$-isopropylcyclopentadienyl)ruthenium (1a-5), ($\eta^5$-2,4-dimethyl-1-oxa-2,4-pentadienyl)($\eta^5$-butylcyclopentadienyl)ruthenium (1a-6), ($\eta^5$-2,4-dimethyl-1-oxa-2,4-pentadienyl)($\eta^5$-isobutylcyclopentadienyl)ruthenium (1a-7), ($\eta^5$-2,4-dimethyl-1-oxa-2,4-pentadienyl)($\eta^5$-(sec-butyl)cyclopentadienyl)ruthenium (1a-8), ($\eta^5$-2,4-dimethyl-1-oxa-2,4-pentadienyl)($\eta^5$-(tert-butyl)cyclopentadienyl)ruthenium (1a-9), ($\eta^5$-2,4-dimethyl-1-oxa-2,4-pentadienyl)($\eta^5$-pentyl-cyclopentadienyl)ruthenium (1a-10), ($\eta^5$-(cyclopentyl)cyclopentadienyl)($\eta^5$-2,4-dimethyl-1-oxa-2,4-pentadienyl)ruthenium (1a-11) and ($\eta^5$-2,4-dimethyl-1-oxa-2,4-pentadienyl)($\eta^5$-hexylcyclopentadienyl)ruthenium (1a-12) are preferred, and 1a-2 and 1a-3 are more preferred.

The production method of the ruthenium complex (1a) of the present invention is described below. The ruthenium complex (1a) can be produced according to the following production method 1 of a ruthenium complex (1). Production method 1 is a method of reacting a cationic tris(nitrile) complex (4) with an enone derivative (5) in the presence of a base to produce a ruthenium complex (1).

[Chem. 8]

Production Method 1:

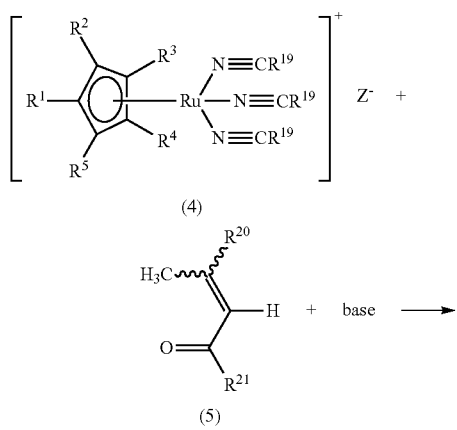

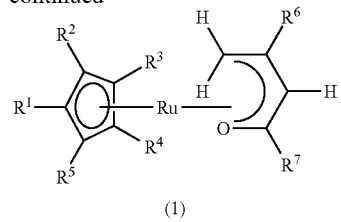

(wherein $R^1$, $R^2$, $R^3$, $R^4$, $R^5$, $R^6$, $R^7$, $R^{19}$, $R^{20}$, $R^{21}$ and $Z^-$ have the same meanings as above.)

Definitions of $R^1$, $R^2$, $R^3$, $R^4$, $R^5$, $R^6$ and $R^7$ in formula (1) are described below. The alkyl group having a carbon number of 1 to 6 represented by $R^1$, $R^2$, $R^3$, $R^4$ and $R^5$ may be any of a linear alkyl group, a branched alkyl group and a cyclic alkyl group, and specific examples thereof include a methyl group, an ethyl group, a propyl group, an isopropyl group, a cyclopropyl group, a butyl group, an isobutyl group, a sec-butyl group, a tert-butyl group, a cyclobutyl group, a pentyl group, a 1-methylbutyl group, a 2-methylbutyl group, an isopentyl group, a neopentyl group, a tert-pentyl group, a cyclopentyl group, a cyclobutylmethyl group, a hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a cyclohexyl group, a cyclopentylmethyl group, a 1-cyclobutylethyl group, and a 2-cyclobutylethyl group. In view of a high yield, preferably, $R^1$ is an alkyl group having a carbon number of 1 to 6 and $R^2$, $R^3$, $R^4$ and $R^5$ are a hydrogen atom; and more preferably, $R^1$ is a methyl group or an ethyl group and $R^2$, $R^3$, $R^4$ and $R^5$ are a hydrogen atom.

The alkyl group having a carbon number of 1 to 6 represented by $R^6$ and $R^7$ may be any of a linear alkyl group, a branched alkyl group and a cyclic alkyl group, and specific examples thereof include a methyl group, an ethyl group, a propyl group, an isopropyl group, a cyclopropyl group, a butyl group, an isobutyl group, a sec-butyl group, a tert-butyl group, a cyclobutyl group, a pentyl group, a 1-methylbutyl group, a 2-methylbutyl group, an isopentyl group, a neopentyl group, a tert-pentyl group, a cyclopentyl group, a cyclobutylmethyl group, a hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a cyclohexyl group, a cyclopentylmethyl group, a 1-cyclobutylethyl group, and a 2-cyclobutylethyl group. In view of a high yield, $R^6$ and $R^7$ are preferably a methyl group.

Specific examples of the ruthenium complex (1) include the compounds shown in Table 2, in addition to 1a-1 to 1a-210 shown in Tables 1-1 to 1-6.

[Table 7]

TABLE 2

| (1) Compound No. | $R^1$ | $R^2$ | $R^3$ | $R^4$ | $R^5$ | $R^6$ | $R^7$ |
|---|---|---|---|---|---|---|---|
| 1-211 | Me | Me | Me | Me | Me | Me | Me |
| 1-212 | Me | Me | Me | Me | Me | Me | Et |
| 1-213 | Me | Me | Me | Me | Me | Et | Me |
| 1-214 | Me | Me | Me | Me | Me | Me | $^i$Pr |
| 1-215 | Me | Me | Me | Me | Me | $^i$Pr | Me |
| 1-216 | Me | Me | Me | Me | Me | Me | $^t$Bu |

TABLE 2-continued

| (1) Compound No. | R¹ | R² | R³ | R⁴ | R⁵ | R⁶ | R⁷ |
|---|---|---|---|---|---|---|---|
| 1-217 | Me | Me | Me | Me | Me | $^t$Bu | Me |
| 1-218 | Me | Me | Me | Me | Me | Et | Et |
| 1-219 | Me | Me | Me | Me | Me | $^i$Pr | $^i$Pr |
| 1-220 | Me | Me | Me | Me | Me | $^t$Bu | $^t$Bu |

Among those exemplified in Tables 1-1 to 1-6 and Table 2, 1a-1, 1a-2, 1a-3, 1a-4, 1a-5, 1a-6, 1a-7, 1a-8, 1a-9, 1a-10, 1a-11 and 1a-12 are preferred by virtue of having vapor pressure and heat stability suitable as a CVD material or an ALD material, and 1a-2 and 1a-3 are more preferred.

The alkyl group having a carbon number of 1 to 4 represented by $R^{19}$ in the cationic tris(nitrile) complex (4) may be any of a linear alkyl group, a branched alkyl group and a cyclic alkyl group, and specific examples thereof include a methyl group, an ethyl group, a propyl group, an isopropyl group, a cyclopropyl group, a butyl group, an isobutyl group, a sec-butyl group, a tert-butyl group, and a cyclobutyl group. In view of a high yield of the ruthenium complex (1), $R^{19}$ is preferably a methyl group.

Specific examples of the cation moiety of the cationic tris(nitrile) complex (4) include [tris(acetonitrile)($\eta^5$-cyclopentadienyl)ruthenium(II)] ([Ru($\eta^5$-C$_5$H$_5$)(MeCN)$_3$]), [tris(acetonitrile)($\eta^5$-methylcyclopentadienyl)ruthenium(II)] ([Ru($\eta^5$-C$_5$MeH$_4$)(MeCN)$_3$]), [tris(acetonitrile)($\eta^5$-ethylcyclopentadienyl)ruthenium(II)] ([Ru($\eta^5$-C$_5$EtH$_4$)(MeCN)$_3$]), [tris(acetonitrile)($\eta^5$-propylcyclopentadienyl)ruthenium(II)] ([Ru($\eta^5$-C$_5$PrH$_4$)(MeCN)$_3$]), [tris(acetonitrile)($\eta^5$-isopropylcyclopentadienyl)ruthenium(II)] ([Ru($\eta^5$-C$_5$$^i$PrH$_4$)(MeCN)$_3$]), [tris(acetonitrile)($\eta^5$-butylcyclopentadienyl)ruthenium(II)] ([Ru($\eta^5$-C$_5$BuH$_4$)(MeCN)$_3$]), [tris(acetonitrile)($\eta^5$-isobutylcyclopentadienyl)ruthenium(II)] ([Ru($\eta^5$-C$_5$$^i$BuH$_4$)(MeCN)$_3$]), [tris(acetonitrile)($\eta^5$-(sec-butyl)cyclopentadienyl)ruthenium(II)] ([Ru($\eta^5$-C$_5$$^s$BuH$_4$)(MeCN)$_3$]), [tris(acetonitrile)($\eta^5$-(tert-butyl)cyclopentadienyl)ruthenium(II)] ([Ru($\eta^5$-C$_5$$^t$BuH$_4$)(MeCN)$_3$]), [tris(acetonitrile)($\eta^5$-pentylcyclopentadienyl)ruthenium(II)] ([Ru($\eta^5$-C$_5$PeH$_4$)(MeCN)$_3$]), [tris(acetonitrile)($\eta^5$-(cyclopentyl)cyclopentadienyl)ruthenium(II)] ([Ru($\eta^5$-C$_5$$^c$PeH$_4$)(MeCN)$_3$]), [tris(acetonitrile)($\eta^5$-hexylcyclopentadienyl)ruthenium(II)] ([Ru($\eta^5$-C$_5$HxH$_4$)(MeCN)$_3$]), [tris(acetonitrile)($\eta^5$-1,2,3,4,5-pentamethylcyclopentadienyl)ruthenium(II)] ([Ru($\eta^5$-C$_5$Me$_5$)(MeCN)$_3$]),

[($\eta^5$-cyclopentadienyl)tris(propionitrile)ruthenium(II)] ([Ru($\eta^5$-C$_5$H$_5$)(EtCN)$_3$]), [($\eta^5$-methylcyclopentadienyl)tris(propionitrile)ruthenium(II)] ([Ru($\eta^5$-C$_5$MeH$_4$)(EtCN)$_3$]), [($\eta^5$-ethylcyclopentadienyl)tris(propionitrile)ruthenium(II)] ([Ru($\eta^5$-C$_5$EtH$_4$)(EtCN)$_3$]), [tris(propionitrile)($\eta^5$-propylcyclopentadienyl)ruthenium(II)] ([Ru($\eta^5$-C$_5$PrH$_4$)(EtCN)$_3$]), [($\eta^5$-isopropylcyclopentadienyl)tris(propionitrile)ruthenium(II)] ([Ru($\eta^5$-C$_5$$^i$PrH$_4$)(EtCN)$_3$]), [($\eta^5$-butylcyclopentadienyl)tris(propionitrile)ruthenium(II)] ([Ru($\eta^5$-C$_5$BuH$_4$)(EtCN)$_3$]), [($\eta^5$-isobutylcyclopentadienyl)tris(propionitrile)ruthenium(II)] ([Ru($\eta^5$-C$_5$$^i$BuH$_4$)(EtCN)$_3$]), [($\eta^5$-(sec-butyl)cyclopentadienyl)tris(propionitrile)ruthenium(II)] ([Ru($\eta^5$-C$_5$$^s$BuH$_4$)(EtCN)$_3$]), [($\eta^5$-(tert-butyl)cyclopentadienyl)tris(propionitrile)ruthenium(II)] ([Ru($\eta^5$-C$_5$$^t$BuH$_4$)(EtCN)$_3$]), [($\eta^5$-pentylcyclopentadienyl)tris(propionitrile)ruthenium(II)] ([Ru($\eta^5$-C$_5$PeH$_4$)(EtCN)$_3$]), [($\eta^5$-(cyclopentyl)cyclopentadienyl)tris(propionitrile)ruthenium(II)] ([Ru($\eta^5$-C$_5$$^c$PeH$_4$)(EtCN)$_3$]), [($\eta^5$-hexylcyclopentadienyl)tris(propionitrile)ruthenium(II)] ([Ru($\eta^5$-C$_5$HxH$_4$)(EtCN)$_3$]), [($\eta^5$-cyclopentadienyl)tris(pivalonitrile)ruthenium(II)] ([Ru($\eta^5$-C$_5$H$_5$)($^t$BuCN)$_3$]), [($\eta^5$-methylcyclopentadienyl)tris(pivalonitrile)ruthenium(II)] ([Ru($\eta^5$-C$_5$MeH$_4$)($^t$BuCN)$_3$]), [($\eta^5$-ethylcyclopentadienyl)tris(pivalonitrile)ruthenium(II)] ([Ru($\eta^5$-C$_5$EtH$_4$)($^t$BuCN)$_3$]), tris(pivalonitrile)($\eta^5$-propylcyclopentadienyl)ruthenium(II)] ([Ru($\eta^5$-C$_5$PrH$_4$)($^t$BuCN)$_3$]), [($\eta^5$-isopropylcyclopentadienyl)tris(pivalonitrile)ruthenium(II)] ([Ru($\eta^5$-C$_5$$^i$PrH$_4$)($^t$BuCN)$_3$]), [($\eta^5$-butylcyclopentadienyl)tris(pivalonitrile)ruthenium(II)] ([Ru($\eta^5$-C$_5$BuH$_4$)($^t$BuCN)$_3$]), [($\eta^5$-isobutylcyclopentadienyl)tris(pivalonitrile)ruthenium(II)] ([Ru($\eta^5$-C$_5$$^i$BuH$_4$)($^t$BuCN)$_3$]), [($\eta^5$-(sec-butyl)cyclopentadienyl)tris(pivalonitrile)ruthenium(II)] ([Ru($\eta^5$-C$_5$$^s$BuH$_4$)($^t$BuCN)$_3$]), [($\eta^5$-(tert-butyl)cyclopentadienyl)tris(pivalonitrile)ruthenium(II)] ([Ru($\eta^5$-C$_5$$^t$BuH$_4$)($^t$BuCN)$_3$]), [($\eta^5$-pentylcyclopentadienyl)tris(pivalonitrile)ruthenium(II)] ([Ru($\eta^5$-C$_5$PeH$_4$)($^t$BuCN)$_3$]), [($\eta^5$-(cyclopentyl)cyclopentadienyl)tris(pivalonitrile)ruthenium(II)] ([Ru($\eta^5$-C$_5$$^c$PeH$_4$)($^t$BuCN)$_3$]), and [($\eta^5$-hexylcyclopentadienyl)tris(pivalonitrile)ruthenium(II)] ([Ru($\eta^5$-C$_5$HxH$_4$)($^t$BuCN)$_3$]).

Examples of the counter anion $Z^-$ in formula (4) include those generally used as a counter anion of a cationic metal complex. Specific examples thereof include a fluoro complex anion such as tetrafluoroborate ion ($BF_4^-$), hexafluorophosphate ion ($PF_6^-$), hexafluoroantimonate ion ($SbF_6^-$) and tetrafluoroaluminate ion ($AlF_4^-$), a monovalent sulfonate ion such as trifluoromethanesulfonate ion ($CF_3SO_3^-$), methanesulfonate ion ($MeSO_3^-$) and methylsulfate ion ($MeSO_4^-$), a counter anion of a monobasic acid, such as nitrate ion ($NO_3^-$), perchlorate ion ($ClO_4^-$), tetrachloroaluminate ion ($AlCl_4^-$) and bis(trifluoromethanesulfonyl)amide ion (($CF_3SO_2)_2N^-$), a counter anion of a polybasic acid, such as sulfate ion ($SO_4^{2-}$), hydrogen sulfate ion ($HSO_4^-$), phosphate ion ($PO_4^{3-}$), monohydrogen phosphate ion ($HPO_4^{2-}$), dihydrogen phosphate ion ($H_2PO_4^-$), dimethylphosphate ion (($MeO)_2PO_4^-$) and diethylphosphate ion (($EtO)_2PO_4^-$), and a derivative thereof. In view of a high yield of the ruthenium complex (1), the counter anion $Z^-$ is preferably a fluoro complex anion such as $BF_4^-$ and $PF_6^-$, or a monovalent sulfonate ion such as $CF_3SO_3^-$ and $MeSO_3^-$.

More preferred specific examples of the cationic tris(nitrile) complex (4) include [tris(acetonitrile)($\eta^5$-cyclopentadienyl)ruthenium(II)][tetrafluoroborate] ([Ru($\eta^5$-C$_5$H$_5$)(MeCN)$_3$][BF$_4$]), [tris(acetonitrile)($\eta^5$-methylcyclopentadienyl)ruthenium(II)][tetrafluoroborate] ([Ru($\eta^5$-C$_5$MeH$_4$)(MeCN)$_3$][BF$_4$]), [tris(acetonitrile)($\eta^5$-ethylcyclopentadienyl)ruthenium(II)][tetrafluoroborate] ([Ru($\eta^5$-C$_5$EtH$_4$)(MeCN)$_3$][BF$_4$]), [tris(acetonitrile)($\eta^5$-1,2,3,4,5-pentamethylcyclopentadienyl)ruthenium(II)][tetrafluoroborate] ([Ru($\eta^5$-C$_5$Me$_5$)(MeCN)$_3$][BF$_4$]), [tris(acetonitrile)($\eta^5$-cyclopentadienyl)ruthenium(II)][hexafluorophosphate] ([Ru($\eta^5$-C$_5$H$_5$)(MeCN)$_3$][PF$_6$]), [tris(acetonitrile)($\eta^5$-methylcyclopentadienyl)ruthenium(II)][hexafluorophosphate] ([Ru($\eta^5$-C$_5$MeH$_4$)(MeCN)$_3$][PF$_6$]), [tris(acetonitrile)($\eta^5$-ethylcyclopentadienyl)ruthenium(II)][hexafluorophosphate] ([Ru($\eta^5$-C$_5$EtH$_4$)(MeCN)$_3$][PF$_6$]), [tris(acetonitrile)($\eta^5$-1,2,3,4,5-pentamethylcyclopentadienyl)ruthenium(II)][hexafluorophosphate] ([Ru($\eta^5$-C$_5$Me$_5$)(MeCN)$_3$][PF$_6$]), [tris(acetonitrile)($\eta^5$-cyclopentadienyl)ruthenium(II)][trifluoromethanesulfonate] ([Ru($\eta^5$-C$_5$H$_5$)(MeCN)$_3$][CF$_3$SO$_3$]), [tris(acetonitrile)($\eta^5$-methylcyclopentadienyl)ruthenium(II)][trifluoromethanesulfonate] ([Ru($\eta^5$-C$_5$MeH$_4$)(MeCN)$_3$][CF$_3$SO$_3$]), [tris(acetonitrile)($\eta^5$-ethylcyclo-pentadienyl)ruthenium(II)][trifluoromethanesulfonate] ([Ru($\eta^5$-C$_5$EtH$_4$)(MeCN)$_3$][CF$_3$SO$_3$]), [tris(acetonitrile)($\eta^5$-1,2,3,4,5-pentamethylcyclo-pentadienyl)ruthenium(II)][trifluoromethanesulfonate] ([Ru($\eta^5$-C$_5$Me$_5$)(MeCN)$_3$]

[CF$_3$SO$_3$]), [tris(acetonitrile)($\eta^5$-cyclopentadienyl)ruthenium(II)][methanesulfonate] ([Ru($\eta^5$-C$_5$H$_5$)(MeCN)$_3$][MeSO$_3$]), [tris(acetonitrile)($\eta^5$-methylcyclopentadienyl)ruthenium(II)][methanesulfonate] ([Ru($\eta^5$-C$_5$MeH$_4$)(MeCN)$_3$][MeSO$_3$]), [tris(acetonitrile)($\eta^5$-ethylcyclopentadienyl)ruthenium(II)][methanesulfonate] ([Ru($\eta^5$-C$_5$EtH$_4$)(MeCN)$_3$][MeSO$_3$]), and [tris(acetonitrile)($\eta^5$-1,2,3,4,5-pentamethylcyclo-pentadienyl)ruthenium(II)][methanesulfonate] ([Ru($\eta^5$-C$_5$Me$_5$)(MeCN)$_3$][MeSO$_3$]).

The alkyl group having a carbon number of 1 to 6 represented by R$^{20}$ and R$^{21}$ in formula (5) may be any of a linear alkyl group, a branched alkyl group and a cyclic alkyl group, and specific examples thereof include a methyl group, an ethyl group, a propyl group, an isopropyl group, a cyclopropyl group, a butyl group, an isobutyl group, a sec-butyl group, a tert-butyl group, a cyclobutyl group, a pentyl group, a 1-methylbutyl group, a 2-methylbutyl group, an isopentyl group, a neopentyl group, a tert-pentyl group, a cyclopentyl group, a cyclobutylmethyl group, a hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a cyclohexyl group, a cyclopentylmethyl group, a 1-cyclobutylethyl group, and a 2-cyclobutylethyl group.

Specific examples of the enone derivative (5) include 4-methylpent-3-en-2-one (mesityl oxide), 5-methylhex-4-en-3-one, 2-methylhept-2-en-4-one, 2,5-dimethylhex-4-en-3-one, 2-methyloct-2-en-4-one, 2,6-dimethylhept-2-en-4-one, 2,5-dimethylhept-2-en-4-one, 2,2,5-trimethylhex-4-en-3-one, 2-methylnon-2-en-4-one, 2,5,5-trimethylhept-2-en-4-one, 2-methyldec-2-en-4-one, 1-cyclohexyl-3-methylbut-2-en-1-one, 4-methylhex-3-en-2-one, 4-methylhept-3-en-2-one, 4,5-dimethylhex-3-en-2-one, 4-methyloct-3-en-2-one, 4,6-dimethylhept-3-en-2-one, 4,5-dimethylhept-3-en-2-one, 4,5,5-trimethylhex-3-en-2-one, 4-methylnon-3-en-2-one, 4-methyldec-3-en-2-one, 4-cyclohexylpent-3-en-2-one, 5-methylhept-4-en-3-one, 6-methylnon-5-en-4-one, 2,5,6-trimethylhept-4-en-3-one, 2,2,5,6,6-pentamethylhept-4-en-3-one, and 3,3,6,7,7-pentamethylnon-5-en-4-one. In view of a high yield of the ruthenium complex (1), mesityl oxide or 2,2,5,6,6-pentamethylhept-4-en-3-one are preferred, and mesityl oxide is more preferred.

The base that can be used in production method 1 includes an inorganic base and an organic base. Examples of the inorganic base include an alkali metal carbonate such as lithium carbonate, sodium carbonate and potassium carbonate, an alkali metal bicarbonate salt such as lithium bicarbonate, sodium bicarbonate and potassium bicarbonate, a Group 2 metal carbonate such as magnesium carbonate, calcium carbonate and strontium carbonate, a typical metal hydroxide such as lithium hydroxide, sodium hydroxide, potassium hydroxide, magnesium hydroxide, calcium hydroxide and strontium hydroxide, a typical metal hydride such as lithium hydride, sodium hydride, potassium hydride, magnesium hydride, calcium hydride and aluminum hydride, a typical metal hydride complex compound such as sodium borohydride and aluminum lithium hydride, and an alkali metal amide such as lithium amide, sodium amide and lithium dialkylamide. Examples of the organic base include an alkylamine such as diethylamine, triethylamine, diethylisopropylamine and tributylamine, a cyclic amine such as pyrrolidine, piperidine, piperazine and 1,4-diazabicyclooctane, and pyridine. In view of a high yield of the ruthenium complex (1), the base is preferably an alkali metal carbonate or an alkyl amine, more preferably lithium carbonate, sodium carbonate, potassium carbonate or triethylamine, still more preferably lithium carbonate or triethylamine.

For the reason that the yield of the ruthenium complex (1) is high, production method 1 is preferably performed in an inert gas. Specific examples of the inert gas include helium, neon, argon, krypton, xenon, and nitrogen gas, with argon or nitrogen gas being preferred.

For the reason that the yield of the ruthenium complex (1) is high, production method 1 is preferably performed in an organic solvent. In the case of performing production method 1 in an organic solvent, specific examples of the organic solvent include an aliphatic hydrocarbon such as pentane, hexane, heptane, octane, cyclohexane, methylcyclohexane, ethylcyclohexane and petroleum ether, an ether such as diethyl ether, diisopropyl ether, dibutyl ether, cyclopentyl methyl ether, cyclopentyl ethyl ether, tetrahydrofuran, dioxane and 1,2-dimethoxyethane, a ketone such as acetone, methyl ethyl ketone, 3-pentanone, cyclopentanone and cyclohexanone, and an alcohol such as methanol, ethanol, propanol, isopropanol, tert-butanol and ethylene glycol. Of these organic solvents, one kind may be used alone, or a plurality of kinds may be mixed in an arbitrary ratio and used. In view of a high yield of the ruthenium complex (1), diethyl ether, tetrahydrofuran, acetone, methanol and hexane are preferred as the organic solvent.

Methods for obtaining the cationic tris(nitrile) complex (4) and the enone derivative (5) are described below. The method for obtaining the cationic tris(nitrile) complex (4) includes the production methods described, for example, in Non-Patent Document 3 and Non-Patent Document 4, other than the later-described production method 2 of the present invention. The method for obtaining the enone derivative (5) includes the methods described, for example, in Journal of Organometallic Chemistry, Vol. 402, page 17 (1991), and Japanese Patent 3,649,441, other than the purchase of a commercial product.

The molar ratio between the cationic tris(nitrile) complex (4) and the enone derivative (5) when performing production method 1 is described below. Preferably, an equimolar or greater amount of an enone derivative (5) per mol of a cationic tris(nitrile) complex (4), and a base are used, whereby the ruthenium complex (1) can be efficiently produced.

In production method 1, the reaction temperature and the reaction time are not particularly limited, and general conditions employed by one skilled in the art when producing a metal complex may be used. As a specific example, a reaction temperature appropriately selected from a temperature range of −80° C. to 120° C. and a reaction time appropriately selected from the range of 10 minutes to 120 hours are employed, whereby the ruthenium complex (1) can be efficiently produced.

The ruthenium complex (1) produced by production method 1 may be purified by appropriately selecting and using a general purification method employed by one skilled in the art when purifying a metal complex. The purification method specifically includes filtration, extraction, centrifugation, decantation, distillation, sublimation, crystallization, etc.

The cationic tris(nitrile) complex (4b) of the present invention is described below. The alkyl group having a carbon number of 2 to 6 represented by R$^{1b}$ in formula (4b) may be any of a linear alkyl group, a branched alkyl group and a cyclic alkyl group, and specific examples thereof include an ethyl group, a propyl group, an isopropyl group, a cyclopropyl group, a butyl group, an isobutyl group, a sec-butyl group, a tert-butyl group, a cyclobutyl group, a pentyl group, a 1-methylbutyl group, a 2-methylbutyl group, an isopentyl group, a neopentyl group, a tert-pentyl group, a cyclopentyl group, a cyclobutylmethyl group, a hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a cyclohexyl group, a cyclopentylmethyl group, a 1-cyclobutylethyl group, and a 2-cyclobutylethyl group. From the standpoint of producing a raw material for synthesis of a ruthenium complex (1) having vapor pressure and thermal stability suitable particularly as a CVD material or an ALD material, $R^{1b}$ is preferably an alkyl group having a carbon number of 2 to 4, more preferably an ethyl group.

The alkyl group having a carbon number of 1 to 4 represented by $R^{19b}$ in formula (4b) may be any of a linear alkyl group, a branched alkyl group and a cyclic alkyl group, and specific examples thereof include a methyl group, an ethyl group, a propyl group, an isopropyl group, a cyclopropyl group, a butyl group, an isobutyl group, a sec-butyl group, a tert-butyl group, and a cyclobutyl group. In view of a high yield when used as a raw material for synthesis of the ruthenium complex (1), $R^{19b}$ is preferably a methyl group.

Specific examples of the cation moiety of the cationic tris(nitrile) complex (4b) include [tris(acetonitrile)($\eta^5$-ethylcyclopentadienyl)ruthenium(II)] ([Ru($\eta^5$-C$_5$EtH$_4$)(MeCN)$_3$]), [tris(acetonitrile)($\eta^5$-propylcyclopentadienyl)ruthenium(II)] ([Ru($\eta^5$-C$_5$PrH$_4$)(MeCN)$_3$]), [tris(acetonitrile)($\eta^5$-isopropylcyclopentadienyl)ruthenium(II)] ([Ru($\eta^5$-C$_5{}^i$PrH$_4$)(MeCN)$_3$]), [tris(acetonitrile)($\eta^5$-butylcyclopentadienyl)ruthenium(II)] ([Ru($\eta^5$-C$_5$BuH$_4$)(MeCN)$_3$]), [tris(acetonitrile)($\eta^5$-isobutylcyclopentadienyl)ruthenium(II)] ([Ru($\eta^5$-C$_5{}^i$BuH$_4$)(MeCN)$_3$]), [tris(acetonitrile)($\eta^5$-(sec-butyl)cyclopentadienyl)ruthenium(II)] ([Ru($\eta^5$-C$_5{}^s$BuH$_4$)(MeCN)$_3$]), [tris(acetonitrile)($\eta^5$-(tert-butyl)cyclopentadienyl)ruthenium(II)] ([Ru($\eta^5$-C$_5{}^t$BuH$_4$)(MeCN)$_3$]), [tris(acetonitrile)($\eta^5$-pentylcyclopentadienyl)ruthenium(II)] ([Ru($\eta^5$-C$_5$PeH$_4$)(MeCN)$_3$]), [tris(acetonitrile)($\eta^5$-(cyclopentyl)cyclopentadienyl)ruthenium(II)] ([Ru($\eta^5$-C$_5{}^c$PeH$_4$)(MeCN)$_3$]), [tris(acetonitrile)($\eta^5$-hexylcyclopentadienyl)ruthenium(II)] ([Ru($\eta^5$-C$_5$HxH$_4$)(MeCN)$_3$]), [($\eta^5$-ethylcyclopentadienyl)tris(propionitrile)ruthenium(II)] ([Ru($\eta^5$-C$_5$EtH$_4$)(EtCN)$_3$]), [tris(propionitrile)($\eta^5$-propylcyclopentadienyl)ruthenium(II)] ([Ru($\eta^5$-C$_5$PrH$_4$)(EtCN)$_3$]), [($\eta^5$-isopropylcyclopentadienyl)tris(propionitrile)ruthenium(II)] ([Ru($\eta^5$-C$_5{}^i$PrH$_4$)(EtCN)$_3$]), [($\eta^5$-butylcyclopentadienyl)tris(propionitrile)ruthenium(II)] ([Ru($\eta^5$-C$_5$BuH$_4$)(EtCN)$_3$]), [($\eta^5$-isobutylcyclopentadienyl)tris(propionitrile)ruthenium(II)] ([Ru($\eta^5$-C$_5{}^i$BuH$_4$)(EtCN)$_3$]), [($\eta^5$-(sec-butyl)cyclopentadienyl)tris(propionitrile)ruthenium(II)] ([Ru($\eta^5$-C$_5{}^s$BuH$_4$)(EtCN)$_3$]), [($\eta^5$-(tert-butyl)cyclopentadienyl)tris(propionitrile)ruthenium(II)] ([Ru($\eta^5$-C$_5{}^t$BuH$_4$)(EtCN)$_3$]), [($\eta^5$-pentylcyclopentadienyl)tris(propionitrile)ruthenium(II)] ([Ru($\eta^5$-C$_5$PeH$_4$)(EtCN)$_3$]), [($\eta^5$-(cyclopentyl)cyclopentadienyl)tris(propionitrile)ruthenium(II)] ([Ru($\eta^5$-C$_5{}^c$PeH$_4$)(EtCN)$_3$]), [($\eta^5$-hexylcyclopentadienyl)tris(propionitrile)ruthenium(II)] ([Ru($\eta^5$-C$_5$HxH$_4$)(EtCN)$_3$]), [($\eta^5$-ethylcyclopentadienyl)tris(pivalonitrile)ruthenium(II)] ([Ru($\eta^5$-C$_5$EtH$_4$)($^t$BuCN)$_3$]), [tris(pivalonitrile)($\eta^5$-propylcyclopentadienyl)ruthenium(II)] ([Ru($\eta^5$-C$_5$PrH$_4$)($^t$BuCN)$_3$]), [($\eta^5$-isopropylcyclopentadienyl)tris(pivalonitrile)ruthenium(II)] ([Ru($\eta^5$-C$_5{}^i$PrH$_4$)($^t$BuCN)$_3$]), [($\eta^5$-butylcyclopentadienyl)tris(pivalonitrile)ruthenium(II)] ([Ru($\eta^5$-C$_5$BuH$_4$)($^t$BuCN)$_3$]), [($\eta^5$-isobutylcyclopentadienyl)tris(pivalonitrile)ruthenium(II)] ([Ru($\eta^5$-C$_5{}^i$BuH$_4$)($^t$BuCN)$_3$]), [($\eta^5$-(sec-butyl)cyclopentadienyl)tris(pivalonitrile)ruthenium(II)] ([Ru($\eta^5$-C$_5{}^s$BuH$_4$)($^t$BuCN)$_3$]), [($\eta^5$-(tert-butyl)cyclopentadienyl)tris(pivalonitrile)ruthenium(II)] ([Ru($\eta^5$-C$_5{}^t$BuH$_4$)($^t$BuCN)$_3$]), [($\eta^5$-pentylcyclopentadienyl)tris(pivalonitrile)ruthenium(II)] ([Ru($\eta^5$-C$_5$PeH$_4$)($^t$BuCN)$_3$]), [($\eta^5$-(cyclopentyl)cyclopentadienyl)tris(pivalonitrile)ruthenium(II)] ([Ru($\eta^5$-C$_5{}^c$PeH$_4$)($^t$BuCN)$_3$]), and [($\eta^5$-hexylcyclopentadienyl)tris(pivalonitrile)ruthenium(II)] ([Ru($\eta^5$-C$_5$HxH$_4$)($^t$BuCN)$_3$]). Among others, [Ru($\eta^5$-C$_5$EtH$_4$)(MeCN)$_3$], [Ru($\eta^5$-C$_5$PrH$_4$)(MeCN)$_3$], [Ru($\eta^5$-C$_5{}^i$PrH$_4$)(MeCN)$_3$], [Ru($\eta^5$-C$_5$BuH$_4$)(MeCN)$_3$], [Ru($\eta^5$-C$_5{}^i$BuH$_4$)(MeCN)$_3$], [Ru($\eta^5$-C$_5{}^s$BuH$_4$)(MeCN)$_3$], [Ru($\eta^5$-C$_5{}^t$BuH$_4$)(MeCN)$_3$], etc. are preferred, and [Ru($\eta^5$-C$_5$EtH$_4$)(MeCN)$_3$] is more preferred.

Examples of the counter anion $Zb^-$ in formula (4b) include those generally used as a counter anion of a cationic metal complex. Specific examples thereof include a fluoro complex anion such as tetrafluoroborate ion ($BF_4^-$), hexafluorophosphate ion ($PF_6^-$), hexafluoroantimonate ion ($SbF_6^-$) and tetrafluoroaluminate ion ($AlF_4^-$), a monovalent sulfonate ion such as trifluoromethanesulfonate ion ($CF_3SO_3^-$), methanesulfonate ion ($MeSO_3^-$) and methylsulfate ion ($MeSO_4^-$), a counter anion of a monobasic acid, such as nitrate ion ($NO_3^-$), perchlorate ion ($ClO_4^-$), tetrachloroaluminate ion ($AlCl_4^-$) and bis(trifluoromethanesulfonyl)amide ion (($CF_3SO_2)_2N^-$), a counter anion of a polybasic acid, such as sulfate ion ($SO_4^{2-}$), hydrogen sulfate ion ($HSO_4^-$), phosphate ion ($PO_4^{3-}$), monohydrogen phosphate ion ($HPO_4^{2-}$), dihydrogen phosphate ion ($H_2PO_4^-$), dimethylphosphate ion (($MeO)_2PO_4^-$) and diethylphosphate ion (($EtO)_2PO_4^-$), and a derivative thereof. In view of a high yield of the ruthenium complex (1), the counter anion $Zb^-$ is preferably a fluoro complex anion such as $BF_4^-$ and $PF_6^-$, or a monovalent sulfonate ion such as $CF_3SO_3^-$ and $MeSO_3^-$.

More specifically, preferred examples of the cationic tris(nitrile) complex (4b) include [tris(acetonitrile)($\eta^5$-ethylcyclopentadienyl)ruthenium(II)][tetrafluoroborate] ([Ru($\eta^5$-C$_5$EtH$_4$)(MeCN)$_3$][BF$_4$]), [tris(acetonitrile)($\eta^5$-ethylcyclopentadienyl)ruthenium(II)][hexafluorophosphate] ([Ru($\eta^5$-C$_5$EtH$_4$)(MeCN)$_3$][PF$_6$]), [tris(acetonitrile)($\eta^5$-ethylcyclopentadienyl)ruthenium(II)][trifluoromethanesulfonate] ([Ru($\eta^5$-C$_5$EtH$_4$)(MeCN)$_3$][CF$_3$SO$_3$]), [tris(acetonitrile)($\eta^5$-propylcyclopentadienyl)ruthenium(II)][tetrafluoroborate] ([Ru($\eta^5$-C$_5$PrH$_4$)(MeCN)$_3$][BF$_4$]), [tris(acetonitrile)($\eta^5$-propylcyclopentadienyl)ruthenium(II)][hexafluorophosphate] ([Ru($\eta^5$-C$_5$PrH$_4$)(MeCN)$_3$][PF$_6$]), [tris(acetonitrile)($\eta^5$-propylcyclopentadienyl)ruthenium(II)][trifluoromethanesulfonate] ([Ru($\eta^5$-C$_5$PrH$_4$)(MeCN)$_3$][CF$_3$SO$_3$]), [tris(acetonitrile)($\eta^5$-isopropylcyclopentadienyl)ruthenium(II)][tetrafluoroborate] ([Ru($\eta^5$-C$_5{}^i$PrH$_4$)(MeCN)$_3$][BF$_4$]), [tris(acetonitrile)($\eta^5$-isopropylcyclopentadienyl)ruthenium(II)][hexafluorophosphate] ([Ru($\eta^5$-C$_5{}^i$PrH$_4$)(MeCN)$_3$][PF$_6$]), [tris(acetonitrile)($\eta^5$-isopropylcyclopentadienyl)ruthenium(II)][trifluoromethanesulfonate] ([Ru($\eta^5$-C$_5{}^i$PrH$_4$)(MeCN)$_3$][CF$_3$SO$_3$]), [tris(acetonitrile)($\eta^5$-butylcyclopentadienyl)ruthenium(II)][tetrafluoroborate] ([Ru($\eta^5$-C$_5$BuH$_4$)(MeCN)$_3$][BF$_4$]), [tris(acetonitrile)($\eta^5$-butylcyclopentadienyl)ruthenium(II)][hexafluorophosphate] ([Ru($\eta^5$-C$_5$BuH$_4$)(MeCN)$_3$][PF$_6$]), [tris(acetonitrile)($\eta^5$-butylcyclopentadienyl)ruthenium(II)][trifluoromethanesulfonate] ([Ru($\eta^5$-C$_5$BuH$_4$)(MeCN)$_3$][CF$_3$SO$_3$]), [tris(acetonitrile)($\eta^5$-isobutylcyclopentadienyl)ruthenium(II)][tetrafluoroborate] ([Ru($\eta^5$-C$_5{}^i$BuH$_4$)(MeCN)$_3$][BF$_4$]), [tris(acetonitrile)($\eta^5$-isobutylcyclopentadienyl)ruthenium(II)][hexafluorophosphate] ([Ru($\eta^5$-C$_5{}^i$BuH$_4$)(MeCN)$_3$][PF$_6$]), [tris(acetonitrile)($\eta^5$-isobutylcyclo-pentadienyl)ruthenium (II)][trifluoromethanesulfonate] ([Ru(η⁵-C₅ⁱBuH₄)(MeCN)₃][CF₃SO₃]), [tris(acetonitrile)(η⁵-(sec-butyl)cyclopentadienyl)ruthenium(II)][tetrafluoroborate] ([Ru(η⁵-C₅ˢBuH₄)(MeCN)₃][BF₄]), [tris(acetonitrile)(η⁵-(sec-butyl)cyclopentadienyl)ruthenium(II)][hexafluorophosphate] ([Ru(η⁵-C₅ˢBuH₄)(MeCN)₃][PF₆]), [tris(acetonitrile)(η⁵-(sec-butyl)cyclopentadienyl)ruthenium(II)][trifluoromethanesulfonate] ([Ru(η⁵-C₅ˢBuH₄)(MeCN)₃][CF₃SO₃]), [tris(acetonitrile)(η⁵-(tert-butyl)cyclopentadienyl)ruthenium(II)][tetrafluoroborate] ([Ru(η⁵-C₅ᵗBuH₄)(MeCN)₃][BF₄]), [tris(acetonitrile)(η⁵-(tert-butyl)cyclopentadienyl)ruthenium(II)][hexafluorophosphate] ([Ru(η⁵-C₅ᵗBuH₄)(MeCN)₃][PF₆]), and [tris(acetonitrile)(η⁵-(tert-butyl)cyclopentadienyl)ruthenium(II)][trifluoromethanesulfonate] ([Ru(η⁵-C₅ᵗBuH₄)(MeCN)₃][CF₃SO₃]).

Of these, [tris(acetonitrile)(η⁵-ethylcyclopentadienyl)ruthenium(II)][tetrafluoroborate] ([Ru(η⁵-C₅EtH₄)(MeCN)₃][BF₄]), [tris(acetonitrile)(η⁵-ethylcyclopentadienyl)ruthenium(II)][hexafluorophosphate] ([Ru(η⁵-C₅EtH₄)(MeCN)₃][PF₆]), [tris(acetonitrile)(η⁵-ethylcyclopentadienyl)ruthenium(II)][trifluoromethanesulfonate] ([Ru(η⁵-C₅EtH₄)(MeCN)₃][CF₃SO₃]), etc. are more preferred.

The production method of the cationic tris(nitrile) complex (4b) of the present invention is described below. The cationic tris(nitrile) complex (4b) can be produced according to production method 2 of a ruthenium cationic tris(nitrile) complex (4) shown below. Production method 2 is a method of reacting a ruthenocene derivative (6), nitrile R¹⁹CN with a protonic acid H⁺Z⁻ to produce a cationic tris(nitrile) complex (4).

[Chem. 9]

Production Method 2:

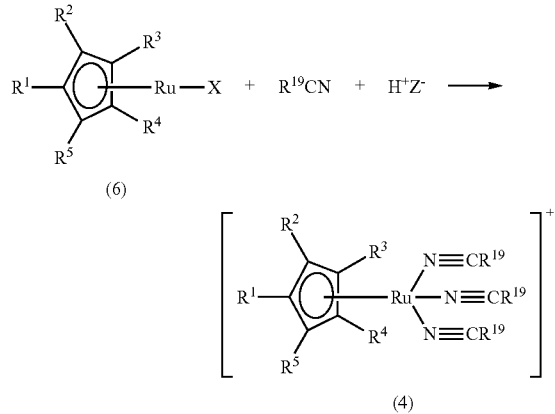

(wherein R¹, R², R³, R⁴, R⁵, X, R¹⁹ and Z⁻ have the same meanings as above.)

The alkyl group having a carbon number of 1 to 4 represented by R¹⁹ may be any of a linear alkyl group, a branched alkyl group and a cyclic alkyl group, and specific examples thereof include a methyl group, an ethyl group, a propyl group, an isopropyl group, a cyclopropyl group, a butyl group, an isobutyl group, a sec-butyl group, a tert-butyl group, and a cyclobutyl group. In view of a high yield, R²¹ is preferably a methyl group. Specific examples of the nitrile include acetonitrile, propionitrile, butyronitrile, isobutyronitrile, cyclopropanecarbonitrile, pentylonitrile, isopentylonitrile, 3-methylbutanenitrile, 2-methylbutanenitrile, pivalonitrile, and cyclobutanecarbonitrile, and in view of a high yield, acetonitrile is preferred.

X in formula (6) represents an η⁵-(unsubstituted or substituted)cyclopentadienyl ligand represented by formula (7):

[Chem. 10]

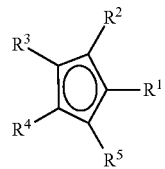

(7)

(wherein R¹, R², R³, R⁴ and R⁵ have the same meanings as above) or an η⁵-2,4-dimethyl-2,4-pentadienyl ligand. Specific examples of the η⁵-(unsubstituted or substituted)cyclopentadienyl ligand include an η⁵-cyclopentadienyl ligand, an η⁵-methylcyclopentadienyl ligand, an η⁵-ethylcyclopentadienyl ligand, an η⁵-propylcyclopentadienyl ligand, an η⁵-isopropylcyclopentadienyl ligand, an η⁵-butylcyclopentadienyl ligand, an η⁵-isobutylcyclopentadienyl ligand, an η⁵-(sec-butyl)cyclopentadienyl ligand, an η⁵-(tert-butyl)cyclopentadienyl ligand, an η⁵-pentylcyclopentadienyl ligand, an η⁵-(cyclopentyl)cyclopentadienyl ligand, an η⁵-hexylcyclopentadienyl ligand, an η⁵-1,2-dimethylcyclopentadienyl ligand, an η⁵-1,3-dimethylcyclopentadienyl ligand, an η⁵-1,3-di(isopropyl)cyclopentadienyl ligand, an η⁵-1,2,4-tri(isopropyl)cyclopentadienyl ligand, an η⁵-1,3-di(tert-butyl)cyclopentadienyl ligand, and an η⁵-1,2,3,4,5-pentamethylcyclopentadienyl ligand. For the reason that the ruthenocene derivative (6) is easily obtained, X is preferably an η⁵-(unsubstituted or substituted)cyclopentadienyl ligand, more preferably an η⁵-cyclopentadienyl ligand, an η⁵-methylcyclopentadienyl ligand, or an η⁵-ethylcyclopentadienyl ligand.

More specifically, examples of the ruthenocene derivative (6) include bis(η⁵-cyclopentadienyl)ruthenium ((η⁵-C₅H₅)₂Ru), bis(η⁵-methylcyclopentadienyl)ruthenium ((η⁵-C₅MeH₄)₂Ru), bis(η⁵-ethylcyclopentadienyl)ruthenium ((η⁵-C₅EtH₄)₂Ru), bis(η⁵-propylcyclopentadienyl)ruthenium ((η⁵-C₅PrH₄)₂Ru), bis(η⁵-isopropylcyclopentadienyl)ruthenium ((η⁵-C₅ⁱPrH₄)₂Ru), bis(η⁵-butylcyclopentadienyl)ruthenium ((η⁵-C₅BuH₄)₂Ru), bis(η⁵-isobutylcyclopentadienyl)ruthenium ((η⁵-C₅ⁱBuH₄)₂Ru), bis(η⁵-(sec-butyl)cyclopentadienyl)ruthenium ((η⁵-C₅ˢBuH₄)₂Ru), bis(η⁵-(tert-butyl)cyclopentadienyl)ruthenium ((η⁵-C₅ᵗBuH₄)₂Ru), bis(η⁵-pentylcyclopentadienyl)ruthenium ((η⁵-C₅PeH₄)₂Ru), bis(η⁵-(cyclopentyl)cyclopentadienyl)ruthenium ((η⁵-C₅ᶜPeH₄)₂Ru), bis(η⁵-hexylcyclopentadienyl)ruthenium ((η⁵-C₅HxH₄)₂Ru), bis(η⁵-1,2-dimethylcyclopentadienyl)ruthenium ((η⁵-C₅Me₂H₃)₂Ru), bis(η⁵-1,3-dimethylcyclopentadienyl)ruthenium ((η⁵-C₅Me₂H₃)₂Ru), bis(η⁵-1,3-di(isopropyl)cyclopentadienyl)ruthenium ((η⁵-C₅(ⁱPr)₂H₃)₂Ru), bis(η⁵-1,2,4-tri(isopropyl)cyclopentadienyl)ruthenium ((η⁵-C₅(ⁱPr)₃H₂)₂Ru), bis(η⁵-1,3-di(tert-butyl)cyclopentadienyl)ruthenium ((η⁵-C₅(ᵗBu)₂H₃)₂Ru), bis(η⁵-1,2,3,4,5-pentamethylcyclopentadienyl)ruthenium ((η⁵-C₅Me₅)₂Ru), (η⁵-cyclopentadienyl)(η⁵-1,2,3,4,5-pentamethylcyclopentadienyl)ruthenium ((η⁵-C₅H₅)(η⁵-C₅Me₅)Ru), (η⁵-cyclopentadienyl)(η⁵-2,4-dimethyl-2,4-pentadienyl)ruthenium (Ru(η⁵-C₅H₅)(η⁵-CH₂C(Me)CHC(Me)CH₂)), (η⁵-2,4-dimethyl-2,4-pentadienyl)(η⁵-methylcyclopentadienyl)ruthenium (Ru(η⁵-C₅MeH₄)(η⁵-

CH₂C(Me)CHC(Me)CH₂)), ($\eta^5$-2,4-dimethyl-2,4-pentadienyl)($\eta^5$-ethylcyclopentadienyl)ruthenium (Ru($\eta^5$-C₅EtH₄)($\eta^5$-CH₂C(Me)CHC(Me)CH₂)), ($\eta^5$-2,4-dimethyl-2,4-pentadienyl)($\eta^5$-propylcyclopentadienyl)ruthenium (Ru($\eta^5$-C₅PrH₄)($\eta^5$-CH₂C(Me)CHC(Me)CH₂)), ($\eta^5$-2,4-dimethyl-2,4-pentadienyl)($\eta^5$-isopropylcyclopentadienyl)ruthenium (Ru($\eta^5$-C₅$^i$PrH₄)($\eta^5$-CH₂C(Me)CHC(Me)CH₂)), ($\eta^5$-2,4-dimethyl-2,4-pentadienyl)($\eta^5$-butylcyclopentadienyl)ruthenium (Ru($\eta^5$-C₅BuH₄)($\eta^5$-CH₂C(Me)CHC(Me)CH₂)), ($\eta^5$-2,4-dimethyl-2,4-pentadienyl)($\eta^5$-isobutylcyclopentadienyl)ruthenium (Ru($\eta^5$-C₅$^i$BuH₄)($\eta^5$-CH₂C(Me)CHC(Me)CH₂)), ($\eta^5$-2,4-dimethyl-2,4-pentadienyl)($\eta^5$-(sec-butyl)cyclopentadienyl)ruthenium (Ru($\eta^5$-C₅$^s$BuH₄)($\eta^5$-CH₂C(Me)CHC(Me)CH₂)), ($\eta^5$-2,4-dimethyl-2,4-pentadienyl)($\eta^5$-(tert-butyl)cyclopentadienyl)ruthenium (Ru($\eta^5$-C₅$^t$BuH₄)($\eta^5$-CH₂C(Me)CHC(Me)CH₂)), ($\eta^5$-2,4-dimethyl-2,4-pentadienyl)($\eta^5$-pentylcyclopentadienyl)ruthenium (Ru($\eta^5$-C₅PeH₄)($\eta^5$-CH₂C(Me)CHC(Me)CH₂)), ($\eta^5$-2,4-dimethyl-2,4-pentadienyl)($\eta^5$-(cyclopentyl)cyclopentadienyl)ruthenium (Ru($\eta^5$-C₅$^c$PeH₄)($\eta^5$-CH₂C(Me)CHC(Me)CH₂)), ($\eta^5$-2,4-dimethyl-2,4-pentadienyl)($\eta^5$-hexylcyclopentadienyl)ruthenium (Ru($\eta^5$-C₅HxH₄)($\eta^5$-CH₂C(Me)CHC(Me)CH₂)), and ($\eta^5$-2,4-dimethyl-2,4-pentadienyl)($\eta^5$-1,2,3,4,5-pentamethylcyclopentadienyl)ruthenium (Ru($\eta^5$-C₅Me₅)($\eta^5$-CH₂C(Me)CHC(Me)CH₂)).

Of these, bis($\eta^5$-cyclopentadienyl)ruthenium ($\eta^5$-C₅H₅)₂Ru), bis($\eta^5$-methylcyclopentadienyl)ruthenium ($\eta^5$-C₅MeH₄)₂Ru), bis($\eta^5$-ethylcyclopentadienyl)ruthenium ($\eta^5$-C₅EtH₄)₂Ru), bis($\eta^5$-propylcyclopentadienyl)ruthenium ($\eta^5$-C₅PrH₄)₂Ru), bis($\eta^5$-isopropylcyclopentadienyl)ruthenium ($\eta^5$-C₅$^i$PrH₄)₂Ru), bis($\eta^5$-butylcyclopentadienyl)ruthenium ($\eta^5$-C₅BuH₄)₂Ru), bis($\eta^5$-isobutylcyclopentadienyl)ruthenium ($\eta^5$-C₅$^i$BuH₄)₂Ru), bis($\eta^5$-(sec-butyl)cyclopentadienyl)ruthenium (($\eta^5$-C₅$^s$BuH₄)₂Ru), bis($\eta^5$-(tert-butyl)cyclopentadienyl)ruthenium ($\eta^5$-C₅$^t$BuH₄)₂Ru), bis($\eta^5$-pentylcyclopentadienyl)ruthenium ($\eta^5$-C₅PeH₄)₂Ru), bis($\eta^5$-(cyclopentyl)cyclopentadienyl)ruthenium (($\eta^5$-C₅$^c$PeH₄)₂Ru), bis($\eta^5$-hexylcyclopentadienyl)ruthenium (($\eta^5$-C₅HxH₄)₂Ru), bis($\eta^5$-1,2-dimethylcyclopentadienyl)ruthenium (($\eta^5$-C₅Me₂H₃)₂Ru), bis($\eta^5$-1,3-dimethylcyclopentadienyl)ruthenium (($\eta^5$-C₅Me₂H₃)₂Ru), bis($\eta^5$-1,3-di(isopropyl)cyclopentadienyl)ruthenium (($\eta^5$-C₅($^i$Pr)₂H₃)₂Ru), bis($\eta^5$-1,2,4-tri(isopropyl)cyclopentadienyl)ruthenium (($\eta^5$-C₅($^i$Pr)₃H₂)₂Ru), bis($\eta^5$-1,3-di(tert-butyl)cyclopentadienyl)ruthenium (($\eta^5$-C₅($^t$Bu)₂H₃)₂Ru) and bis($\eta^5$-1,2,3,4,5-pentamethylcyclopentadienyl)ruthenium ($\eta^5$-C₅Me₅)₂Ru) are preferred; bis($\eta^5$-cyclopentadienyl)ruthenium ($\eta^5$-C₅H₅)₂Ru), bis($\eta^5$-methylcyclopentadienyl)ruthenium (($\eta^5$-C₅MeH₄)₂Ru), bis($\eta^5$-ethylcyclopentadienyl)ruthenium ($\eta^5$-C₅EtH₄)₂Ru), bis($\eta^5$-propylcyclopentadienyl)ruthenium ($\eta^5$-C₅PrH₄)₂Ru), bis($\eta^5$-isopropylcyclopentadienyl)ruthenium ($\eta^5$-C₅$^i$PrH₄)₂Ru), bis($\eta^5$-butylcyclopentadienyl)ruthenium (($\eta^5$-C₅BuH₄)₂Ru), bis($\eta^5$-isobutylcyclopentadienyl)ruthenium (($\eta^5$-C₅$^i$BuH₄)₂Ru), bis($\eta^5$-(sec-butyl)cyclopentadienyl)ruthenium (($\eta^5$-C₅$^s$BuH₄)₂Ru), bis($\eta^5$-(tert-butyl)cyclopentadienyl)ruthenium (($\eta^5$-C₅$^t$BuH₄)₂Ru), bis($\eta^5$-pentylcyclopentadienyl)ruthenium (($\eta^5$-C₅PeH₄)₂Ru), bis($\eta^5$-(cyclopentyl)cyclopentadienyl)ruthenium (($\eta^5$-C₅$^c$PeH₄)₂Ru) and bis($\eta^5$-hexylcyclopentadienyl)ruthenium (($\eta^5$-C₅HxH₄)₂Ru) are more preferred; and bis($\eta^5$-cyclopentadienyl)ruthenium (($\eta^5$-C₅H₅)₂Ru), bis($\eta^5$-methylcyclopentadienyl)ruthenium (($\eta^5$-C₅MeH₄)₂Ru) and bis($\eta^5$-ethylcyclopentadienyl)ruthenium (($\eta^5$-C₅EtH₄)₂Ru) are still more preferred.

As the ruthenocene derivative (6) that can be used as a raw material for synthesis in production method 2, a commercially available product may be used as it is, or a compound synthesized according to a known method described, for example, in Organic Syntheses, Vol. 41, page 96 (1961), JP-A-2003-342286 (the term "JP-A" as used herein means an "unexamined published Japanese patent application"), and Organometallics, Vol. 5, page 2321 (1986) may also be used.

Z⁻ in the protonic acid H⁺Z⁻ that can be used in production method 2 includes, for example, a fluoro complex anion such as tetrafluoroborate ion (BF₄⁻) and hexafluorophosphate ion (PF₆⁻), a sulfonate ion such as trifluoromethanesulfonate ion (CF₃SO₃⁻), sulfate ion (SO₄²⁻) and bisulfate ion (HSO₄⁻), and a halide ion such as chloride ion and bromide ion. Specific examples of the protonic acid include a fluoro complex acid such as tetrafluoroboric acid and hexafluorophosphoric acid; a sulfonic acid such as sulfuric acid and trifluoromethanesulfonic acid; and a hydrogen halide such as hydrogen chloride. The protonic acid may form a complex with an ether such as dimethyl ether and diethyl ether. Examples of the protonic acid in the form of a complex include a tetrafluoroboric acid-dimethyl ether complex, a tetrafluoroboric acid-diethyl ether complex, and a hexafluorophosphoric acid-diethyl ether complex.

In view of a high yield of the cationic tris(nitrile) complex (4), a tetrafluoroboric acid-diethyl ether complex or a trifluoromethanesulfonic acid is preferred.

As the protonic acid for use in production method 2, a fluoro complex acid produced in a reaction system by reacting a fluoro complex anion-containing salt with a strong acid may also be used. In this case, examples of the fluoro complex anion-containing salt that can be used include ammonium tetrafluoroborate, lithium tetrafluoroborate, sodium tetrafluoroborate, potassium tetrafluoroborate, ammonium hexafluorophosphate, lithium hexafluorophosphate, sodium hexafluorophosphate, and potassium hexafluorophosphate. Examples of the strong acid that can be used include sulfuric acid, methanesulfonic acid, trifluoromethanesulfonic acid, hydrogen chloride, and hydrogen bromide. Specific examples of the fluoro complex acid that can be produced in a reaction system include tetrafluoroboric acid and hexaluorophosphoric acid. In view of a high cost benefit and a high yield, any one of ammonium tetrafluoroborate, sodium tetrafluoroborate and ammonium hexafluorophosphate is preferably mixed with sulfuric acid and used.

The molar ratio among the ruthenocene derivative (6), the nitrile and the protonic acid used in production method 2 is described below. In view of a high yield of the cationic tris (nitrile) complex (4), 3 mol or more of the nitrile is preferably used per mol of the ruthenocene derivative. In view of a high yield, the nitrile is more preferably used in a solvent amount and, specifically, the nitrile is sill more preferably used in an amount appropriately selected from the range of 5 to 1,000 mol per mol of the ruthenocene derivative. The preferable amount of the protonic acid used varies depending on the kind of the protonic acid. For example, in the case where the protonic acid is a monobasic acid, in view of a high yield, 1 mol or more of the protonic acid is preferably used per mol of the ruthenocene derivative, and in the case of a dibasic acid, 0.5 mol or more of the protonic acid is preferably used per mol of the ruthenocene derivative. In the case where a mixture of a fluoro complex anion-containing salt and a strong acid is used as the protonic acid, 1 mol or more of the fluoro complex anion-containing salt and from 0.5 to 2.0 mol of the strong acid are appropriately used per mol of the ruthenocene derivative, whereby the cationic tris(nitrile) complex (4) can be efficiently obtained.

For the reason that the yield of the cationic tris(nitrile) complex (4) is high, production method 2 is preferably performed in an inert gas. Specific examples of the inert gas include helium, neon, argon, krypton, xenon, and nitrogen gas, with argon or nitrogen gas being preferred.

For the reason that the yield of the cationic tris(nitrile) complex (4) is high, production method 2 is preferably performed under the conditions using an excessive amount of nitrile as a solvent. In addition, production method 2 can also be performed in an organic solvent. Specific examples of the organic solvent include an aliphatic hydrocarbon such as pentane, hexane, heptane, octane, cyclohexane, methylcyclohexane, ethylcyclohexane and petroleum ether, an ether such as diethyl ether, diisopropyl ether, dibutyl ether, cyclopentyl methyl ether, cyclopentyl ethyl ether, tetrahydrofuran, dioxane and 1,2-dimethoxyethane, a ketone such as acetone, methyl ethyl ketone, 3-pentanone, cyclopentanone and cyclohexanone, and an alcohol such as methanol, ethanol, propanol, isopropanol, tert-butanol and ethylene glycol. Of these organic solvents, one kind may be used alone, or a plurality of kinds may be mixed in an arbitrary ratio and used. In view of a high yield of the cationic tris(nitrile) complex (4), diethyl ether, tetrahydrofuran, acetone and methanol are preferred as the organic solvent.

In production method 2, the reaction temperature and the reaction time are not particularly limited, and general conditions employed by one skilled in the art when producing a metal complex may be used. As a specific example, a reaction temperature appropriately selected from a temperature range of −80° C. to 150° C. and a reaction time appropriately selected from the range of 10 minutes to 120 hours are employed, whereby the cationic tris(nitrile) complex (4) can be efficiently produced.

The cationic tris(nitrile) complex (4) produced by production method 2 may be purified by appropriately selecting and using a general purification method employed by one skilled in the art when purifying a metal complex. The purification method specifically includes filtration, extraction, centrifugation, decantation, crystallization, etc.

The ruthenium complex (1) can also be produced by continuously performing production method 2 and production method 1. In this case, the cationic tris(nitrile) complex (4) produced by production method 2 may be used as a raw material for production in production method 1 without purifying it, or the cationic tris(nitrile) complex (4) that is purified by appropriately selecting and using a general purification method employed by one skilled in the art when purifying a metal complex may be used as a raw material for production in production method 1.

In addition, the ruthenium complex (1a) of the present invention can also be produced in the same manner as the ruthenium complex (1) by continuously performing production method 2 and production method 1.

Definitions of $R^8$, $R^9$ and n in formula (2) are described.

The alkyl group having a carbon number of 1 to 6 represented by $R^8$ and $R^9$ may be any of a linear alkyl group, a branched alkyl group and a cyclic alkyl group, and specific examples thereof include a methyl group, an ethyl group, a propyl group, an isopropyl group, a cyclopropyl group, a butyl group, an isobutyl group, a sec-butyl group, a tert-butyl group, a cyclobutyl group, a pentyl group, a 1-methylbutyl group, a 2-methylbutyl group, an isopentyl group, a neopentyl group, a tert-pentyl group, a cyclopentyl group, a cyclobutylmethyl group, a hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a cyclohexyl group, a cyclopentylmethyl group, a 1-cyclobutylethyl group, and a 2-cyclobutylethyl group. From the standpoint that the ruthenium complex (2) of the present invention has vapor pressure and thermal stability suitable as a CVD material or an ALD material, those members are preferably an alkyl group having a carbon number of 1 to 4, more preferably a methyl group.

n is an integer of 0 to 2 and from the standpoint that the ruthenium complex (2) of the present invention has vapor pressure suitable as a CVD material or an ALD material, n is preferably 0.

Specific examples of the ruthenium complex (2) of the present invention are shown in Tables 3 and 4. Here, Me, Et, Pr, $^i$Pr, Bu, $^t$Bu, Pe and Hx stand for a methyl group, an ethyl group, a propyl group, an isopropyl group, a butyl group, a tert-butyl group, a pentyl group and a hexyl group, respectively.

[Table 8]

TABLE 3

| (2) Compound No. | $R^8$ | $R^9$ | n |
|---|---|---|---|
| 2-1 | Me | Me | 0 |
| 2-2 | Me | Et | 0 |
| 2-3 | Et | Et | 0 |
| 2-4 | Et | Pr | 0 |
| 2-5 | Pr | Pr | 0 |
| 2-6 | Pr | Bu | 0 |
| 2-7 | Bu | Bu | 0 |
| 2-8 | Bu | Pe | 0 |
| 2-9 | Pe | Pe | 0 |
| 2-10 | Pe | Hx | 0 |
| 2-11 | Hx | Hx | 0 |
| 2-12 | Me | $^i$Pr | 0 |
| 2-13 | Me | $^t$Bu | 0 |
| 2-14 | Et | $^i$Pr | 0 |
| 2-15 | $^i$Pr | $^i$Pr | 0 |
| 2-16 | $^i$Pr | $^t$Bu | 0 |
| 2-17 | $^t$Bu | $^t$Bu | 0 |
| 2-18 | Me | Me | 1 |
| 2-19 | Me | Et | 1 |
| 2-20 | Et | Et | 1 |
| 2-21 | Et | Pr | 1 |
| 2-22 | Pr | Pr | 1 |
| 2-23 | Pr | Bu | 1 |
| 2-24 | Bu | Bu | 1 |
| 2-25 | Bu | Pe | 1 |
| 2-26 | Pe | Pe | 1 |
| 2-27 | Pe | Hx | 1 |
| 2-28 | Hx | Hx | 1 |
| 2-29 | Me | $^i$Pr | 1 |
| 2-30 | Me | $^t$Bu | 1 |
| 2-31 | Et | $^i$Pr | 1 |
| 2-32 | $^i$Pr | $^i$Pr | 1 |
| 2-33 | $^i$Pr | $^t$Bu | 1 |
| 2-34 | $^t$Bu | $^t$Bu | 1 |
| 2-35 | Me | Me | 2 |
| 2-36 | Me | Et | 2 |
| 2-37 | Et | Et | 2 |

[Table 9]

TABLE 4

| (2) Compound No. | $R^8$ | $R^9$ | n |
|---|---|---|---|
| 2-38 | Et | Pr | 2 |
| 2-39 | Pr | Pr | 2 |
| 2-40 | Pr | Bu | 2 |
| 2-41 | Bu | Bu | 2 |
| 2-42 | Bu | Pe | 2 |
| 2-43 | Pe | Pe | 2 |
| 2-44 | Pe | Hx | 2 |
| 2-45 | Hx | Hx | 2 |
| 2-46 | Me | $^i$Pr | 2 |

TABLE 4-continued

| (2) Compound No. | R⁸ | R⁹ | n |
|---|---|---|---|
| 2-47 | Me | ᵗBu | 2 |
| 2-48 | Et | ⁱPr | 2 |
| 2-49 | ⁱPr | ⁱPr | 2 |
| 2-50 | ⁱPr | ᵗBu | 2 |
| 2-51 | ᵗBu | ᵗBu | 2 |

Among those exemplified in Tables 3 and 4, in view of having vapor pressure and thermal stability suitable as a CVD material or an ALD material, (1-5-η⁵-cyclooctadienyl)(η⁵-2,5-dimethylpyrrolyl)ruthenium (2-1), (1-5-η⁵-cyclooctadienyl)(η⁵-2-ethyl-5-methylpyrrolyl)ruthenium (2-2), (1-5-η⁵-cyclooctadienyl)(η⁵-2,5-diethylpyrrolyl)ruthenium (2-3), (1-5-η⁵-cyclooctadienyl)(η⁵-2-ethyl-5-propylpyrrolyl)ruthenium (2-4), (1-5-η⁵-cyclooctadienyl)(η⁵-2,5-dipropylpyrrolyl)ruthenium (2-5), (1-5-η⁵-cyclooctadienyl)(η⁵-2-butyl-5-propylpyrrolyl)ruthenium (2-6), (1-5-η⁵-cyclooctadienyl)(η⁵-2,5-dibutylpyrrolyl)ruthenium (2-7), (1-5-η⁵-cyclooctadienyl)(η⁵-2-butyl-5-pentylpyrrolyl)ruthenium (2-8), (1-5-η⁵-cyclooctadienyl)(η⁵-2,5-dipentylpyrrolyl)ruthenium (2-9), (1-5-η⁵-cyclooctadienyl)(η⁵-2-hexyl-5-pentylpyrrolyl)ruthenium (2-10), (1-5-η⁵-cyclooctadienyl)(η⁵-2,5-dihexylpyrrolyl)ruthenium (2-11), (1-5-η⁵-cyclooctadienyl)(η⁵-2-methyl-5-isopropylpyrrolyl)ruthenium (2-12), (1-5-η⁵-cyclooctadienyl)(η⁵-2-tert-butyl-5-methyl)ruthenium (2-13), (1-5-η⁵-cyclooctadienyl)(η⁵-2-ethyl-5-isopropylpyrrolyl)ruthenium (2-14), (1-5-η⁵-cyclooctadienyl)(η⁵-2,5-di(isopropyl)pyrrolyl)ruthenium (2-15), (1-5-η⁵-cyclooctadienyl)(η⁵-2-tert-butyl-5-isopropylpyrrolyl)ruthenium (2-16) and (1-5-η⁵-cyclooctadienyl)(η⁵-2,5-di(tert-butyl)pyrrolyl)ruthenium (2-17) are preferred; (1-5-η⁵-cyclooctadienyl)(η⁵-2,5-dimethylpyrrolyl)ruthenium (2-1), (1-5-η⁵-cyclooctadienyl)(η⁵-2-ethyl-5-methylpyrrolyl)ruthenium (2-2), (1-5-η⁵-cyclooctadienyl)(η⁵-2,5-diethylpyrrolyl)ruthenium (2-3), (1-5-η⁵-cyclooctadienyl)(η⁵-2-ethyl-5-propylpyrrolyl)ruthenium (2-4), (1-5-η⁵-cyclooctadienyl)(η⁵-2,5-dipropylpyrrolyl)ruthenium (2-5), (1-5-η⁵-cyclooctadienyl)(η⁵-2-butyl-5-propylpyrrolyl)ruthenium (2-6), (1-5-η⁵-cyclooctadienyl)(η⁵-2,5-dibutylpyrrolyl)ruthenium (2-7), (1-5-η⁵-cyclooctadienyl)(η⁵-2-methyl-5-isopropylpyrrolyl)ruthenium (2-12), (1-5-η⁵-cyclooctadienyl)(η⁵-2-tert-butyl-5-methyl)ruthenium (2-13), (1-5-η⁵-cyclooctadienyl)(η⁵-2-ethyl-5-isopropylpyrrolyl)ruthenium (2-14), (1-5-η⁵-cyclooctadienyl)(η⁵-2,5-di(isopropyl)pyrrolyl)ruthenium (2-15), (1-5-η⁵-cyclooctadienyl)(η⁵-2-tert-butyl-5-isopropylpyrrolyl)ruthenium (2-16) and (1-5-η⁵-cyclooctadienyl)(η⁵-2,5-di(tert-butyl)pyrrolyl)ruthenium (2-17) are more preferred; and (1-5-η⁵-cyclooctadienyl)(η⁵-2,5-dimethylpyrrolyl)ruthenium (2-1) is still more preferred.

The production method of the ruthenium complex (2) of the present invention is described below.

The ruthenium complex (2) of the present invention can be produced by the following production method 3 or production method 5.

Production method 3 is a method of reacting a cationic bis(cyclooctadienyl) complex (8) with a substituted pyrrole (9) in the presence of a base to produce the ruthenium complex (2) of the present invention.

Production Method 3:

[Chem. 11]

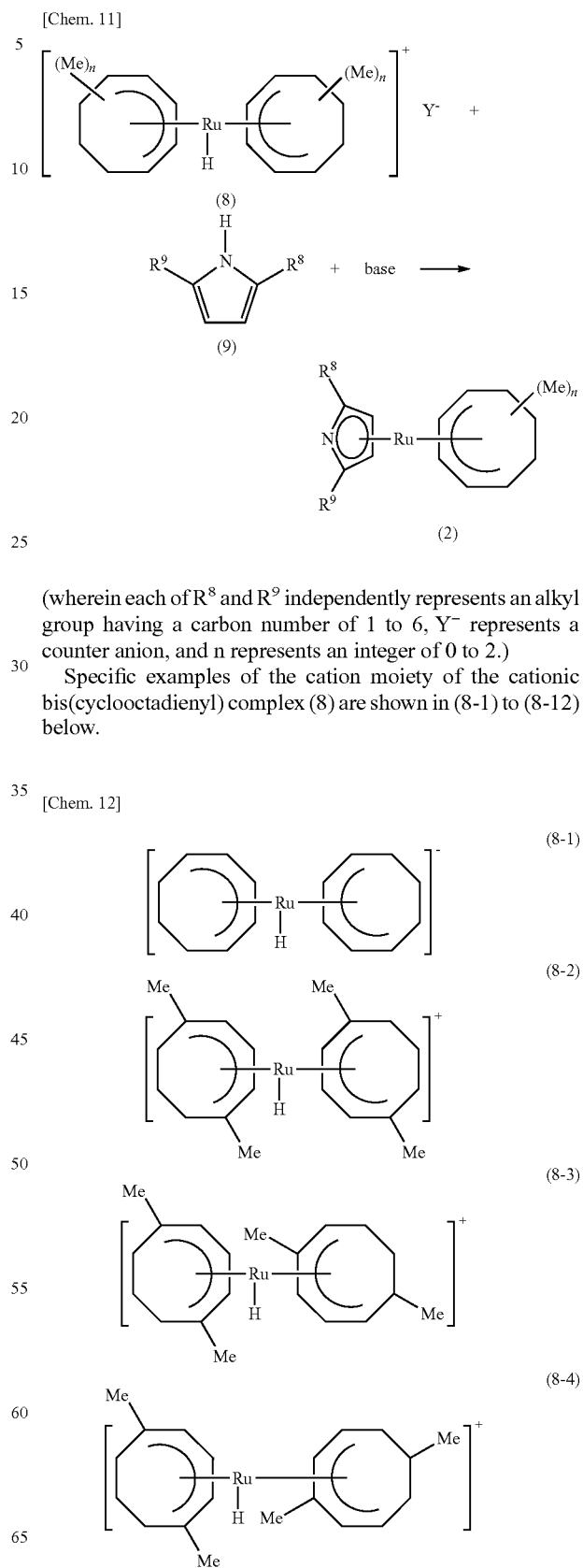

(wherein each of R⁸ and R⁹ independently represents an alkyl group having a carbon number of 1 to 6, Y⁻ represents a counter anion, and n represents an integer of 0 to 2.)

Specific examples of the cation moiety of the cationic bis(cyclooctadienyl) complex (8) are shown in (8-1) to (8-12) below.

[Chem. 12]

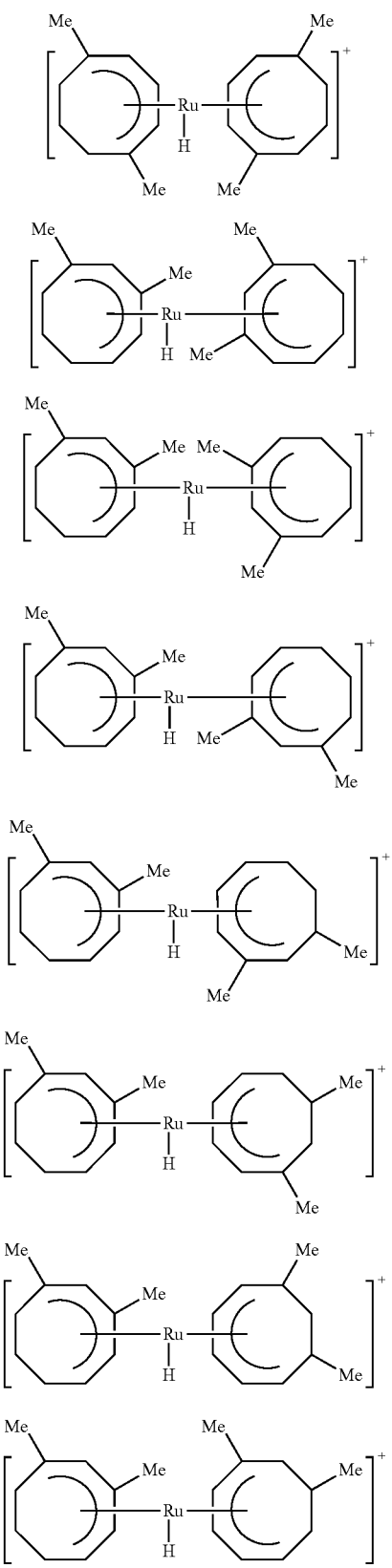

Among those exemplified in (8-1) to (8-12), in view of having vapor pressure suitable as a CVD material or an ALD material, [bis(1-5-η$^5$-cyclooctadienyl)(hydride)ruthenium (IV)] ([RuH(η$^5$-C$_8$H$_{11}$)$_2$]) (8-1) is preferred.

Examples of the counter anion Y$^-$ in formula (8) include those generally used as a counter anion of a cationic metal complex. Specific examples thereof include a fluoro complex anion such as tetrafluoroborate ion (BF$_4^-$), hexafluorophosphate ion (PF$_6^-$), hexafluoroantimonate ion (SbF$_6^-$) and tetrafluoroaluminate ion (AlF$_4^-$), a monovalent sulfonate ion such as trifluoromethanesulfonate ion (CF$_3$SO$_3^-$), methanesulfonate ion (MeSO$_3^-$) and methylsulfate ion (MeSO$_4^-$), a halide ion such as chloride ion and bromide ion, a counter anion of a monobasic acid, such as nitrate ion (NO$_3^-$), perchlorate ion (ClO$_4^-$), tetrachloroaluminate ion (AlCl$_4^-$) and bis(trifluoromethanesulfonyl)amide ion ((CF$_3$SO$_2$)$_2$N$^-$), a counter anion of a polybasic acid, such as sulfate ion (SO$_4^{2-}$), hydrogen sulfate ion (HSO$_4^-$), phosphate ion (PO$_4^{3-}$), monohydrogen phosphate ion (HPO$_4^{2-}$), dihydrogen phosphate ion (H$_2$PO$_4^-$), dimethylphosphate ion ((MeO)$_2$PO$_4^-$) and diethylphosphate ion ((EtO)$_2$PO$_4^-$), and a derivative thereof. In view of a high yield of the ruthenium complex (2), the counter anion Y$^-$ is preferably a fluoro complex anion such as BF$_4^-$ and PF$_6^-$, or a monovalent sulfonate ion such as CF$_3$SO$_3^-$ and MeSO$_3^-$, more preferably BF$_4^-$.

Specific preferred examples of the cationic bis(cyclooctadienyl) complex (8) include [bis(1-5-η$^5$-cyclooctadienyl)(hydride)ruthenium(IV)][tetrafluoroborate] ([RuH(η$^5$-C$_8$H$_{11}$)$_2$][BF$_4$]), [(bis(1-5-η$^5$-cyclo-octadienyl)(hydride)ruthenium(IV))][hexafluorophosphate] ([RuH(η$^5$-C$_8$H$_{11}$)$_2$][PF$_6$]), [(bis(1-5-η$^5$-cyclooctadienyl)(hydride)ruthenium(IV))][trifluoromethanesulfonate] ([RuH(η$^5$-C$_8$H$_{11}$)$_2$][CF$_3$SO$_3$]), and [(bis(1-5-η$^5$-cyclooctadienyl)(hydride)ruthenium(IV))][methanesulfonate] ([RuH(η$^5$-C$_8$H$_{11}$)$_2$][MeSO$_3$]). In view of a high yield of the ruthenium complex (2), [bis(1-5-η$^5$-cyclooctadienyl)(hydride)ruthenium(IV)][tetrafluoroborate] ([RuH(η$^5$-C$_8$H$_{11}$)$_2$][BF$_4$]), etc. are preferred.

Specific examples of the substituted pyrrole (9) include 2,5-dimethylpyrrole, 2-ethyl-5-methylpyrrole, 2,5-diethylpyrrole, 2-ethyl-5-propylpyrrole, 2,5-dipropylpyrrole, 2-butyl-5-propylpyrrole, 2,5-dibutylpyrrole, 2-butyl-5-pentylpyrrole, 2,5-dipentylpyrrole, 2-hexyl-5-pentylpyrrole, 2,5-dihexylpyrrole, 2-methyl-5-isopropylpyrrole, 2-tert-butyl-5-methylpyrrole, 2-ethyl-5-isopropylpyrrole, 2,5-di(isopropyl)pyrrole, 2-tert-butyl-5-isopropylpyrrole, and 2,5-di(tert-butyl)pyrrole. From the standpoint that the ruthenium complex (2) has vapor pressure suitable as a CVD material or an ALD material, 2,5-dimethylpyrrole, 2-ethyl-5-methylpyrrole, 2,5-diethylpyrrole, 2-ethyl-5-propylpyrrole, 2,5-dipropylpyrrole, 2-butyl-5-propylpyrrole, 2,5-dibutylpyrrole, 2-methyl-5-isopropylpyrrole, 2-tert-butyl-5-methylpyrrole, 2-ethyl-5-isopropylpyrrole, 2,5-di(isopropyl)pyrrole, 2-tert-butyl-5-isopropylpyrrole and 2,5-di(tert-butyl)pyrrole are preferred, and 2,5-dimethylpyrrole is more preferred.

The base that can be used in production method 3 includes an inorganic base and an organic base. Examples of the inorganic base include an alkali metal carbonate such as lithium carbonate, sodium carbonate and potassium carbonate, an alkali metal bicarbonate such as lithium bicarbonate, sodium bicarbonate and potassium bicarbonate, a Group 2 metal carbonate such as magnesium carbonate, calcium carbonate and strontium carbonate, a typical metal hydroxide such as lithium hydroxide, sodium hydroxide, potassium hydroxide, magnesium hydroxide, calcium hydroxide and strontium hydroxide, a typical metal hydride such as lithium hydride, sodium hydride, potassium hydride, magnesium hydride, calcium hydride and aluminum hydride, a typical metal hydride complex compound such as sodium borohydride and aluminum lithium hydride, and an alkali metal amide such as lithium amide, sodium amide and lithium dialkylamide. Examples of the organic base include a secondary or tertiary amine such as diethylamine, triethylamine, diethylisopropylamine and tributylamine, a cyclic aliphatic amine such as pyrrolidine, piperidine, piperazine and 1,4-diazabicyclooctane, and an aromatic amine such as pyridine. In view of a high yield of the ruthenium complex (2), the base is preferably a secondary or tertiary amine or pyridine, more preferably a secondary or tertiary amine, still more preferably triethylamine.

For the reason that the yield of the ruthenium complex (2) is high, production method 3 is preferably performed in an inert gas. Specific examples of the inert gas include helium, neon, argon, krypton, xenon, and nitrogen gas, with argon or nitrogen gas being preferred.

For the reason that the yield of the ruthenium complex (2) is high, production method 3 is preferably performed in an organic solvent. In the case of performing production method 3 in an organic solvent, specific examples of the organic solvent include an aliphatic hydrocarbon such as pentane, hexane, heptane, octane, cyclohexane, methylcyclohexane, ethylcyclohexane and petroleum ether, a halogen-based aliphatic hydrocarbon such as chloroform, dichloromethane, dibromomethane, 1,1-dichloroethane, 1,2-dichloroethane and 1,1,1-trichloroethane, an ether such as diethyl ether, diisopropyl ether, dibutyl ether, cyclopentyl methyl ether, cyclopentyl ethyl ether, methyl-tert-butyl ether, tetrahydrofuran, dioxane and 1,2-dimethoxyethane, a ketone such as acetone, methyl ethyl ketone, 3-pentanone, cyclopentanone and cyclohexanone, and an alcohol such as methanol, ethanol, propanol, isopropanol, tert-butanol and ethylene glycol. Of these organic solvents, one kind may be used alone, or a plurality of kinds may be mixed in an arbitrary ratio and used. In view of a high yield of the ruthenium complex (2), as the organic solvent, chloroform, dichloromethane, cyclopentyl methyl ether, methyl-tert-butyl ether, diethyl ether, tetrahydrofuran, acetone, methanol and hexane are preferred, and chloroform, dichloromethane, cyclopentyl methyl ether, methyl-tert-butyl ether, diethyl ether and tetrahydrofuran are more preferred.

The method for obtaining the substituted pyrrole (9) includes the production methods described, for example, in Journal of the American Chemical Society, Vol. 77, page 3340 (1955), and Organic Letters, Vol. 15, page 1436 (2013), other than the purchase of a commercial product.

The molar ratio among the cationic bis(cyclooctadienyl) complex (8), the substituted pyrrole (9) and the base when performing production method 3 is described below. Preferably, 1 mol or more of the substituted pyrrole (9) and the base are used per mol of the cationic bis(cyclooctadienyl) complex (8), whereby the ruthenium complex (2) can be efficiently produced.

In production method 3, the reaction temperature and the reaction time are not particularly limited, and general conditions employed by one skilled in the art when producing a metal complex may be used. As a specific example, a reaction temperature appropriately selected from a temperature range of −80° C. to 120° C. and a reaction time appropriately selected from the range of 10 minutes to 120 hours are employed, whereby the ruthenium complex (2) can be efficiently produced. The ruthenium complex (2) produced by production method 3 may be purified by appropriately selecting and using a general purification method employed by one skilled in the art when purifying a metal complex. The purification method specifically includes filtration, extraction, centrifugation, decantation, distillation, sublimation, crystallization, column chromatography, etc.

The cationic bis(cyclooctadienyl) complex (8) as a raw material of production method 3 can be produced according to production method 4 described in Organometallics, Vol. 10, page 455 (1991). Production method 4 is a method of reacting a (cyclooctadiene)(cyclooctatriene) complex (15) with a protonic acid H⁺Y⁻ to produce a cationic bis(cyclooctadienyl) complex (8).

Production Method 4:

[Chem. 13]

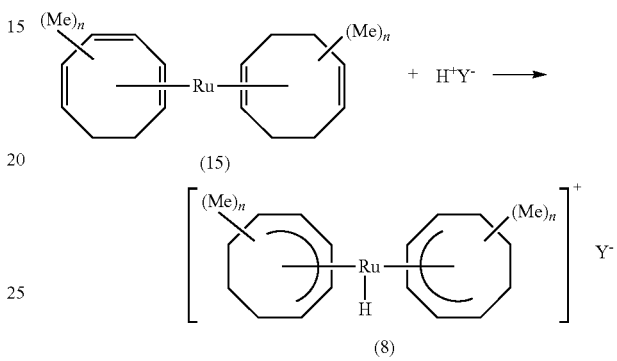

(wherein n represents an integer of 0 to 2, and Y⁻ represents a counter anion.)

The (cyclooctadiene)(cyclooctatriene) complex (15) can be produced according to the method described in Journal of Organometallic Chemistry, Vol. 272, page 179 (1984). Specifically, this is a method of reacting ruthenium chloride with cyclooctadiene in the presence of zinc to produce a (cyclooctadiene)(cyclooctatriene) complex (15).

Specific examples of the cyclooctadiene include 1,5-cyclooctadiene, 1-methyl-1,5-cyclooctadiene, 1,2-dimethyl-1,5-cyclooctadiene, 1,4-dimethyl-1,5-cyclooctadiene, 1,5-dimethyl-1,5-cyclooctadiene, 2,4-dimethyl-1,5-cyclooctadiene, 1,6-dimethyl-1,5-cyclooctadiene, and 3,7-dimethyl-1,5-cyclooctadiene. In view of availability, 1,5-cyclooctadiene and 1,5-dimethyl-1,5-cyclooctadiene are preferred, and 1,5-cyclooctadiene is more preferred.

The method for obtaining the cyclooctadiene include the methods described, for example, in Journal of the American Chemical Society, Vol. 116, page 2889 (1994), Heterocycles, Vol. 77, page 927 (2009), and JP-A-11-209314, other than the purchase of a commercial product.

Specific preferred examples of the (cyclooctadiene)(cyclooctatriene) complex (15) include ($\eta^4$-1,5-cyclooctadiene)($\eta^6$-1,3,5-cyclooctatriene)ruthenium (Ru($\eta^4$-C$_8$H$_{12}$)($\eta^6$-C$_8$H$_{10}$)).

Examples of the counter anion Y⁻ of the protonic acid that can be used in production method 4 include those generally used as a counter anion of a cationic metal complex. Specific examples thereof include a fluoro complex anion such as tetrafluoroborate ion (BF$_4^-$), hexafluorophosphate ion (PF$_6^-$), hexafluoroantimonate ion (SbF$_6^-$) and tetrafluoroaluminate ion (AlF$_4^-$), a monovalent sulfonate ion such as trifluoromethanesulfonate ion (CF$_3$SO$_3^-$), methanesulfonate ion (MeSO$_3^-$) and methylsulfate ion (MeSO$_4^-$), a halide ion such as chloride ion and bromide ion, a counter anion of a monobasic acid, such as nitrate ion (NO$_3^-$), perchlorate ion (ClO$_4^-$), tetrachloroaluminate ion (AlCl$_4^-$) and bis(trifluoromethanesulfonyl)amide ion ((CF$_3$SO$_2$)$_2$N), a counter anion of a polybasic acid, such as sulfate ion ($SO_4^{2-}$), hydrogen sulfate ion ($HSO_4^-$), phosphate ion ($PO_4^{3-}$), monohydrogen phosphate ion ($HPO_4^{2-}$), dihydrogen phosphate ion ($H_2PO_4^-$), dimethylphosphate ion (($MeO)_2PO_4^-$) and diethylphosphate ion (($EtO)_2PO_4^-$), and a derivative thereof. In view of a high yield of the cationic bis(cyclooctadienyl) complex (8), the counter anion $Y^-$ is preferably a fluoro complex anion such as $BF_4^-$ and $PF_6^-$, or a monovalent sulfonate ion such as $CF_3SO_3^-$ and $MeSO_3^-$, more preferably $BF_4^-$.

Specific examples of the protonic acid include a fluoro complex acid such as tetrafluoroboric acid and hexafluorophosphoric acid; a sulfonic acid such as sulfuric acid and trifluoromethanesulfonic acid; and a hydrogen halide such as hydrogen chloride. The protonic acid may form a complex with an ether such as dimethyl ether and diethyl ether. Examples of the protonic acid in the form of a complex include a tetrafluoroboric acid-dimethyl ether complex, a tetrafluoroboric acid-diethyl ether complex, and a hexafluorophosphoric acid-diethyl ether complex. In view of a high yield of the cationic bis(cyclooctadienyl) complex (8), a tetrafluoroboric acid-diethyl ether complex, etc. are preferred.

As the protonic acid for use in production method 4, a fluoro complex acid produced in a reaction system by reacting a fluoro complex anion-containing salt with a strong acid may also be used. In this case, examples of the fluoro complex anion-containing salt that can be used include ammonium tetrafluoroborate, lithium tetrafluoroborate, sodium tetrafluoroborate, potassium tetrafluoroborate, ammonium hexafluorophosphate, lithium hexafluorophosphate, sodium hexafluorophosphate, and potassium hexafluorophosphate. Examples of the strong acid that can be used include sulfuric acid, methanesulfonic acid, trifluoromethanesulfonic acid, hydrogen chloride, and hydrogen bromide. Specific examples of the fluoro complex acid that can be produced in a reaction system include tetrafluoroboric acid and hexaluorophosphoric acid. In view of a high cost benefit and a high yield, any one of ammonium tetrafluoroborate, sodium tetrafluoroborate and ammonium hexafluorophosphate is preferably mixed with sulfuric acid and used.

Furthermore, as the protonic acid for use in production method 4, a fluoro complex acid produced in a reaction system by reacting boron trifluoride with a strong acid may also be used. In this case, examples of the strong acid that can be used include sulfuric acid, methanesulfonic acid, trifluoromethanesulfonic acid, hydrogen chloride, and hydrogen bromide.

The molar ratio between the (cyclooctadiene)(cyclooctatriene) complex (15) and the protonic acid used in production method 4 is described below. The preferable amount of the protonic acid used varies depending on the kind of the protonic acid. For example, in the case where the protonic acid is a monobasic acid, in view of a high yield, 1 mol or more of the protonic acid is preferably used per mol of the (cyclooctadiene)(cyclooctatriene) complex (15), and in the case of a dibasic acid, 0.5 mol or more of the protonic acid is preferably used per mol of the (cyclooctadiene)(cyclooctatriene) complex (15). In the case where a mixture of a fluoro complex anion-containing salt and a strong acid is used as the protonic acid, 1 mol or more of the fluoro complex anion-containing salt and from 0.5 to 2.0 mol of the strong acid are appropriately used per mol of the (cyclooctadiene)(cyclooctatriene) complex (15), whereby the cationic bis(cyclooctadienyl) complex (8) can be efficiently obtained.

For the reason that the yield of the cationic bis(cyclooctadienyl) complex (8) is high, production method 4 is preferably performed in an inert gas. Specific examples of the inert gas include helium, neon, argon, krypton, xenon, and nitrogen gas, with argon or nitrogen gas being preferred.

For the reason that the yield of the cationic bis(cyclooctadienyl) complex (8) is high, production method 4 is preferably performed in an organic solvent. In the case of performing production method 4 in an organic solvent, specific examples of the organic solvent include an aliphatic hydrocarbon such as pentane, hexane, heptane, octane, cyclohexane, methylcyclohexane, ethylcyclohexane and petroleum ether, a halogen-based aliphatic hydrocarbon such as chloroform, dichloromethane, dibromomethane, 1,1-dichloroethane, 1,2-dichloroethane and 1,1,1-trichloroethane, an ether such as diethyl ether, diisopropyl ether, dibutyl ether, cyclopentyl methyl ether, cyclopentyl ethyl ether, methyl-tert-butyl ether, tetrahydrofuran, dioxane and 1,2-dimethoxyethane, a ketone such as acetone, methyl ethyl ketone, 3-pentanone, cyclopentanone and cyclohexanone, and an alcohol such as methanol, ethanol, propanol, isopropanol, tert-butanol and ethylene glycol. Of these organic solvents, one kind may be used alone, or a plurality of kinds may be mixed in an arbitrary ratio and used. In view of a high yield of the cationic bis(cyclooctadienyl) complex (8), chloroform, dichloromethane, cyclopentyl methyl ether, methyl-tert-butyl ether, diethyl ether, tetrahydrofuran, etc. are preferred. In production method 4, the reaction temperature and the reaction time are not particularly limited, and general conditions employed by one skilled in the art when producing a metal complex may be used. As a specific example, a reaction temperature appropriately selected from a temperature range of $-80°$ C. to $150°$ C. and a reaction time appropriately selected from the range of 10 minutes to 120 hours are employed, whereby the cationic bis(cyclooctadienyl) complex (8) can be efficiently produced.

The cationic bis(cyclooctadienyl) complex (8) produced by production method 4 may be purified by appropriately selecting and using a general purification method employed by one skilled in the art when purifying a metal complex. The purification method specifically includes filtration, extraction, centrifugation, decantation, distillation, crystallization, etc.

The ruthenium complex (2) can also be produced by production method 5 of continuously performing production method 4 and production method 3. In this case, the cationic bis(cyclooctadienyl) complex (8) produced by production method 4 may be used as a raw material for production in production method 3 without purifying it, or the cationic bis(cyclooctadienyl) complex (8) that is purified by appropriately selecting and using a general purification method employed by one skilled in the art when purifying a metal complex may be used as a raw material for production in production method 3. Examples of the purification method include filtration, extraction, centrifugation, decantation, and crystallization.

Definitions of $R^{10}$, $R^{11}$, $R^{12}$, $R^{13}$, $R^{14}$, $R^{15}$, $R^{16}$, $R^{17}$ and $R^{18}$ in formula (3) are described below.

The alkyl group having a carbon number of 1 to 6 represented by $R^{10}$, $R^{11}$, $R^{12}$, $R^{13}$ and $R^{14}$ may be any of a linear alkyl group, a branched alkyl group and a cyclic alkyl group, and specific examples thereof include a methyl group, an ethyl group, a propyl group, an isopropyl group, a cyclopropyl group, a butyl group, an isobutyl group, a sec-butyl group, a tert-butyl group, a cyclobutyl group, a pentyl group, a 1-methylbutyl group, a 2-methylbutyl group, an isopentyl group, a neopentyl group, a tert-pentyl group, a cyclopentyl group, a cyclobutylmethyl group, a hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a cyclohexyl group, a cyclopentylmethyl group, a 1-cyclobutylethyl group, and a 2-cyclobutylethyl group. From the standpoint that the ruthenium complex (3) of the present invention has vapor pressure and thermal stability suitable as a CVD material or an ALD material, preferably, $R^{10}$ is an alkyl group having a carbon number of 1 to 6 and $R^{11}$, $R^{12}$, $R^{13}$ and $R^{14}$ are a hydrogen atom; more preferably, $R^{10}$ is a methyl group or an ethyl group; and still more preferably, $R^{10}$ is an ethyl group.

The alkyl group having a carbon number of 1 to 6 represented by $R^{15}$, $R^{16}$, $R^{17}$ and $R^{18}$ may be any of a linear alkyl group, a branched alkyl group and a cyclic alkyl group, and specific examples thereof include a methyl group, an ethyl group, a propyl group, an isopropyl group, a cyclopropyl group, a butyl group, an isobutyl group, a sec-butyl group, a tert-butyl group, a cyclobutyl group, a pentyl group, a 1-methylbutyl group, a 2-methylbutyl group, an isopentyl group, a neopentyl group, a tert-pentyl group, a cyclopentyl group, a cyclobutylmethyl group, a hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a cyclohexyl group, a cyclopentylmethyl group, a 1-cyclobutylethyl group, and a 2-cyclobutylethyl group. From the standpoint that the ruthenium complex (3) of the present invention has vapor pressure and thermal stability suitable as a CVD material or an ALD material, $R^{15}$, $R^{16}$, $R^{17}$ and $R^{18}$ are preferably a methyl group.

Specific examples of the ruthenium complex (3) of the present invention are shown in Tables 5-1 to 5-10. Here, Me, Et, Pr, $^i$Pr, Bu, $^i$Bu, $^s$Bu, $^t$Bu, Pe, $^c$Pe and Hx stand for a methyl group, an ethyl group, a propyl group, an isopropyl group, a butyl group, an isobutyl group, a sec-butyl group, a tert-butyl group, a pentyl group, a cyclopentyl group and a hexyl group, respectively.

[Table 10]

TABLE 5-1

| (3) Compound No. | $R^{10}$ | $R^{11}$ | $R^{12}$ | $R^{13}$ | $R^{14}$ | $R^{15}$ | $R^{16}$ | $R^{17}$ | $R^{18}$ |
|---|---|---|---|---|---|---|---|---|---|
| 3-1 | H | H | H | H | H | H | H | H | Me |
| 3-2 | Me | H | H | H | H | H | H | H | Me |
| 3-3 | Et | H | H | H | H | H | H | H | Me |
| 3-4 | Pr | H | H | H | H | H | H | H | Me |
| 3-5 | $^i$Pr | H | H | H | H | H | H | H | Me |
| 3-6 | Bu | H | H | H | H | H | H | H | Me |
| 3-7 | $^i$Bu | H | H | H | H | H | H | H | Me |
| 3-8 | $^s$Bu | H | H | H | H | H | H | H | Me |
| 3-9 | $^t$Bu | H | H | H | H | H | H | H | Me |
| 3-10 | Pe | H | H | H | H | H | H | H | Me |
| 3-11 | $^c$Pe | H | H | H | H | H | H | H | Me |
| 3-12 | Hx | H | H | H | H | H | H | H | Me |
| 3-13 | Me | Me | H | H | H | H | H | H | Me |
| 3-14 | Me | H | Me | H | H | H | H | H | Me |
| 3-15 | $^t$Bu | H | $^t$Bu | H | H | H | H | H | Me |
| 3-16 | Me | Me | Me | H | H | H | H | H | Me |
| 3-17 | Me | Me | H | Me | H | H | H | H | Me |
| 3-18 | $^i$Pr | $^i$Pr | H | $^i$Pr | H | H | H | H | Me |
| 3-19 | Me | Me | Me | Me | H | H | H | H | Me |
| 3-20 | Et | Me | Me | Me | Me | H | H | H | Me |
| 3-21 | Pr | Me | Me | Me | Me | H | H | H | Me |
| 3-22 | H | H | H | H | H | H | H | H | Bu |
| 3-23 | Me | H | H | H | H | H | H | H | Bu |
| 3-24 | Et | H | H | H | H | H | H | H | Bu |
| 3-25 | Pr | H | H | H | H | H | H | H | Bu |

TABLE 5-1-continued

| (3) Compound No. | $R^{10}$ | $R^{11}$ | $R^{12}$ | $R^{13}$ | $R^{14}$ | $R^{15}$ | $R^{16}$ | $R^{17}$ | $R^{18}$ |
|---|---|---|---|---|---|---|---|---|---|
| 3-26 | $^i$Pr | H | H | H | H | H | H | H | Bu |
| 3-27 | Bu | H | H | H | H | H | H | H | Bu |
| 3-28 | $^i$Bu | H | H | H | H | H | H | H | Bu |
| 3-29 | $^s$Bu | H | H | H | H | H | H | H | Bu |
| 3-30 | $^t$Bu | H | H | H | H | H | H | H | Bu |
| 3-31 | Pe | H | H | H | H | H | H | H | Bu |
| 3-32 | $^c$Pe | H | H | H | H | H | H | H | Bu |
| 3-33 | Hx | H | H | H | H | H | H | H | Bu |
| 3-34 | Me | Me | H | H | H | H | H | H | Bu |
| 3-35 | Me | H | Me | H | H | H | H | H | Bu |
| 3-36 | $^t$Bu | H | $^t$Bu | H | H | H | H | H | Bu |
| 3-37 | Me | Me | Me | H | H | H | H | H | Bu |
| 3-38 | Me | Me | H | Me | H | H | H | H | Bu |

[Table 11]

TABLE 5-2

| (3) Compound No. | $R^{10}$ | $R^{11}$ | $R^{12}$ | $R^{13}$ | $R^{14}$ | $R^{15}$ | $R^{16}$ | $R^{17}$ | $R^{18}$ |
|---|---|---|---|---|---|---|---|---|---|
| 3-39 | $^i$Pr | H | $^i$Pr | H | $^i$Pr | H | H | H | Bu |
| 3-40 | Me | Me | Me | Me | H | H | H | H | Bu |
| 3-41 | Me | Me | Me | Me | Me | H | H | H | Bu |
| 3-42 | Et | Me | Me | Me | Me | H | H | H | Bu |
| 3-43 | Pr | Me | Me | Me | Me | H | H | H | Bu |
| 3-44 | H | H | H | H | H | Me | Me | Me | Me |
| 3-45 | Me | H | H | H | H | Me | Me | Me | Me |
| 3-46 | Et | H | H | H | H | Me | Me | Me | Me |
| 3-47 | Pr | H | H | H | H | Me | Me | Me | Me |
| 3-48 | $^i$Pr | H | H | H | H | Me | Me | Me | Me |
| 3-49 | Bu | H | H | H | H | Me | Me | Me | Me |
| 3-50 | $^i$Bu | H | H | H | H | Me | Me | Me | Me |
| 3-51 | $^s$Bu | H | H | H | H | Me | Me | Me | Me |
| 3-52 | $^t$Bu | H | H | H | H | Me | Me | Me | Me |
| 3-53 | Pe | H | H | H | H | Me | Me | Me | Me |
| 3-54 | $^c$Pe | H | H | H | H | Me | Me | Me | Me |
| 3-55 | Hx | H | H | H | H | Me | Me | Me | Me |
| 3-56 | Me | Me | H | H | H | Me | Me | Me | Me |
| 3-57 | Me | H | Me | H | H | Me | Me | Me | Me |
| 3-58 | $^t$Bu | H | $^t$Bu | H | H | Me | Me | Me | Me |
| 3-59 | Me | Me | Me | H | H | Me | Me | Me | Me |
| 3-60 | Me | Me | H | Me | H | Me | Me | Me | Me |
| 3-61 | $^i$Pr | H | $^i$Pr | H | $^i$Pr | Me | Me | Me | Me |
| 3-62 | Me | Me | Me | Me | H | Me | Me | Me | Me |
| 3-63 | Et | Me | Me | Me | Me | Me | Me | Me | Me |
| 3-64 | Pr | Me | Me | Me | Me | Me | Me | Me | Me |
| 3-65 | H | H | H | H | H | Me | Me | Me | Bu |
| 3-66 | Me | H | H | H | H | Me | Me | Me | Bu |
| 3-67 | Et | H | H | H | H | Me | Me | Me | Bu |
| 3-68 | Pr | H | H | H | H | Me | Me | Me | Bu |
| 3-69 | $^i$Pr | H | H | H | H | Me | Me | Me | Bu |
| 3-70 | Bu | H | H | H | H | Me | Me | Me | Bu |
| 3-71 | $^i$Bu | H | H | H | H | Me | Me | Me | Bu |
| 3-72 | $^s$Bu | H | H | H | H | Me | Me | Me | Bu |
| 3-73 | $^t$Bu | H | H | H | H | Me | Me | Me | Bu |
| 3-74 | Pe | H | H | H | H | Me | Me | Me | Bu |
| 3-75 | $^c$Pe | H | H | H | H | Me | Me | Me | Bu |
| 3-76 | Hx | H | H | H | H | Me | Me | Me | Bu |

[Table 12]

TABLE 5-3

| (3) Compound No. | $R^{10}$ | $R^{11}$ | $R^{12}$ | $R^{13}$ | $R^{14}$ | $R^{15}$ | $R^{16}$ | $R^{17}$ | $R^{18}$ |
|---|---|---|---|---|---|---|---|---|---|
| 3-77 | Me | Me | H | H | H | Me | Me | Me | Bu |
| 3-78 | Me | H | Me | H | H | Me | Me | Me | Bu |
| 3-79 | $^t$Bu | H | $^t$Bu | H | H | Me | Me | Me | Bu |

TABLE 5-3-continued (3)

| Compound No. | $R^{10}$ | $R^{11}$ | $R^{12}$ | $R^{13}$ | $R^{14}$ | $R^{15}$ | $R^{16}$ | $R^{17}$ | $R^{18}$ |
|---|---|---|---|---|---|---|---|---|---|
| 3-80 | Me | Me | Me | H | H | Me | Me | Me | Bu |
| 3-81 | Me | Me | H | Me | H | Me | Me | Me | Bu |
| 3-82 | $^i$Pr | H | $^i$Pr | H | $^i$Pr | Me | Me | Me | Bu |
| 3-83 | Me | Me | Me | Me | H | Me | Me | Me | Bu |
| 3-84 | Me | Me | Me | Me | Me | Me | Me | Me | Bu |
| 3-85 | Et | Me | Me | Me | Me | Me | Me | Me | Bu |
| 3-86 | Pr | Me | Me | Me | Me | Me | Me | Me | Bu |
| 3-87 | H | H | H | H | H | Et | Et | Et | Me |
| 3-88 | Me | H | H | H | H | Et | Et | Et | Me |
| 3-89 | Et | H | H | H | H | Et | Et | Et | Me |
| 3-90 | Pr | H | H | H | H | Et | Et | Et | Me |
| 3-91 | $^i$Pr | H | H | H | H | Et | Et | Et | Me |
| 3-92 | Bu | H | H | H | H | Et | Et | Et | Me |
| 3-93 | $^i$Bu | H | H | H | H | Et | Et | Et | Me |
| 3-94 | $^s$Bu | H | H | H | H | Et | Et | Et | Me |
| 3-95 | $^t$Bu | H | H | H | H | Et | Et | Et | Me |
| 3-96 | Pe | H | H | H | H | Et | Et | Et | Me |
| 3-97 | $^c$Pe | H | H | H | H | Et | Et | Et | Me |
| 3-98 | Hx | H | H | H | H | Et | Et | Et | Me |
| 3-99 | Me | Me | H | H | H | Et | Et | Et | Me |
| 3-100 | Me | H | Me | H | H | Et | Et | Et | Me |
| 3-101 | $^t$Bu | H | $^t$Bu | H | H | Et | Et | Et | Me |
| 3-102 | Me | Me | Me | H | H | Et | Et | Et | Me |
| 3-103 | Me | Me | H | Me | H | Et | Et | Et | Me |
| 3-104 | $^i$Pr | H | $^i$Pr | H | $^i$Pr | Et | Et | Et | Me |
| 3-105 | Me | Me | Me | Me | H | Et | Et | Et | Me |
| 3-106 | Et | Me | Me | Me | Me | Et | Et | Et | Me |
| 3-107 | Pr | Me | Me | Me | Me | Et | Et | Et | Me |
| 3-108 | H | H | H | H | H | Et | Et | Et | Bu |
| 3-109 | Me | H | H | H | H | Et | Et | Et | Bu |
| 3-110 | Et | H | H | H | H | Et | Et | Et | Bu |
| 3-111 | Pr | H | H | H | H | Et | Et | Et | Bu |
| 3-112 | $^i$Pr | H | H | H | H | Et | Et | Et | Bu |
| 3-113 | Bu | H | H | H | H | Et | Et | Et | Bu |
| 3-114 | $^i$Bu | H | H | H | H | Et | Et | Et | Bu |

[Table 13]

TABLE 5-4

(3)

| Compound No. | $R^{10}$ | $R^{11}$ | $R^{12}$ | $R^{13}$ | $R^{14}$ | $R^{15}$ | $R^{16}$ | $R^{17}$ | $R^{18}$ |
|---|---|---|---|---|---|---|---|---|---|
| 3-115 | $^s$Bu | H | H | H | H | Et | Et | Et | Bu |
| 3-116 | $^t$Bu | H | H | H | H | Et | Et | Et | Bu |
| 3-117 | Pe | H | H | H | H | Et | Et | Et | Bu |
| 3-118 | $^c$Pe | H | H | H | H | Et | Et | Et | Bu |
| 3-119 | Hx | H | H | H | H | Et | Et | Et | Bu |
| 3-120 | Me | Me | H | H | H | Et | Et | Et | Bu |
| 3-121 | Me | H | Me | H | H | Et | Et | Et | Bu |
| 3-122 | $^t$Bu | H | $^t$Bu | H | H | Et | Et | Et | Bu |
| 3-123 | Me | Me | Me | H | H | Et | Et | Et | Bu |
| 3-124 | Me | Me | H | Me | H | Et | Et | Et | Bu |
| 3-125 | $^i$Pr | H | $^i$Pr | H | $^i$Pr | Et | Et | Et | Bu |
| 3-126 | Me | Me | Me | Me | H | Et | Et | Et | Bu |
| 3-127 | Me | Me | Me | Me | Me | Et | Et | Et | Bu |
| 3-128 | Et | Me | Me | Me | Me | Et | Et | Et | Bu |
| 3-129 | Pr | Me | Me | Me | Me | Et | Et | Et | Bu |
| 3-130 | H | H | H | H | H | Pr | Pr | Pr | Me |
| 3-131 | Me | H | H | H | H | Pr | Pr | Pr | Me |
| 3-132 | Et | H | H | H | H | Pr | Pr | Pr | Me |
| 3-133 | Pr | H | H | H | H | Pr | Pr | Pr | Me |
| 3-134 | $^i$Pr | H | H | H | H | Pr | Pr | Pr | Me |
| 3-135 | Bu | H | H | H | H | Pr | Pr | Pr | Me |
| 3-136 | $^i$Bu | H | H | H | H | Pr | Pr | Pr | Me |
| 3-137 | $^s$Bu | H | H | H | H | Pr | Pr | Pr | Me |
| 3-138 | $^t$Bu | H | H | H | H | Pr | Pr | Pr | Me |
| 3-139 | Pe | H | H | H | H | Pr | Pr | Pr | Me |
| 3-140 | $^c$Pe | H | H | H | H | Pr | Pr | Pr | Me |
| 3-141 | Hx | H | H | H | H | Pr | Pr | Pr | Me |
| 3-142 | Me | Me | H | H | H | Pr | Pr | Pr | Me |
| 3-143 | Me | H | Me | H | H | Pr | Pr | Pr | Me |
| 3-144 | $^t$Bu | H | $^t$Bu | H | H | Pr | Pr | Pr | Me |

TABLE 5-4-continued (3)

| Compound No. | $R^{10}$ | $R^{11}$ | $R^{12}$ | $R^{13}$ | $R^{14}$ | $R^{15}$ | $R^{16}$ | $R^{17}$ | $R^{18}$ |
|---|---|---|---|---|---|---|---|---|---|
| 3-145 | Me | Me | Me | H | H | Pr | Pr | Pr | Me |
| 3-146 | Me | Me | H | Me | H | Pr | Pr | Pr | Me |
| 3-147 | $^i$Pr | H | $^i$Pr | H | $^i$Pr | Pr | Pr | Pr | Me |
| 3-148 | Me | Me | Me | Me | H | Pr | Pr | Pr | Me |
| 3-149 | Et | Me | Me | Me | Me | Pr | Pr | Pr | Me |
| 3-150 | Pr | Me | Me | Me | Me | Pr | Pr | Pr | Me |
| 3-151 | H | H | H | H | H | Pr | Pr | Pr | Bu |
| 3-152 | Me | H | H | H | H | Pr | Pr | Pr | Bu |

[Table 14]

TABLE 5-5

(3)

| Compound No. | $R^{10}$ | $R^{11}$ | $R^{12}$ | $R^{13}$ | $R^{14}$ | $R^{15}$ | $R^{16}$ | $R^{17}$ | $R^{18}$ |
|---|---|---|---|---|---|---|---|---|---|
| 3-153 | Et | H | H | H | H | Pr | Pr | Pr | Bu |
| 3-154 | Pr | H | H | H | H | Pr | Pr | Pr | Bu |
| 3-155 | $^i$Pr | H | H | H | H | Pr | Pr | Pr | Bu |
| 3-156 | Bu | H | H | H | H | Pr | Pr | Pr | Bu |
| 3-157 | $^i$Bu | H | H | H | H | Pr | Pr | Pr | Bu |
| 3-158 | $^s$Bu | H | H | H | H | Pr | Pr | Pr | Bu |
| 3-159 | $^t$Bu | H | H | H | H | Pr | Pr | Pr | Bu |
| 3-160 | Pe | H | H | H | H | Pr | Pr | Pr | Bu |
| 3-161 | $^c$Pe | H | H | H | H | Pr | Pr | Pr | Bu |
| 3-162 | Hx | H | H | H | H | Pr | Pr | Pr | Bu |
| 3-163 | Me | Me | H | H | H | Pr | Pr | Pr | Bu |
| 3-164 | Me | H | Me | H | H | Pr | Pr | Pr | Bu |
| 3-165 | $^t$Bu | Me | $^t$Bu | H | H | Pr | Pr | Pr | Bu |
| 3-166 | Me | Me | Me | H | H | Pr | Pr | Pr | Bu |
| 3-167 | Me | Me | H | Me | H | Pr | Pr | Pr | Bu |
| 3-168 | $^i$Pr | H | $^i$Pr | H | $^i$Pr | Pr | Pr | Pr | Bu |
| 3-169 | Me | Me | Me | Me | H | Pr | Pr | Pr | Bu |
| 3-170 | Me | Me | Me | Me | Me | Pr | Pr | Pr | Bu |
| 3-171 | Et | Me | Me | Me | Me | Pr | Pr | Pr | Bu |
| 3-172 | Pr | Me | Me | Me | Me | Pr | Pr | Pr | Bu |
| 3-173 | H | H | H | H | H | $^i$Pr | $^i$Pr | $^i$Pr | Me |
| 3-174 | Me | H | H | H | H | $^i$Pr | $^i$Pr | $^i$Pr | Me |
| 3-175 | Et | H | H | H | H | $^i$Pr | $^i$Pr | $^i$Pr | Me |
| 3-176 | Pr | H | H | H | H | $^i$Pr | $^i$Pr | $^i$Pr | Me |
| 3-177 | $^i$Pr | H | H | H | H | $^i$Pr | $^i$Pr | $^i$Pr | Me |
| 3-178 | Bu | H | H | H | H | $^i$Pr | $^i$Pr | $^i$Pr | Me |
| 3-179 | $^i$Bu | H | H | H | H | $^i$Pr | $^i$Pr | $^i$Pr | Me |
| 3-180 | $^s$Bu | H | H | H | H | $^i$Pr | $^i$Pr | $^i$Pr | Me |
| 3-181 | $^t$Bu | H | H | H | H | $^i$Pr | $^i$Pr | $^i$Pr | Me |
| 3-182 | Pe | H | H | H | H | $^i$Pr | $^i$Pr | $^i$Pr | Me |
| 3-183 | $^c$Pe | H | H | H | H | $^i$Pr | $^i$Pr | $^i$Pr | Me |
| 3-184 | Hx | H | H | H | H | $^i$Pr | $^i$Pr | $^i$Pr | Me |
| 3-185 | Me | Me | H | H | H | $^i$Pr | $^i$Pr | $^i$Pr | Me |
| 3-186 | Me | H | Me | H | H | $^i$Pr | $^i$Pr | $^i$Pr | Me |
| 3-187 | $^t$Bu | H | $^t$Bu | H | H | $^i$Pr | $^i$Pr | $^i$Pr | Me |
| 3-188 | Me | Me | Me | H | H | $^i$Pr | $^i$Pr | $^i$Pr | Me |
| 3-189 | Me | Me | H | Me | H | $^i$Pr | $^i$Pr | $^i$Pr | Me |
| 3-190 | $^i$Pr | H | $^i$Pr | H | $^i$Pr | $^i$Pr | $^i$Pr | $^i$Pr | Me |

[Table 15]

TABLE 5-6

(3)

| Compound No. | $R^{10}$ | $R^{11}$ | $R^{12}$ | $R^{13}$ | $R^{14}$ | $R^{15}$ | $R^{16}$ | $R^{17}$ | $R^{18}$ |
|---|---|---|---|---|---|---|---|---|---|
| 3-191 | Me | Me | Me | Me | H | $^i$Pr | $^i$Pr | $^i$Pr | Me |
| 3-192 | Et | Me | Me | Me | Me | $^i$Pr | $^i$Pr | $^i$Pr | Me |
| 3-193 | Pr | Me | Me | Me | Me | $^i$Pr | $^i$Pr | $^i$Pr | Me |
| 3-194 | H | H | H | H | H | $^i$Pr | $^i$Pr | $^i$Pr | Bu |
| 3-195 | Me | H | H | H | H | $^i$Pr | $^i$Pr | $^i$Pr | Bu |
| 3-196 | Et | H | H | H | H | $^i$Pr | $^i$Pr | $^i$Pr | Bu |
| 3-197 | Pr | H | H | H | H | $^i$Pr | $^i$Pr | $^i$Pr | Bu |
| 3-198 | $^i$Pr | H | H | H | H | $^i$Pr | $^i$Pr | $^i$Pr | Bu |
| 3-199 | Bu | H | H | H | H | $^i$Pr | $^i$Pr | $^i$Pr | Bu |

TABLE 5-6-continued (3)

| Compound No. | R$^{10}$ | R$^{11}$ | R$^{12}$ | R$^{13}$ | R$^{14}$ | R$^{15}$ | R$^{16}$ | R$^{17}$ | R$^{18}$ |
|---|---|---|---|---|---|---|---|---|---|
| 3-200 | $^i$Bu | H | H | H | H | $^i$Pr | $^i$Pr | $^i$Pr | Bu |
| 3-201 | $^s$Bu | H | H | H | H | $^i$Pr | $^i$Pr | $^i$Pr | Bu |
| 3-202 | $^t$Bu | H | H | H | H | $^i$Pr | $^i$Pr | $^i$Pr | Bu |
| 3-203 | Pe | H | H | H | H | $^i$Pr | $^i$Pr | $^i$Pr | Bu |
| 3-204 | $^c$Pe | H | H | H | H | $^i$Pr | $^i$Pr | $^i$Pr | Bu |
| 3-205 | Hx | H | H | H | H | $^i$Pr | $^i$Pr | $^i$Pr | Bu |
| 3-206 | Me | Me | H | H | H | $^i$Pr | $^i$Pr | $^i$Pr | Bu |
| 3-207 | Me | H | Me | H | H | $^i$Pr | $^i$Pr | $^i$Pr | Bu |
| 3-208 | $^t$Bu | H | $^t$Bu | H | H | $^i$Pr | $^i$Pr | $^i$Pr | Bu |
| 3-209 | Me | Me | Me | H | H | $^i$Pr | $^i$Pr | $^i$Pr | Bu |
| 3-210 | Me | Me | H | Me | H | $^i$Pr | $^i$Pr | $^i$Pr | Bu |
| 3-211 | $^i$Pr | H | $^i$Pr | H | $^i$Pr | $^i$Pr | $^i$Pr | $^i$Pr | Bu |
| 3-212 | Me | Me | Me | Me | H | $^i$Pr | $^i$Pr | $^i$Pr | Bu |
| 3-213 | Me | Me | Me | Me | Me | $^i$Pr | $^i$Pr | $^i$Pr | Bu |
| 3-214 | Et | Me | Me | Me | Me | $^i$Pr | $^i$Pr | $^i$Pr | Bu |
| 3-215 | Pr | Me | Me | Me | Me | $^i$Pr | $^i$Pr | $^i$Pr | Bu |
| 3-216 | H | H | H | H | H | Bu | Bu | Bu | Me |
| 3-217 | Me | H | H | H | H | Bu | Bu | Bu | Me |
| 3-218 | Et | H | H | H | H | Bu | Bu | Bu | Me |
| 3-219 | Pr | H | H | H | H | Bu | Bu | Bu | Me |
| 3-220 | $^i$Pr | H | H | H | H | Bu | Bu | Bu | Me |
| 3-221 | Bu | H | H | H | H | Bu | Bu | Bu | Me |
| 3-222 | $^i$Bu | H | H | H | H | Bu | Bu | Bu | Me |
| 3-223 | $^s$Bu | H | H | H | H | Bu | Bu | Bu | Me |
| 3-224 | $^t$Bu | H | H | H | H | Bu | Bu | Bu | Me |
| 3-225 | Pe | H | H | H | H | Bu | Bu | Bu | Me |
| 3-226 | $^c$Pe | H | H | H | H | Bu | Bu | Bu | Me |
| 3-227 | Hx | H | H | H | H | Bu | Bu | Bu | Me |
| 3-228 | Me | Me | H | H | H | Bu | Bu | Bu | Me |

[Table 16]

TABLE 5-7

(3)

| Compound No. | R$^{10}$ | R$^{11}$ | R$^{12}$ | R$^{13}$ | R$^{14}$ | R$^{15}$ | R$^{16}$ | R$^{17}$ | R$^{18}$ |
|---|---|---|---|---|---|---|---|---|---|
| 3-229 | Me | H | Me | H | H | Bu | Bu | Bu | Me |
| 3-230 | $^t$Bu | H | $^t$Bu | H | H | Bu | Bu | Bu | Me |
| 3-231 | Me | Me | Me | H | H | Bu | Bu | Bu | Me |
| 3-232 | Me | Me | H | Me | H | Bu | Bu | Bu | Me |
| 3-233 | $^i$Pr | H | $^i$Pr | H | $^i$Pr | Bu | Bu | Bu | Me |
| 3-234 | Me | Me | Me | Me | H | Bu | Bu | Bu | Me |
| 3-235 | Et | Me | Me | Me | Me | Bu | Bu | Bu | Me |
| 3-236 | Pr | Me | Me | Me | Me | Bu | Bu | Bu | Me |
| 3-237 | H | H | H | H | H | Bu | Bu | Bu | Bu |
| 3-238 | Me | H | H | H | H | Bu | Bu | Bu | Bu |
| 3-239 | Et | H | H | H | H | Bu | Bu | Bu | Bu |
| 3-240 | Pr | H | H | H | H | Bu | Bu | Bu | Bu |
| 3-241 | $^i$Pr | H | H | H | H | Bu | Bu | Bu | Bu |
| 3-242 | Bu | H | H | H | H | Bu | Bu | Bu | Bu |
| 3-243 | $^i$Bu | H | H | H | H | Bu | Bu | Bu | Bu |
| 3-244 | $^s$Bu | H | H | H | H | Bu | Bu | Bu | Bu |
| 3-245 | $^t$Bu | H | H | H | H | Bu | Bu | Bu | Bu |
| 3-246 | Pe | H | H | H | H | Bu | Bu | Bu | Bu |
| 3-247 | $^c$Pe | H | H | H | H | Bu | Bu | Bu | Bu |
| 3-248 | Hx | H | H | H | H | Bu | Bu | Bu | Bu |
| 3-249 | Me | Me | H | H | H | Bu | Bu | Bu | Bu |
| 3-250 | Me | H | Me | H | H | Bu | Bu | Bu | Bu |
| 3-251 | $^t$Bu | H | $^t$Bu | H | H | Bu | Bu | Bu | Bu |
| 3-252 | Me | Me | Me | H | H | Bu | Bu | Bu | Bu |
| 3-253 | Me | Me | H | Me | H | Bu | Bu | Bu | Bu |
| 3-254 | $^i$Pr | H | $^i$Pr | H | $^i$Pr | Bu | Bu | Bu | Bu |
| 3-255 | Me | Me | Me | Me | H | Bu | Bu | Bu | Bu |
| 3-256 | Me | Me | Me | Me | Me | Bu | Bu | Bu | Bu |
| 3-257 | Et | Me | Me | Me | Me | Bu | Bu | Bu | Bu |
| 3-258 | Pr | Me | Me | Me | Me | Bu | Bu | Bu | Bu |
| 3-259 | H | H | H | H | H | $^t$Bu | $^t$Bu | $^t$Bu | Me |
| 3-260 | Me | H | H | H | H | $^t$Bu | $^t$Bu | $^t$Bu | Me |
| 3-261 | Et | H | H | H | H | $^t$Bu | $^t$Bu | $^t$Bu | Me |
| 3-262 | Pr | H | H | H | H | $^t$Bu | $^t$Bu | $^t$Bu | Me |
| 3-263 | $^i$Pr | H | H | H | H | $^t$Bu | $^t$Bu | $^t$Bu | Me |
| 3-264 | Bu | H | H | H | H | $^t$Bu | $^t$Bu | $^t$Bu | Me |

TABLE 5-7-continued (3)

| Compound No. | R$^{10}$ | R$^{11}$ | R$^{12}$ | R$^{13}$ | R$^{14}$ | R$^{15}$ | R$^{16}$ | R$^{17}$ | R$^{18}$ |
|---|---|---|---|---|---|---|---|---|---|
| 3-265 | $^i$Bu | H | H | H | H | $^t$Bu | $^t$Bu | $^t$Bu | Me |
| 3-266 | $^s$Bu | H | H | H | H | $^t$Bu | $^t$Bu | $^t$Bu | Me |

[Table 17]

TABLE 5-8

(3)

| Compound No. | R$^{10}$ | R$^{11}$ | R$^{12}$ | R$^{13}$ | R$^{14}$ | R$^{15}$ | R$^{16}$ | R$^{17}$ | R$^{18}$ |
|---|---|---|---|---|---|---|---|---|---|
| 3-267 | $^t$Bu | H | H | H | H | $^t$Bu | $^t$Bu | $^t$Bu | Me |
| 3-268 | Pe | H | H | H | H | $^t$Bu | $^t$Bu | $^t$Bu | Me |
| 3-269 | $^c$Pe | H | H | H | H | $^t$Bu | $^t$Bu | $^t$Bu | Me |
| 3-270 | Hx | H | H | H | H | $^t$Bu | $^t$Bu | $^t$Bu | Me |
| 3-271 | Me | Me | H | H | H | $^t$Bu | $^t$Bu | $^t$Bu | Me |
| 3-272 | Me | H | Me | H | H | $^t$Bu | $^t$Bu | $^t$Bu | Me |
| 3-273 | $^t$Bu | H | $^t$Bu | H | H | $^t$Bu | $^t$Bu | $^t$Bu | Me |
| 3-274 | Me | Me | Me | H | H | $^t$Bu | $^t$Bu | $^t$Bu | Me |
| 3-275 | Me | Me | H | Me | H | $^t$Bu | $^t$Bu | $^t$Bu | Me |
| 3-276 | $^i$Pr | H | $^i$Pr | H | $^i$Pr | $^t$Bu | $^t$Bu | $^t$Bu | Me |
| 3-277 | Me | Me | Me | Me | H | $^t$Bu | $^t$Bu | $^t$Bu | Me |
| 3-278 | Et | Me | Me | Me | Me | $^t$Bu | $^t$Bu | $^t$Bu | Me |
| 3-279 | Pr | Me | Me | Me | Me | $^t$Bu | $^t$Bu | $^t$Bu | Me |
| 3-280 | H | H | H | H | H | $^t$Bu | $^t$Bu | $^t$Bu | Bu |
| 3-281 | Me | H | H | H | H | $^t$Bu | $^t$Bu | $^t$Bu | Bu |
| 3-282 | Et | H | H | H | H | $^t$Bu | $^t$Bu | $^t$Bu | Bu |
| 3-283 | Pr | H | H | H | H | $^t$Bu | $^t$Bu | $^t$Bu | Bu |
| 3-284 | $^i$Pr | H | H | H | H | $^t$Bu | $^t$Bu | $^t$Bu | Bu |
| 3-285 | Bu | H | H | H | H | $^t$Bu | $^t$Bu | $^t$Bu | Bu |
| 3-286 | $^i$Bu | H | H | H | H | $^t$Bu | $^t$Bu | $^t$Bu | Bu |
| 3-287 | $^s$Bu | H | H | H | H | $^t$Bu | $^t$Bu | $^t$Bu | Bu |
| 3-288 | $^t$Bu | H | H | H | H | $^t$Bu | $^t$Bu | $^t$Bu | Bu |
| 3-289 | Pe | H | H | H | H | $^t$Bu | $^t$Bu | $^t$Bu | Bu |
| 3-290 | $^c$Pe | H | H | H | H | $^t$Bu | $^t$Bu | $^t$Bu | Bu |
| 3-291 | Hx | H | H | H | H | $^t$Bu | $^t$Bu | $^t$Bu | Bu |
| 3-292 | Me | Me | H | H | H | $^t$Bu | $^t$Bu | $^t$Bu | Bu |
| 3-293 | Me | H | Me | H | H | $^t$Bu | $^t$Bu | $^t$Bu | Bu |
| 3-294 | $^t$Bu | H | $^t$Bu | H | H | $^t$Bu | $^t$Bu | $^t$Bu | Bu |
| 3-295 | Me | Me | Me | H | H | $^t$Bu | $^t$Bu | $^t$Bu | Bu |
| 3-296 | Me | Me | H | Me | H | $^t$Bu | $^t$Bu | $^t$Bu | Bu |
| 3-297 | $^i$Pr | H | $^i$Pr | H | $^i$Pr | $^t$Bu | $^t$Bu | $^t$Bu | Bu |
| 3-298 | Me | Me | Me | Me | H | $^t$Bu | $^t$Bu | $^t$Bu | Bu |
| 3-299 | Me | Me | Me | Me | Me | $^t$Bu | $^t$Bu | $^t$Bu | Bu |
| 3-300 | Et | Me | Me | Me | Me | $^t$Bu | $^t$Bu | $^t$Bu | Bu |
| 3-301 | Pr | Me | Me | Me | Me | $^t$Bu | $^t$Bu | $^t$Bu | Bu |
| 3-302 | H | H | H | H | H | Me | $^t$Bu | $^i$Pr | Me |
| 3-303 | Me | H | H | H | H | Me | $^t$Bu | $^i$Pr | Me |
| 3-304 | Et | H | H | H | H | Me | $^t$Bu | $^i$Pr | Me |

[Table 18]

TABLE 5-9

(3)

| Compound No. | R$^{10}$ | R$^{11}$ | R$^{12}$ | R$^{13}$ | R$^{14}$ | R$^{15}$ | R$^{16}$ | R$^{17}$ | R$^{18}$ |
|---|---|---|---|---|---|---|---|---|---|
| 3-305 | Pr | H | H | H | H | Me | $^t$Bu | $^i$Pr | Me |
| 3-306 | $^i$Pr | H | H | H | H | Me | $^t$Bu | $^i$Pr | Me |
| 3-307 | Bu | H | H | H | H | Me | $^t$Bu | $^i$Pr | Me |
| 3-308 | $^i$Bu | H | H | H | H | Me | $^t$Bu | $^i$Pr | Me |
| 3-309 | $^s$Bu | H | H | H | H | Me | $^t$Bu | $^i$Pr | Me |
| 3-310 | $^t$Bu | H | H | H | H | Me | $^t$Bu | $^i$Pr | Me |
| 3-311 | Pe | H | H | H | H | Me | $^t$Bu | $^i$Pr | Me |
| 3-312 | $^c$Pe | H | H | H | H | Me | $^t$Bu | $^i$Pr | Me |
| 3-313 | Hx | H | H | H | H | Me | $^t$Bu | $^i$Pr | Me |
| 3-314 | Me | Me | H | H | H | Me | $^t$Bu | $^i$Pr | Me |
| 3-315 | Me | H | Me | H | H | Me | $^t$Bu | $^i$Pr | Me |
| 3-316 | $^t$Bu | H | $^t$Bu | H | H | Me | $^t$Bu | $^i$Pr | Me |
| 3-317 | Me | Me | Me | H | H | Me | $^t$Bu | $^i$Pr | Me |
| 3-318 | Me | Me | H | Me | H | Me | $^t$Bu | $^i$Pr | Me |
| 3-319 | $^i$Pr | H | $^i$Pr | H | $^i$Pr | Me | $^t$Bu | $^i$Pr | Me |

TABLE 5-9-continued

| (3) Compound No. | $R^{10}$ | $R^{11}$ | $R^{12}$ | $R^{13}$ | $R^{14}$ | $R^{15}$ | $R^{16}$ | $R^{17}$ | $R^{18}$ |
|---|---|---|---|---|---|---|---|---|---|
| 3-320 | Me | Me | Me | Me | H | Me | $^t$Bu | $^i$Pr | Me |
| 3-321 | Me | Me | Me | Me | Me | Me | $^t$Bu | $^i$Pr | Me |
| 3-322 | Et | Me | Me | Me | Me | Me | $^t$Bu | $^i$Pr | Me |
| 3-323 | Pr | Me | Me | Me | Me | Me | $^t$Bu | $^i$Pr | Me |
| 3-324 | H | H | H | H | H | Me | $^t$Bu | $^i$Pr | Bu |
| 3-325 | Me | H | H | H | H | Me | $^t$Bu | $^i$Pr | Bu |
| 3-326 | Et | H | H | H | H | Me | $^t$Bu | $^i$Pr | Bu |
| 3-328 | Pr | H | H | H | H | Me | $^t$Bu | $^i$Pr | Bu |
| 3-329 | $^i$Pr | H | H | H | H | Me | $^t$Bu | $^i$Pr | Bu |
| 3-330 | Bu | H | H | H | H | Me | $^t$Bu | $^i$Pr | Bu |
| 3-331 | $^i$Bu | H | H | H | H | Me | $^t$Bu | $^i$Pr | Bu |
| 3-332 | $^s$Bu | H | H | H | H | Me | $^t$Bu | $^i$Pr | Bu |
| 3-333 | $^t$Bu | H | H | H | H | Me | $^t$Bu | $^i$Pr | Bu |
| 3-334 | Pe | H | H | H | H | Me | $^t$Bu | $^i$Pr | Bu |
| 3-335 | $^c$Pe | H | H | H | H | Me | $^t$Bu | $^i$Pr | Bu |
| 3-336 | Hx | H | H | H | H | Me | $^t$Bu | $^i$Pr | Bu |
| 3-337 | Me | Me | H | H | H | Me | $^t$Bu | $^i$Pr | Bu |
| 3-338 | Me | H | Me | H | H | Me | $^t$Bu | $^i$Pr | Bu |
| 3-339 | $^t$Bu | H | $^t$Bu | H | H | Me | $^t$Bu | $^i$Pr | Bu |
| 3-340 | Me | Me | Me | H | H | Me | $^t$Bu | $^i$Pr | Bu |
| 3-341 | Me | Me | H | Me | H | Me | $^t$Bu | $^i$Pr | Bu |
| 3-342 | $^i$Pr | H | $^i$Pr | H | $^i$Pr | Me | $^t$Bu | $^i$Pr | Bu |
| 3-343 | Me | Me | Me | Me | H | Me | $^t$Bu | $^i$Pr | Bu |

[Table 19]

TABLE 5-10

| (3) Compound No. | $R^{10}$ | $R^{11}$ | $R^{12}$ | $R^{13}$ | $R^{14}$ | $R^{15}$ | $R^{16}$ | $R^{17}$ | $R^{18}$ |
|---|---|---|---|---|---|---|---|---|---|
| 3-344 | Me | Me | Me | Me | Me | Me | $^t$Bu | $^i$Pr | Bu |
| 3-345 | Et | Me | Me | Me | Me | Me | $^t$Bu | $^i$Pr | Bu |
| 3-346 | Pr | Me | Me | Me | Me | Me | $^t$Bu | $^i$Pr | Bu |

Among those exemplified in Tables 5-1 to 5-10, in view of having vapor pressure and thermal stability suitable as a CVD material or an ALD material, ($\eta^5$-cyclopentadienyl)($\eta^5$-6-exo-methylcyclohexadienyl)ruthenium (3-1), ($\eta^5$-methylcyclopentadienyl)($\eta^5$-6-exo-methylcyclohexadienyl)ruthenium (3-2), ($\eta^5$-ethylcyclopentadienyl)($\eta^5$-6-exo-methylcyclohexadienyl)ruthenium (3-3), ($\eta^5$-propylcyclopentadienyl)($\eta^5$-6-exo-methylcyclohexadienyl)ruthenium (3-4), ($\eta^5$-isopropylcyclopentadienyl)($\eta^5$-6-exo-methylcyclohexadienyl)ruthenium (3-5), ($\eta^5$-butylcyclopentadienyl)($\eta^5$-6-exo-methylcyclohexadienyl)ruthenium (3-6), ($\eta^5$-isobutylcyclopentadienyl)($\eta^5$-6-exo-methylcyclohexadienyl)ruthenium (3-7), ($\eta^5$-sec-butylcyclopentadienyl)($\eta^5$-6-exo-methylcyclohexadienyl)ruthenium (3-8), ($\eta^5$-tert-butylcyclopentadienyl)($\eta^5$-6-exo-methylcyclohexadienyl)ruthenium (3-9), ($\eta^5$-pentylcyclopentadienyl)($\eta^5$-6-exo-methylcyclohexadienyl)ruthenium (3-10), ($\eta^5$-cyclopentylcyclopentadienyl)($\eta^5$-6-exo-methylcyclohexadienyl)ruthenium (3-11), ($\eta^5$-hexylcyclopentadienyl)($\eta^5$-6-exo-methylcyclohexadienyl)ruthenium (3-12), ($\eta^5$-cyclopentadienyl)($\eta^5$-1,3,5,6-exo-tetramethylcyclohexadienyl)ruthenium (3-44), ($\eta^5$-methylcyclopentadienyl)($\eta^5$-1,3,5,6-exo-tetramethylcyclohexadienyl)ruthenium (3-45), ($\eta^5$-ethylcyclopentadienyl)($\eta^5$-1,3,5,6-exo-tetramethylcyclohexadienyl)ruthenium (3-46), ($\eta^5$-propylcyclopentadienyl)($\eta^5$-1,3,5,6-exo-tetramethylcyclohexadienyl)ruthenium (3-47), ($\eta^5$-isopropylcyclopentadienyl)($\eta^5$-1,3,5,6-exo-tetramethylcyclohexadienyl)ruthenium (3-48), ($\eta^5$-butylcyclopentadienyl)($\eta^5$-1,3,5,6-exo-tetramethylcyclohexadienyl)ruthenium (3-49), ($\eta^5$-isobutylcyclopentadienyl)($\eta^5$-1,3,5,6-exo-tetramethylcyclohexadienyl)ruthenium (3-50), ($\eta^5$-sec-butylcyclopentadienyl)($\eta^5$-1,3,5,6-exo-tetramethylcyclohexadienyl)ruthenium (3-51), ($\eta^5$-tert-butylcyclopentadienyl)($\eta^5$-1,3,5,6-exo-tetramethylcyclohexadienyl)ruthenium (3-52), ($\eta^5$-pentylcyclopentadienyl)($\eta^5$-1,3,5,6-exo-tetramethylcyclohexadienyl)ruthenium (3-53), ($\eta^5$-cyclopentylcyclopentadienyl)($\eta^5$-1,3,5,6-exo-tetramethylcyclohexadienyl)ruthenium (3-54) and ($\eta^5$-hexylcyclopentadienyl)($\eta^5$-1,3,5,6-exo-tetramethylcyclohexadienyl)ruthenium (3-55) are preferred; and ($\eta^5$-ethylcyclopentadienyl)($\eta^5$-6-exo-methylcyclohexadienyl)ruthenium (3-3) and ($\eta^5$-ethylcyclopentadienyl)($\eta^5$-1,3,5,6-exo-tetramethylcyclohexadienyl)ruthenium (3-46) are more preferred.

The production method of the ruthenium complex (3) of the present invention is described below.

The ruthenium complex (3) of the present invention can be produced by the following production method 6 or production method 8.

Production method 6 is a method of reacting a cationic arene complex (10) with an alkyllithium (11) to produce a ruthenium complex (3) of the present invention.

Production Method 6:

[Chem. 14]

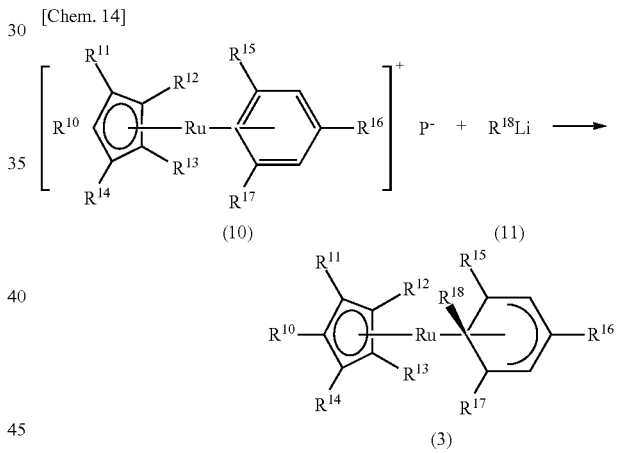

(wherein $R^{10}$ to $R^{18}$ have the same meanings as $R^{10}$ to $R^{18}$ in formula (3), and $P^-$ represents a counter anion.)

Specific examples of the cation moiety of the cationic arene complex (10) include [($\eta^6$-benzene)($\eta^5$-cyclopentadienyl)ruthenium(II)] ([Ru($\eta^5$-C$_5$H$_5$)($\eta^6$-C$_6$H$_6$)]), [($\eta^6$-benzene)($\eta^5$-methylcyclopentadienyl)ruthenium(II)] ([Ru($\eta^5$-C$_5$MeH$_4$)($\eta^6$-C$_6$H$_6$)]), [($\eta^6$-benzene)($\eta^5$-ethylcyclopentadienyl)ruthenium(II)] ([Ru($\eta^5$-C$_5$EtH$_4$)($\eta^6$-C$_6$H$_6$)]), [($\eta^6$-benzene)($\eta^5$-propylcyclopentadienyl)ruthenium(II)] ([Ru($\eta^5$-C$_5$PrH$_4$)($\eta^6$-C$_6$H$_6$)]), [($\eta^6$-benzene)($\eta^5$-isopropylcyclopentadienyl)ruthenium(II)] ([Ru($\eta^5$-C$_5$$^i$PrH$_4$)($\eta^6$-C$_6$H$_6$)]), [($\eta^6$-benzene)($\eta^5$-butylcyclopentadienyl)ruthenium(II)] ([Ru($\eta^5$-C$_5$BuH$_4$)($\eta^6$-C$_6$H$_6$)]), [($\eta^6$-benzene)($\eta^5$-isobutylcyclopentadienyl)ruthenium(II)] ([Ru($\eta^5$-C$_5$$^i$BuH$_4$)($\eta^6$-C$_6$H$_6$)]), [($\eta^6$-benzene)($\eta^5$-sec-butylcyclopentadienyl)ruthenium(II)] ([Ru($\eta^5$-C$_5$$^s$BuH$_4$)($\eta^6$-C$_6$H$_6$)]), [($\eta^6$-benzene)($\eta^5$-tert-butylcyclopentadienyl)ruthenium(II)] ([Ru($\eta^5$-C$_5$$^t$BuH$_4$)($\eta^6$-C$_6$H$_6$)]), [($\eta^6$-benzene)($\eta^5$-pentylcyclopentadienyl)ruthenium(II)] ([Ru($\eta^5$-C$_5$PeH$_4$)($\eta^6$-C$_6$H$_6$)]), [($\eta^6$-benzene)

($\eta^5$-cyclopentylcyclopentadienyl)ruthenium(II)] ([Ru($\eta^5$-C$_5^c$PeH$_4$)($\eta^6$-C$_6$H$_6$)]), [($\eta^6$-benzene)($\eta^5$-hexylcyclopentadienyl)ruthenium(II)] ([Ru($\eta^5$-C$_5$HxH$_4$)($\eta^6$-C$_6$H$_6$)]), [($\eta^6$-benzene)($\eta^5$-1,2,3,4,5-pentamethylcyclopentadienyl)ruthenium(II)] ([Ru($\eta^5$-C$_5$Me$_5$)($\eta^6$-C$_6$H$_6$)]),

[($\eta^5$-cyclopentadienyl)($\eta^6$-1,3,5-trimethylbenzene)ruthenium(II)] ([Ru($\eta^5$-C$_5$H$_5$)($\eta^6$-C$_6$Me$_3$H$_3$)]), [($\eta^5$-methylcyclopentadienyl)($\eta^6$-1,3,5-trimethylbenzene)ruthenium(II)] ([Ru($\eta^5$-C$_5$MeH$_4$)($\eta^6$-C$_6$Me$_3$H$_3$)]), [($\eta^5$-ethylcyclopentadienyl)($\eta^6$-1,3,5-trimethylbenzene)ruthenium(II)] ([Ru($\eta^5$-C$_5$EtH$_4$)($\eta^6$-C$_6$Me$_3$H$_3$)]), [($\eta^5$-propylcyclopentadienyl)($\eta^6$-1,3,5-trimethylbenzene)ruthenium(II)] ([Ru($\eta^5$-C$_5$PrH$_4$)($\eta^6$-C$_6$Me$_3$H$_3$)]), [($\eta^5$-isopropylcyclopentadienyl)($\eta^6$-1,3,5-trimethylbenzene)ruthenium(II)] ([Ru($\eta^5$-C$_5^i$PrH$_4$)($\eta^6$-C$_6$Me$_3$H$_3$)]), [($\eta^5$-butylcyclopentadienyl)($\eta^6$-1,3,5-trimethylbenzene)ruthenium(II)] ([Ru($\eta^5$-C$_5$BuH$_4$)($\eta^6$-C$_6$Me$_3$H$_3$)]), [($\eta^5$-isobutylcyclopentadienyl)($\eta^6$-1,3,5-trimethylbenzene)ruthenium(II)] ([Ru($\eta^5$-C$_5^i$BuH$_4$)($\eta^6$-C$_6$Me$_3$H$_3$)]), [($\eta^5$-sec-butylcyclopentadienyl)($\eta^6$-1,3,5-trimethylbenzene)ruthenium(II)] ([Ru($\eta^5$-C$_5^s$BuH$_4$)($\eta^6$-C$_6$Me$_3$H$_3$)]), [($\eta^5$-tert-butylcyclopentadienyl)($\eta^6$-1,3,5-trimethylbenzene)ruthenium(II)] ([Ru($\eta^5$-C$_5^t$BuH$_4$)($\eta^6$-C$_6$Me$_3$H$_3$)]), [($\eta^5$-pentylcyclopentadienyl)($\eta^6$-1,3,5-trimethylbenzene)ruthenium(II)] ([Ru($\eta^5$-C$_5$PeH$_4$)($\eta^6$-C$_6$Me$_3$H$_3$)]), [($\eta^5$-cyclopentylcyclopentadienyl)($\eta^6$-1,3,5-trimethylbenzene)ruthenium(II)] ([Ru($\eta^5$-C$_5^c$PeH$_4$)($\eta^6$-C$_6$Me$_3$H$_3$)]), [($\eta^5$-hexylcyclopentadienyl)($\eta^6$-1,3,5-trimethylbenzene)ruthenium(II)] ([Ru($\eta^5$-C$_5$HxH$_4$)($\eta^6$-C$_6$Me$_3$H$_3$)]), [($\eta^5$-1,2,3,4,5-pentamethylcyclopentadienyl)($\eta^6$-1,3,5-trimethylbenzene)ruthenium(II)] ([Ru($\eta^5$-C$_5$Me$_5$)($\eta^6$-C$_6$Me$_3$H$_3$)]), [($\eta^5$-cyclopentadienyl)($\eta^6$-1,3,5-triethylbenzene)ruthenium(II)] ([Ru($\eta^5$-C$_5$H$_5$)($\eta^6$-C$_6$Et$_3$H$_3$)]), [($\eta^5$-methylcyclopentadienyl)($\eta^6$-1,3,5-triethylbenzene)ruthenium(II)] ([Ru($\eta^5$-C$_5$MeH$_4$)($\eta^6$-C$_6$Et$_3$H$_3$)]), [($\eta^5$-ethylcyclopentadienyl)($\eta^6$-1,3,5-triethylbenzene)ruthenium(II)] ([Ru($\eta^5$-C$_5$EtH$_4$)($\eta^6$-C$_6$Et$_3$H$_3$)]), [($\eta^5$-propylcyclopentadienyl)($\eta^6$-1,3,5-triethylbenzene)ruthenium(II)] ([Ru($\eta^5$-C$_5$PrH$_4$)($\eta^6$-C$_6$Et$_3$H$_3$)]), [($\eta^5$-isopropylcyclopentadienyl)($\eta^6$-1,3,5-triethylbenzene)ruthenium(II)] ([Ru($\eta^5$-C$_5^i$PrH$_4$)($\eta^6$-C$_6$Et$_3$H$_3$)]),

[($\eta^5$-butylcyclopentadienyl)($\eta^6$-1,3,5-triethylbenzene)ruthenium(II)] ([Ru($\eta^5$-C$_5$BuH$_4$)($\eta^6$-C$_6$Et$_3$H$_3$)]), [($\eta^5$-isobutylcyclopentadienyl)($\eta^6$-1,3,5-triethylbenzene)ruthenium(II)] ([Ru($\eta^5$-C$_5^i$BuH$_4$)($\eta^6$-C$_6$Et$_3$H$_3$)]), [($\eta^5$-sec-butylcyclopentadienyl)($\eta^6$-1,3,5-triethylbenzene)ruthenium(II)] ([Ru($\eta^5$-C$_5^s$BuH$_4$)($\eta^6$-C$_6$Et$_3$H$_3$)]), [($\eta^5$-tert-butylcyclopentadienyl)($\eta^6$-1,3,5-triethylbenzene)ruthenium(II)] ([Ru($\eta^5$-C$_5^t$BuH$_4$)($\eta^6$-C$_6$Et$_3$H$_3$)]), [($\eta^5$-pentylcyclopentadienyl)($\eta^6$-1,3,5-triethylbenzene)ruthenium(II)] ([Ru($\eta^5$-C$_5$PeH$_4$)($\eta^6$-C$_6$Et$_3$H$_3$)]), [($\eta^5$-cyclopentylcyclopentadienyl)($\eta^6$-1,3,5-triethylbenzene)ruthenium(II)] ([Ru($\eta^5$-C$_5^c$PeH$_4$)($\eta^6$-C$_6$Et$_3$H$_3$)]), [($\eta^5$-hexylcyclopentadienyl)($\eta^6$-1,3,5-triethylbenzene)ruthenium(II)] ([Ru($\eta^5$-C$_5$HxH$_4$)($\eta^6$-C$_6$Et$_3$H$_3$)]), [($\eta^5$-1,2,3,4,5-pentamethylcyclopentadienyl)($\eta^6$-1,3,5-triethylbenzene)ruthenium(II)] ([Ru($\eta^5$-C$_5$Me$_5$)($\eta^6$-C$_6$Et$_3$H$_3$)]), [($\eta^5$-cyclopentadienyl)($\eta^6$-1,3,5-tripropylbenzene)ruthenium(II)] ([Ru($\eta^5$-C$_5$H$_5$)($\eta^6$-C$_6$Pr$_3$H$_3$)]), [($\eta^5$-methylcyclopentadienyl)($\eta^6$-1,3,5-tripropylbenzene)ruthenium(II)] ([Ru($\eta^5$-C$_5$MeH$_4$)($\eta^6$-C$_6$Pr$_3$H$_3$)]), [($\eta^5$-ethylcyclopentadienyl)($\eta^6$-1,3,5-tripropylbenzene)ruthenium(II)] ([Ru($\eta^5$-C$_5$EtH$_4$)($\eta^6$-C$_6$Pr$_3$H$_3$)]), [($\eta^5$-propylcyclopentadienyl)($\eta^6$-1,3,5-tripropylbenzene)ruthenium(II)] ([Ru($\eta^5$-C$_5$PrH$_4$)($\eta^6$-C$_6$Pr$_3$H$_3$)]), [($\eta^5$-isopropylcyclopentadienyl)($\eta^6$-1,3,5-tripropylbenzene)ruthenium(II)] ([Ru($\eta^5$-C$_5^i$PrH$_4$)($\eta^6$-C$_6$Pr$_3$H$_3$)]), [($\eta^5$-butylcyclopentadienyl)($\eta^6$-1,3,5-tripropylbenzene)ruthenium(II)] ([Ru($\eta^5$-C$_5$BuH$_4$)($\eta^6$-C$_6$Pr$_3$H$_3$)]), [($\eta^5$-isobutylcyclopentadienyl)($\eta^6$-1,3,5-tripropylbenzene)ruthenium(II)] ([Ru($\eta^5$-C$_5^i$BuH$_4$)($\eta^6$-C$_6$Pr$_3$H$_3$)]), [($\eta^5$-sec-butylcyclopentadienyl)($\eta^6$-1,3,5-tripropylbenzene)ruthenium(II)] ([Ru($\eta^5$-C$_5^s$BuH$_4$)($\eta^6$-C$_6$Pr$_3$H$_3$)]), [($\eta^5$-tert-butylcyclopentadienyl)($\eta^6$-1,3,5-tripropylbenzene)ruthenium(II)] ([Ru($\eta^5$-C$_5^t$BuH$_4$)($\eta^6$-C$_6$Pr$_3$H$_3$)]),

[($\eta^5$-pentylcyclopentadienyl)($\eta^6$-1,3,5-tripropylbenzene)ruthenium(II)] ([Ru($\eta^5$-C$_5$PeH$_4$)($\eta^6$-C$_6$Pr$_3$H$_3$)]), [($\eta^5$-cyclopentylcyclopentadienyl)($\eta^6$-1,3,5-tripropylbenzene)ruthenium(II)] ([Ru($\eta^5$-C$_5^c$PeH$_4$)($\eta^6$-C$_6$Pr$_3$H$_3$)]), [($\eta^5$-hexylcyclopentadienyl)($\eta^6$-1,3,5-tripropylbenzene)ruthenium(II)] ([Ru($\eta^5$-C$_5$HxH$_4$)($\eta^6$-C$_6$Pr$_3$H$_3$)]), [($\eta^5$-1,2,3,4,5-pentamethylcyclopentadienyl)($\eta^6$-1,3,5-tripropylbenzene)ruthenium(II)] ([Ru($\eta^5$-C$_5$Me$_5$)($\eta^6$-C$_6$Pr$_3$H$_3$)]), [($\eta^5$-cyclopentadienyl)($\eta^6$-1,3,5-tri(isopropyl)benzene)ruthenium(II)] ([Ru($\eta^5$-C$_5$H$_5$)($\eta^6$-C$_6$($^i$Pr)$_3$H$_3$)]), [($\eta^5$-methylcyclopentadienyl)($\eta^6$-1,3,5-tri(isopropyl)benzene)ruthenium(II)] ([Ru($\eta^5$-C$_5$MeH$_4$)($\eta^6$-C$_6$($^i$Pr)$_3$H$_3$)]), [($\eta^5$-ethylcyclopentadienyl)($\eta^6$-1,3,5-tri(isopropyl)benzene)ruthenium(II)] ([Ru($\eta^5$-C$_5$EtH$_4$)($\eta^6$-C$_6$($^i$Pr)$_3$H$_3$)]), [($\eta^5$-propylcyclopentadienyl)($\eta^6$-1,3,5-tri(isopropyl)benzene)ruthenium(II)] ([Ru($\eta^5$-C$_5$PrH$_4$)($\eta^6$-C$_6$($^i$Pr)$_3$H$_3$)]), [($\eta^5$-isopropylcyclopentadienyl)($\eta^6$-1,3,5-tri(isopropyl)benzene)ruthenium(II)] ([Ru($\eta^5$-C$_5^i$PrH$_4$)($\eta^6$-C$_6$($^i$Pr)$_3$H$_3$)]), [($\eta^5$-butylcyclopentadienyl)($\eta^6$-1,3,5-tri(isopropyl)benzene)ruthenium(II)] ([Ru($\eta^5$-C$_5$BuH$_4$)($\eta^6$-C$_6$($^i$Pr)$_3$H$_3$)]), [($\eta^5$-isobutylcyclopentadienyl)($\eta^6$-1,3,5-tri(isopropyl)benzene)ruthenium(II)] ([Ru($\eta^5$-C$_5^i$BuH$_4$)($\eta^6$-C$_6$($^i$Pr)$_3$H$_3$)]), [($\eta^5$-sec-butylcyclopentadienyl)($\eta^6$-1,3,5-tri(isopropyl)benzene)ruthenium(II)] ([Ru($\eta^5$-C$_5^s$BuH$_4$)($\eta^6$-C$_6$($^i$Pr)$_3$H$_3$)]), [($\eta^5$-tert-butylcyclopentadienyl)($\eta^6$-1,3,5-tri(isopropyl)benzene)ruthenium(II)] ([Ru($\eta^5$-C$_5^t$BuH$_4$)($\eta^6$-C$_6$($^i$Pr)$_3$H$_3$)]), [($\eta^5$-pentylcyclopentadienyl)($\eta^6$-1,3,5-tri(isopropyl)benzene)ruthenium(II)] ([Ru($\eta^5$-C$_5$PeH$_4$)($\eta^6$-C$_6$($^i$Pr)$_3$H$_3$)]), [($\eta^5$-cyclopentylcyclopentadienyl)($\eta^6$-1,3,5-tri(isopropyl)benzene)ruthenium(II)] ([Ru($\eta^5$-C$_5^c$PeH$_4$)($\eta^6$-C$_6$($^i$Pr)$_3$H$_3$)]), [($\eta^5$-hexylcyclopentadienyl)($\eta^6$-1,3,5-tri(isopropyl)benzene)ruthenium(II)] ([Ru($\eta^5$-C$_5$HxH$_4$)($\eta^6$-C$_6$($^i$Pr)$_3$H$_3$)]),

[($\eta^5$-1,2,3,4,5-pentamethylcyclopentadienyl)($\eta^6$-1,3,5-tri(isopropyl)benzene)ruthenium(II)] ([Ru($\eta^5$-C$_5$Me$_5$)($\eta^6$-C$_6$($^i$Pr)$_3$H$_3$)]), [($\eta^5$-cyclopentadienyl)($\eta^6$-1,3,5-tributylbenzene)ruthenium(II)] ([Ru($\eta^5$-C$_5$H$_5$)($\eta^6$-C$_6$Bu$_3$H$_3$)]), [($\eta^5$-methylcyclopentadienyl)($\eta^6$-1,3,5-tributylbenzene)ruthenium(II)] ([Ru($\eta^5$-C$_5$MeH$_4$)($\eta^6$-C$_6$Bu$_3$H$_3$)]), [($\eta^5$-ethylcyclopentadienyl)($\eta^6$-1,3,5-tributylbenzene)ruthenium(II)] ([Ru($\eta^5$-C$_5$EtH$_4$)($\eta^6$-C$_6$Bu$_3$H$_3$)]), [($\eta^5$-propylcyclopentadienyl)($\eta^6$-1,3,5-tributylbenzene)ruthenium(II)] ([Ru($\eta^5$-C$_5$PrH$_4$)($\eta^6$-C$_6$Bu$_3$H$_3$)]), [($\eta^5$-isopropylcyclopentadienyl)($\eta^6$-1,3,5-tributylbenzene)ruthenium(II)] ([Ru($\eta^5$-C$_5^i$PrH$_4$)($\eta^6$-C$_6$Bu$_3$H$_3$)]), [($\eta^5$-butylcyclopentadienyl)($\eta^6$-1,3,5-tributylbenzene)ruthenium(II)] ([Ru($\eta^5$-C$_5$BuH$_4$)($\eta^6$-C$_6$Bu$_3$H$_3$)]), [($\eta^5$-isobutylcyclopentadienyl)($\eta^6$-1,3,5-tributylbenzene)ruthenium(II)] ([Ru($\eta^5$-C$_5^i$BuH$_4$)($\eta^6$-C$_6$Bu$_3$H$_3$)]), [($\eta^5$-sec-butylcyclopentadienyl)($\eta^6$-1,3,5-tributylbenzene)ruthenium(II)] ([Ru($\eta^5$-C$_5^s$BuH$_4$)($\eta^6$-C$_6$Bu$_3$H$_3$)]), [($\eta^5$-tert-butylcyclopentadienyl)($\eta^6$-1,3,5-tributylbenzene)ruthenium(II)] ([Ru($\eta^5$-C$_5^t$BuH$_4$)($\eta^6$-C$_6$Bu$_3$H$_3$)]), [($\eta^5$-pentylcyclopentadienyl)($\eta^6$-1,3,5-tributylbenzene)ruthenium(II)] ([Ru($\eta^5$-C$_5$PeH$_4$)($\eta^6$-C$_6$Bu$_3$H$_3$)]), [($\eta^5$-cyclopentylcyclopentadienyl)($\eta^6$-1,3,5-tributylbenzene)ruthenium(II)] ([Ru($\eta^5$-C$_5^c$PeH$_4$)($\eta^6$-C$_6$Bu$_3$H$_3$)]), [($\eta^5$-hexylcyclopentadienyl)($\eta^6$-1,3,5-tributylbenzene)ruthenium(II)] ([Ru($\eta^5$-C$_5$HxH$_4$)($\eta^6$-C$_6$Bu$_3$H$_3$)]), [($\eta^5$-1,2,3,4,5-pentamethylcyclopentadienyl)($\eta^6$-1,3,5-tributylbenzene)

ruthenium(II)] ([Ru($\eta^5$-C$_5$Me$_5$)($\eta^6$-C$_6$Bu$_3$H$_3$)]), [($\eta^6$-1,3,5-tri(tert-butyl)benzene)($\eta^5$-cyclopentadienyl)ruthenium(II)] ([Ru($\eta^5$-C$_5$H$_5$)($\eta^5$-C$_6$($^t$Bu)$_3$H$_3$)]), [($\eta^5$-methylcyclopentadienyl)($\eta^6$-1,3,5-tri(tert-butyl)benzene)ruthenium(II)] ([Ru($\eta^5$-C$_5$MeH$_4$)($\eta^6$-C$_6$($^t$Bu)$_3$H$_3$)]), [($\eta^5$-ethylcyclopentadienyl)($\eta^6$-1,3,5-tri(tert-butyl)benzene)ruthenium(II)] ([Ru($\eta^5$-C$_5$EtH$_4$)($\eta^6$-C$_6$($^t$Bu)$_3$H$_3$)]), [($\eta^5$-propylcyclopentadienyl)($\eta^6$-1,3,5-tri(tert-butyl)benzene)ruthenium(II)] ([Ru($\eta^5$-C$_5$PrH$_4$)($\eta^6$-C$_6$($^t$Bu)$_3$H$_3$)]),

[($\eta^5$-isopropylcyclopentadienyl)($\eta^6$-1,3,5-tri(tert-butyl)benzene)ruthenium(II)] ([Ru($\eta^5$-C$_5$$^i$PrH$_4$)($\eta^6$-C$_6$($^t$Bu)$_3$H$_3$)]), [($\eta^5$-butylcyclopentadienyl)($\eta^6$-1,3,5-tri(tert-butyl)benzene)ruthenium(II)] ([Ru($\eta^5$-C$_5$BuH$_4$)($\eta^6$-C$_6$($^t$Bu)$_3$H$_3$)]), [($\eta^5$-isobutylcyclopentadienyl)($\eta^6$-1,3,5-tri(tert-butyl)benzene)ruthenium(II)] ([Ru($\eta^5$-C$_5$$^i$BuH$_4$)($\eta^6$-C$_6$($^t$Bu)$_3$H$_3$)]), [($\eta^5$-sec-butylcyclopentadienyl)($\eta^6$-1,3,5-tri(tert-butyl)benzene)ruthenium(II)] ([Ru($\eta^5$-C$_5$$^s$BuH$_4$)($\eta^6$-C$_6$($^t$Bu)$_3$H$_3$)]), [($\eta^5$-tert-butylcyclopentadienyl)($\eta^6$-1,3,5-tri(tert-butyl)benzene)ruthenium(II)] ([Ru($\eta^5$-C$_5$$^t$BuH$_4$)($\eta^6$-C$_6$($^t$Bu)$_3$H$_3$)]), [($\eta^5$-pentylcyclopentadienyl)($\eta^6$-1,3,5-tri(tert-butyl)benzene)ruthenium(II)] ([Ru($\eta^5$-C$_5$PeH$_4$)($\eta^6$-C$_6$($^t$Bu)$_3$H$_3$)]), [($\eta^5$-cyclopentylcyclopentadienyl)($\eta^6$-1,3,5-tri(tert-butyl)benzene)ruthenium(II)] ([Ru($\eta^5$-C$_5$$^c$PeH$_4$)($\eta^6$-C$_6$($^t$Bu)$_3$H$_3$)]), [($\eta^5$-hexylcyclopentadienyl)($\eta^6$-1,3,5-tri(tert-butyl)benzene)ruthenium(II)] ([Ru($\eta^5$-C$_5$HxH$_4$)($\eta^6$-C$_6$($^t$Bu)$_3$H$_3$)]), and [($\eta^5$-1,2,3,4,5-pentamethylcyclopentadienyl)($\eta^6$-1,3,5-tri(tert-butyl)benzene)ruthenium(II)] ([Ru($\eta^5$-C$_5$Me$_5$)($\eta^6$-C$_6$($^t$Bu)$_3$H$_3$)]).

For the reason that the ruthenium complex (3) has vapor pressure suitable as a CVD material or an ALD material, [($\eta^6$-benzene)($\eta^5$-cyclopentadienyl)ruthenium(II)] ([Ru($\eta^5$-C$_5$H$_5$)($\eta^6$-C$_6$H$_6$)]), [($\eta^6$-benzene)($\eta^5$-methylcyclopentadienyl)ruthenium(II)] ([Ru($\eta^5$-C$_5$MeH$_4$)($\eta^6$-C$_6$H$_6$)]), [($\eta^6$-benzene)($\eta^5$-ethylcyclopentadienyl)ruthenium(II)] ([Ru($\eta^5$-C$_5$EtH$_4$)($\eta^6$-C$_6$H$_6$)]), [($\eta^6$-benzene)($\eta^5$-propylcyclopentadienyl)ruthenium(II)] ([Ru($\eta^5$-C$_5$PrH$_4$)($\eta^6$-C$_6$H$_6$)]), [($\eta^6$-benzene)($\eta^5$-isopropylcyclopentadienyl)ruthenium(II)] ([Ru($\eta^5$-C$_5$$^i$PrH$_4$)($\eta^6$-C$_6$H$_6$)]), [($\eta^6$-benzene)($\eta^5$-butylcyclopentadienyl)ruthenium(II)] ([Ru($\eta^5$-C$_5$BuH$_4$)($\eta^6$-C$_6$H$_6$)]), [($\eta^6$-benzene)($\eta^5$-isobutylcyclopentadienyl)ruthenium(II)] ([Ru($\eta^5$-C$_5$$^i$BuH$_4$)($\eta^6$-C$_6$H$_6$)]), [($\eta^6$-benzene)($\eta^5$-sec-butylcyclopentadienyl)ruthenium(II)] ([Ru($\eta^5$-C$_5$$^s$BuH$_4$)($\eta^6$-C$_6$H$_6$)]), [($\eta^6$-benzene)($\eta^5$-tert-butylcyclopentadienyl)ruthenium(II)] ([Ru($\eta^5$-C$_5$$^t$BuH$_4$)($\eta^6$-C$_6$H$_6$)]), [($\eta^6$-cyclopentadienyl)($\eta^6$-1,3,5-trimethylbenzene)ruthenium(II)] ([Ru($\eta^5$-C$_5$H$_5$)($\eta^6$-C$_6$Me$_3$H$_3$)]), [($\eta^5$-methylcyclopentadienyl)($\eta^6$-1,3,5-trimethylbenzene)ruthenium(II)] ([Ru($\eta^5$-C$_5$MeH$_4$)($\eta^6$-C$_6$Me$_3$H$_3$)]), [($\eta^5$-ethylcyclopentadienyl)($\eta^6$-1,3,5-trimethylbenzene)ruthenium(II)] ([Ru($\eta^5$-C$_5$EtH$_4$)($\eta^6$-C$_6$Me$_3$H$_3$)]), [($\eta^5$-propylcyclopentadienyl)($\eta^6$-1,3,5-trimethylbenzene)ruthenium(II)] ([Ru($\eta^5$-C$_5$PrH$_4$)($\eta^6$-C$_6$Me$_3$H$_3$)]), [($\eta^5$-isopropylcyclopentadienyl)($\eta^6$-1,3,5-trimethylbenzene)ruthenium(II)] ([Ru($\eta^5$-C$_5$$^i$PrH$_4$)($\eta^6$-C$_6$Me$_3$H$_3$)]), [($\eta^5$-butylcyclopentadienyl)($\eta^6$-1,3,5-trimethylbenzene)ruthenium(II)] ([Ru($\eta^5$-C$_5$BuH$_4$)($\eta^6$-C$_6$Me$_3$H$_3$)]), [($\eta^5$-isobutylcyclopentadienyl)($\eta^6$-1,3,5-trimethylbenzene)ruthenium(II)] ([Ru($\eta^5$-C$_5$$^i$BuH$_4$)($\eta^6$-C$_6$Me$_3$H$_3$)]), [($\eta^5$-sec-butylcyclopentadienyl)($\eta^6$-1,3,5-trimethylbenzene)ruthenium(II)] ([Ru($\eta^5$-C$_5$$^s$BuH$_4$)($\eta^6$-C$_6$Me$_3$H$_3$)]), [($\eta^5$-tert-butylcyclopentadienyl)($\eta^6$-1,3,5-trimethylbenzene)ruthenium(II)] ([Ru($\eta^5$-C$_5$$^t$BuH$_4$)($\eta^6$-C$_6$Me$_3$H$_3$)]), etc. are preferred.

Examples of the counter anion P$^-$ in formula (10) include those generally used as a counter anion of a cationic metal complex. Specific examples thereof include a fluoro complex anion such as tetrafluoroborate ion (BF$_4$$^-$), hexafluorophosphate ion (PF$_6$$^-$), hexafluoroantimonate ion (SbF$_6$$^-$) and tetrafluoroaluminate ion (AlF$_4$$^-$), a monovalent sulfonate ion such as trifluoromethanesulfonate ion (CF$_3$SO$_3$$^-$), methanesulfonate ion (MeSO$_3$$^-$) and methylsulfate ion (MeSO$_4$$^-$), a counter anion of a monobasic acid, such as nitrate ion (NO$_3$$^-$), perchlorate ion (ClO$_4$$^-$), tetrachloroaluminate ion (AlCl$_4$$^-$) and bis(trifluoromethanesulfonyl)amide ion ((CF$_3$SO$_2$)$_2$N$^-$), a counter anion of a polybasic acid, such as sulfate ion (SO$_4$$^{2-}$), hydrogen sulfate ion (HSO$_4$$^-$), phosphate ion (PO$_4$$^{3-}$), monohydrogen phosphate ion (HPO$_4$$^{2-}$), dihydrogen phosphate ion (H$_2$PO$_4$$^-$), dimethylphosphate ion ((MeO)$_2$PO$_4$$^-$) and diethylphosphate ion ((EtO)$_2$PO$_4$$^-$), and a derivative thereof. In view of a high yield of the ruthenium complex (3), the counter anion P$^-$ is preferably a fluoro complex anion such as BF$_4$$^-$ and PF$_6$$^-$, or a monovalent sulfonate ion such as CF$_3$SO$_3$$^-$ and MeSO$_3$$^-$.

Specific preferred examples of the cationic arene complex (10) include [($\eta^6$-benzene)($\eta^5$-cyclopentadienyl)ruthenium(II)][tetrafluoroborate] ([Ru($\eta^5$-C$_5$H$_5$)($\eta^6$-C$_6$H$_6$)][BF$_4$]), [($\eta^6$-benzene)($\eta^5$-methylcyclopentadienyl)ruthenium(II)][tetrafluoroborate] ([Ru($\eta^5$-C$_5$MeH$_4$)($\eta^6$-C$_6$H$_6$)][BF$_4$]), [($\eta^6$-benzene)($\eta^5$-ethylcyclopentadienyl)ruthenium(II)][tetrafluoroborate] ([Ru($\eta^5$-C$_5$EtH$_4$)($\eta^6$-C$_6$H$_6$)][BF$_4$]), [($\eta^6$-benzene)($\eta^5$-1,2,3,4,5-pentamethylcyclopentadienyl)ruthenium(II)][tetrafluoroborate] ([Ru($\eta^5$-C$_5$Me$_5$)($\eta^6$-C$_6$H$_6$)][BF$_4$]), [($\eta^6$-benzene)($\eta^5$-cyclopentadienyl)ruthenium(II)][hexafluorophosphate] ([Ru($\eta^5$-C$_5$H$_5$)($\eta^6$-C$_6$H$_6$)][PF$_6$]), [($\eta^6$-benzene)($\eta^5$-methylcyclopentadienyl)ruthenium(II)][hexafluorophosphate] ([Ru($\eta^5$-C$_5$MeH$_4$)($\eta^6$-C$_6$H$_6$)][PF$_6$]), [($\eta^6$-benzene)($\eta^5$-ethylcyclopentadienyl)ruthenium(II)][hexafluorophosphate] ([Ru($\eta^5$-C$_5$EtH$_4$)($\eta^6$-C$_6$H$_6$)][PF$_6$]), [($\eta^6$-benzene)($\eta^5$-1,2,3,4,5-pentamethylcyclopentadienyl)ruthenium(II)][hexafluorophosphate] ([Ru($\eta^5$-C$_5$Me$_5$)($\eta^6$-C$_6$H$_6$)][PF$_6$]), [($\eta^6$-benzene)($\eta^5$-cyclopentadienyl)ruthenium(II)][trifluoromethanesulfonate] ([Ru($\eta^5$-C$_5$H$_5$)($\eta^6$-C$_6$H$_6$)][CF$_3$SO$_3$]), [($\eta^6$-benzene)($\eta^5$-methylcyclopentadienyl)ruthenium(II)][trifluoromethanesulfonate] ([Ru($\eta^5$-C$_5$MeH$_4$)($\eta^6$-C$_6$H$_6$)][CF$_3$SO$_3$]), [($\eta^6$-benzene)($\eta^5$-ethylcyclopentadienyl)ruthenium(II)][trifluoromethanesulfonate] ([Ru($\eta^5$-C$_5$EtH$_4$)($\eta^6$-C$_6$H$_6$)][CF$_3$SO$_3$]), [($\eta^6$-benzene)($\eta^5$-1,2,3,4,5-pentamethylcyclopentadienyl)ruthenium(II)][trifluoromethanesulfonate] ([Ru($\eta^5$-C$_5$Me$_5$)($\eta^6$-C$_6$H$_6$)][CF$_3$SO$_3$]), [($\eta^6$-benzene)($\eta^5$-cyclopentadienyl)ruthenium(II)][methanesulfonate] ([Ru($\eta^5$-C$_5$H$_5$)($\eta^6$-C$_6$H$_6$)][MeSO$_3$]), [($\eta^6$-benzene)($\eta^5$-methylcyclopentadienyl)ruthenium(II)][methanesulfonate] ([Ru($\eta^5$-C$_5$MeH$_4$)($\eta^6$-C$_6$H$_6$)][MeSO$_3$]), [($\eta^6$-benzene)($\eta^5$-ethylcyclopentadienyl)ruthenium(II)][methanesulfonate] ([Ru($\eta^5$-C$_5$EtH$_4$)($\eta^6$-C$_6$H$_6$)][MeSO$_3$]), [($\eta^6$-benzene)($\eta^5$-1,2,3,4,5-pentamethylcyclopentadienyl)ruthenium(II)][methanesulfonate] ([Ru($\eta^5$-C$_5$Me$_5$)($\eta^6$-C$_6$H$_6$)][MeSO$_3$]), [($\eta^5$-cyclopentadienyl)($\eta^6$-1,3,5-trimethylbenzene)ruthenium(II)][tetrafluoroborate] ([Ru($\eta^5$-C$_5$H$_5$)($\eta^6$-C$_6$Me$_3$H$_3$)][BF$_4$]),

[($\eta^5$-methylcyclopentadienyl)($\eta^6$-1,3,5-trimethylbenzene)ruthenium(II)][tetrafluoroborate] ([Ru($\eta^5$-C$_5$MeH$_4$)($\eta^6$-C$_6$Me$_3$H$_3$)][BF$_4$]), [($\eta^5$-ethylcyclopentadienyl)($\eta^6$-1,3,5-trimethylbenzene)ruthenium(II)][tetrafluoroborate] ([Ru($\eta^5$-C$_5$EtH$_4$)($\eta^6$-C$_6$Me$_3$H$_3$)][BF$_4$]), [($\eta^5$-1,2,3,4,5-pentamethylcyclopentadienyl)($\eta^6$-1,3,5-trimethylbenzene)ruthenium(II)][tetrafluoroborate] ([Ru($\eta^5$-C$_5$Me$_5$)($\eta^6$-C$_6$Me$_3$H$_3$)][BF$_4$]), [($\eta^5$-cyclopentadienyl)($\eta^6$-1,3,5-trimethylbenzene)ruthenium(II)][hexafluorophosphate] ([Ru($\eta^5$-C$_5$H$_5$)($\eta^6$-C$_6$Me$_3$H$_3$)][PF$_6$]), [($\eta^5$-methylcyclopentadienyl)($\eta^6$-1,3,5-trimethylbenzene)ruthenium(II)][hexafluorophosphate] ([Ru($\eta^5$-C$_5$MeH$_4$)($\eta^6$-C$_6$Me$_3$H$_3$)]

[PF$_6$]), [($\eta^5$-ethylcyclopentadienyl)($\eta^6$-1,3,5-trimethylbenzene)ruthenium(II)][hexafluorophosphate] ([Ru($\eta^5$-C$_5$EtH$_4$)($\eta^6$-C$_6$Me$_3$H$_3$)][PF$_6$]), [($\eta^5$-1,2,3,4,5-pentamethylcyclopentadienyl)($\eta^6$-1,3,5-trimethylbenzene)ruthenium(II)][hexafluorophosphate] ([Ru($\eta^5$-C$_5$Me$_5$)($\eta^6$-C$_6$Me$_3$H$_3$)][PF$_6$]), [($\eta^5$-cyclopentadienyl)($\eta^6$-1,3,5-trimethylbenzene)ruthenium(II)][trifluoromethanesulfonate] ([Ru($\eta^5$-C$_5$H$_5$)($\eta^6$-C$_6$Me$_3$H$_3$)][CF$_3$SO$_3$]), [($\eta^5$-methylcyclopentadienyl)($\eta^6$-1,3,5-trimethylbenzene)ruthenium(II)][trifluoromethanesulfonate] ([Ru($\eta^5$-C$_5$MeH$_4$)($\eta^6$-C$_6$Me$_3$H$_3$)][CF$_3$SO$_3$]), [($\eta^5$-ethylcyclopentadienyl)($\eta^6$-1,3,5-trimethylbenzene)ruthenium(II)][trifluoromethanesulfonate] ([Ru($\eta^5$-C$_5$EtH$_4$)($\eta^6$-C$_6$Me$_3$H$_3$)][CF$_3$SO$_3$]), [($\eta^5$-1,2,3,4,5-pentamethylcyclopentadienyl)($\eta^6$-1,3,5-trimethylbenzene)ruthenium(II)][trifluoromethanesulfonate] ([Ru($\eta^5$-C$_5$Me$_5$)($\eta^6$-C$_6$Me$_3$H$_3$)][CF$_3$SO$_3$]), [($\eta^5$-cyclopentadienyl)($\eta^6$-1,3,5-trimethylbenzene)ruthenium(II)][methanesulfonate] ([Ru($\eta^5$-C$_5$H$_5$)($\eta^6$-C$_6$Me$_3$H$_3$)][MeSO$_3$]), [($\eta^5$-methylcyclopentadienyl)($\eta^6$-1,3,5-trimethylbenzene)ruthenium(II)][methanesulfonate] ([Ru($\eta^5$-C$_5$MeH$_4$)($\eta^6$-C$_6$Me$_3$H$_3$)][MeSO$_3$]), [($\eta^5$-ethylcyclopentadienyl)($\eta^6$-1,3,5-trimethylbenzene)ruthenium(II)][methanesulfonate] ([Ru($\eta^5$-C$_5$EtH$_4$)($\eta^6$-C$_6$Me$_3$H$_3$)][MeSO$_3$]), and [($\eta^5$-1,2,3,4,5-pentamethylcyclopentadienyl)($\eta^6$-1,3,5-trimethylbenzene)ruthenium(II)][methanesulfonate] ([Ru($\eta^5$-C$_5$Me$_5$)($\eta^6$-C$_6$Me$_3$H$_3$)][MeSO$_3$]).

For the reason that the yield of the ruthenium complex (3) is high, [($\eta^6$-benzene)($\eta^5$-cyclopentadienyl)ruthenium(II)][tetrafluoroborate] ([Ru($\eta^5$-C$_5$H$_5$)($\eta^6$-C$_6$H$_6$)][BF$_4$]), [($\eta^6$-benzene)($\eta^5$-methylcyclopentadienyl)ruthenium(II)][tetrafluoroborate] ([Ru($\eta^5$-C$_5$MeH$_4$)($\eta^6$-C$_6$H$_6$)][BF$_4$]), [($\eta^6$-benzene)($\eta^5$-ethylcyclopentadienyl)ruthenium(II)][tetrafluoroborate] ([Ru($\eta^5$-C$_5$EtH$_4$)($\eta^6$-C$_6$H$_6$)][BF$_4$]), [($\eta^5$-cyclopentadienyl)($\eta^6$-1,3,5-trimethylbenzene)ruthenium(II)][tetrafluoroborate] ([Ru($\eta^5$-C$_5$H$_5$)($\eta^6$-C$_6$Me$_3$H$_3$)][BF$_4$]), [($\eta^5$-methylcyclopentadienyl)($\eta^6$-1,3,5-trimethylbenzene)ruthenium(II)][tetrafluoroborate] ([Ru($\eta^5$-C$_5$MeH$_4$)($\eta^6$-C$_6$Me$_3$H$_3$)][BF$_4$]), [($\eta^5$-ethylcyclopentadienyl)($\eta^6$-1,3,5-trimethylbenzene)ruthenium(II)][tetrafluoroborate] ([Ru($\eta^5$-C$_5$EtH$_4$)($\eta^6$-C$_6$Me$_3$H$_3$)][BF$_4$]), etc. are preferred.

Specific examples of the alkyllithium (11) include methyllithium, ethyllithium, propyllithium, isopropyllithium, butyllithium, isobutyllithium, sec-butyllithium, tert-butyllithium, pentyllithium, tert-pentyllithium, cyclopentyllithium, hexyllithium, and cyclohexyllithium. From the standpoint that the ruthenium complex (3) has vapor pressure suitable as a CVD material or an ALD material, methyllithium, ethyllithium, propyllithium, isopropyllithium, butyllithium, isobutyllithium, sec-butyllithium, tert-butyllithium, etc. are preferred.

For the reason that the yield of the ruthenium complex (3) is high, production method 6 is preferably performed in an inert gas. Specific examples of the inert gas include helium, neon, argon, krypton, xenon, and nitrogen gas, with argon or nitrogen gas being preferred.

For the reason that the yield of the ruthenium complex (3) is high, production method 6 is preferably performed in an organic solvent. In the case of performing production method 6 in an organic solvent, specific examples of the organic solvent include an aliphatic hydrocarbon such as pentane, hexane, heptane, octane, cyclohexane, methylcyclohexane, ethylcyclohexane and petroleum ether, and an ether such as diethyl ether, diisopropyl ether, dibutyl ether, cyclopentyl methyl ether, cyclopentyl ethyl ether, tetrahydrofuran, dioxane and 1,2-dimethoxyethane. Of these organic solvents, one kind may be used alone, or a plurality of kinds may be mixed in an arbitrary ratio and used. In view of a high yield of the ruthenium complex (3), as the organic solvent, an ether is preferred, and diethyl ether and tetrahydrofuran are more preferred.

The method for obtaining the alkyllithium (11) includes the production methods described, for example, in Journal of the American Chemical Society, Vol. 108, page 7016 (1986), other than the purchase of a commercial product.

The molar ratio between the cationic arene complex (10) and the alkyllithium (11) when performing production method 6 is described below. Preferably, 1 mol or more of the alkyllithium (11) is used per mol of the cationic arene complex (10), whereby the ruthenium complex (3) can be efficiently produced.

In production method 6, the reaction temperature and the reaction time are not particularly limited, and general conditions employed by one skilled in the art when producing a metal complex may be used. As a specific example, a reaction temperature appropriately selected from a temperature range of −80° C. to 120° C. and a reaction time appropriately selected from the range of 10 minutes to 120 hours are employed, whereby the ruthenium complex (3) can be efficiently produced.

The ruthenium complex (3) produced by production method 6 may be purified by appropriately selecting and using a general purification method employed by one skilled in the art when purifying a metal complex. The purification method specifically includes filtration, extraction, centrifugation, decantation, distillation, sublimation, crystallization, column chromatography, etc.

The cationic arene complex (10) as a raw material of production method 6 can be produced according to the method described in Non-Patent Document 3, Angewandte Chemie International Edition, Vol. 46, page 4976, Supporting Information (2007), or Journal of the American Chemical Society, Vol. 111, page 1698 (1989), or the following production method 7. From the standpoint that the amount of the reaction agent used is small and the yield of the cationic arene complex (10) is high, the complex is preferably produced according to production method 7. Production method 7 is a method of reacting a ruthenocene derivative (12) and a benzene derivative (14) with a protonic acid H$^+$P$^-$ to produce a cationic arene complex (10).

Production Method 7:

[Chem. 15]

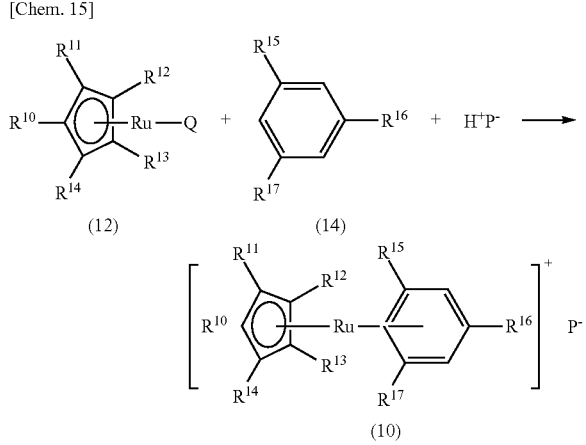

(wherein $R^{10}$ to $R^{17}$ have the same meanings as $R^{10}$ to $R^{17}$ in formula (3), and $P^-$ represents a counter anion.)

In formula (12), Q represents an $\eta^5$-2,4-dimethyl-2,4-pentadienyl ligand or an $\eta^5$-(unsubstituted or substituted)cyclopentadienyl ligand represented by formula (13):

[Chem. 16]

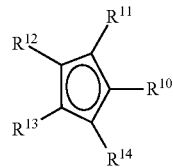

(13)

(wherein $R^{10}$ to $R^{14}$ have the same meanings as $R^{10}$ to $R^{14}$ in formula (3).)

Specific examples of the $\eta^5$-(unsubstituted or substituted) cyclopentadienyl ligand (13) include an $\eta^5$-cyclopentadienyl ligand, an $\eta^5$-methylcyclopentadienyl ligand, an $\eta^5$-ethylcyclopentadienyl ligand, an $\eta^5$-propylcyclopentadienyl ligand, an $\eta^5$-isopropylcyclopentadienyl ligand, an $\eta^5$-butylcyclopentadienyl ligand, an $\eta^5$-isobutylcyclopentadienyl ligand, an $\eta^5$-sec-butylcyclopentadienyl ligand, an $\eta^5$-tert-butylcyclopentadienyl ligand, an $\eta^5$-pentylcyclopentadienyl ligand, an $\eta^5$-cyclopentylcyclopentadienyl ligand, an $\eta^5$-hexylcyclopentadienyl ligand, an $\eta^5$-1,2-dimethylcyclopentadienyl ligand, an $\eta^5$-1,3-dimethylcyclopentadienyl ligand, an $\eta^5$-1,3-di(isopropyl)cyclopentadienyl ligand, an $\eta^5$-1,2,4-tri(isopropyl)cyclopentadienyl ligand, an $\eta^5$-1,3-di(tert-butyl)cyclopentadienyl ligand, and an $\eta^5$-1,2,3,4,5-pentamethylcyclopentadienyl ligand.

In view of availability of the ruthenocene derivative (12), Q is preferably an $\eta^5$-2,4-dimethyl-2,4-pentadienyl ligand, an $\eta^5$-cyclopentadienyl ligand, an $\eta^5$-methylcyclopentadienyl ligand, an $\eta^5$-ethylcyclopentadienyl ligand, an $\eta^5$-propylcyclopentadienyl ligand, an $\eta^5$-isopropylcyclopentadienyl ligand, an $\eta^5$-butylcyclopentadienyl ligand, an $\eta^5$-isobutylcyclopentadienyl ligand, an $\eta^5$-sec-butylcyclopentadienyl ligand or an $\eta^5$-tert-butylcyclopentadienyl ligand, more preferably an $\eta^5$-cyclopentadienyl ligand, an $\eta^5$-methylcyclopentadienyl ligand or an $\eta^5$-ethylcyclopentadienyl ligand.

Specific examples of the ruthenocene derivative (12) include bis($\eta^5$-cyclopentadienyl)ruthenium (($\eta^5$-$C_5H_5$)$_2$Ru), bis($\eta^5$-methylcyclopentadienyl)ruthenium (($\eta^5$-$C_5MeH_4$)$_2$Ru), bis($\eta^5$-ethylcyclopentadienyl)ruthenium (($\eta^5$-$C_5EtH_4$)$_2$Ru), bis($\eta^5$-propylcyclopentadienyl)ruthenium (($\eta^5$-$C_5PrH_4$)$_2$Ru), bis($\eta^5$-isopropylcyclopentadienyl)ruthenium (($\eta^5$-$C_5{}^iPrH_4$)$_2$Ru), bis($\eta^5$-butylcyclopentadienyl)ruthenium (($\eta^5$-$C_5BuH_4$)$_2$Ru), bis($\eta^5$-isobutylcyclopentadienyl)ruthenium (($\eta^5$-$C_5{}^iBuH_4$)$_2$Ru), bis($\eta^5$-sec-butylcyclopentadienyl)ruthenium (($\eta^5$-$C_5{}^sBuH_4$)$_2$Ru), bis($\eta^5$-tert-butylcyclopentadienyl)ruthenium (($\eta^5$-$C_5{}^tBuH_4$)$_2$Ru), bis($\eta^5$-pentylcyclopentadienyl)ruthenium (($\eta^5$-$C_5PeH_4$)$_2$Ru), bis($\eta^5$-cyclopentylcyclopentadienyl)ruthenium (($\eta^5$-$C_5{}^cPeH_4$)$_2$Ru), bis($\eta^5$-hexylcyclopentadienyl)ruthenium (($\eta^5$-$C_5HxH_4$)$_2$Ru), bis($\eta^5$-1,2-dimethylcyclopentadienyl)ruthenium (($\eta^5$-$C_5Me_2H_3$)$_2$Ru), bis($\eta^5$-1,3-dimethylcyclopentadienyl)ruthenium (($\eta^5$-$C_5Me_2H_3$)$_2$Ru), bis($\eta^5$-1,3-di(isopropyl)cyclopentadienyl)ruthenium (($\eta^5$-$C_5(^iPr)_2H_3$)$_2$Ru), bis($\eta^5$-1,2,4-tri(isopropyl)cyclopentadienyl)ruthenium (($\eta^5$-$C_5(^iPr)_3H_2$)$_2$Ru), bis($\eta^5$-1,3-di(tert-butyl)cyclopentadienyl)ruthenium (($\eta^5$-$C_5(^tBu)_2H_3$)$_2$Ru), bis($\eta^5$-1,2,3,4,5-pentamethylcyclopentadienyl)ruthenium (($\eta^5$-$C_5Me_5$)$_2$Ru), ($\eta^5$-cyclopentadienyl)($\eta^5$-2,4-dimethyl-2,4-pentadienyl)ruthenium (Ru($\eta^5$-$C_5H_5$)($\eta^5$-$CH_2C(Me)CHC(Me)CH_2$)), ($\eta^5$-2,4-dimethyl-2,4-pentadienyl)($\eta^5$-methylcyclopentadienyl)ruthenium (Ru($\eta^5$-$C_5MeH_4$)($\eta^5$-$CH_2C(Me)CHC(Me)CH_2$)), ($\eta^5$-2,4-dimethyl-2,4-pentadienyl)($\eta^5$-ethylcyclopentadienyl)ruthenium (Ru($\eta^5$-$C_5EtH_4$)($\eta^5$-$CH_2C(Me)CHC(Me)CH_2$)), ($\eta^5$-2,4-dimethyl-2,4-pentadienyl)($\eta^5$-propylcyclopentadienyl)ruthenium (Ru($\eta^5$-$C_5PrH_4$)($\eta^5$-$CH_2C(Me)CHC(Me)CH_2$)), ($\eta^5$-2,4-dimethyl-2,4-pentadienyl)($\eta^5$-isopropylcyclopentadienyl)ruthenium (Ru($\eta^5$-$C_5{}^iPrH_4$)($\eta^5$-$CH_2C(Me)CHC(Me)CH_2$)), ($\eta^5$-butylcyclopentadienyl)($\eta^5$-2,4-dimethyl-2,4-pentadienyl)ruthenium (Ru($\eta^5$-$C_5BuH_4$)($\eta^5$-$CH_2C(Me)CHC(Me)CH_2$)), ($\eta^5$-2,4-dimethyl-2,4-pentadienyl)($\eta^5$-isobutylcyclopentadienyl)ruthenium (Ru($\eta^5$-$C_5{}^iBuH_4$)($\eta^5$-$CH_2C(Me)CHC(Me)CH_2$)), ($\eta^5$-sec-butylcyclopentadienyl)($\eta^5$-2,4-dimethyl-2,4-pentadienyl)ruthenium (Ru($\eta^5$-$C_5{}^sBuH_4$)($\eta^5$-$CH_2C(Me)CHC(Me)CH_2$)), ($\eta^5$-tert-butylcyclopentadienyl)($\eta^5$-2,4-dimethyl-2,4-pentadienyl)ruthenium (Ru($\eta^5$-$C_5{}^tBuH_4$)($\eta^5$-$CH_2C(Me)CHC(Me)CH_2$)), ($\eta^5$-2,4-dimethyl-2,4-pentadienyl)($\eta^5$-pentylcyclopentadienyl)ruthenium (Ru($\eta^5$-$C_5PeH_4$)($\eta^5$-$CH_2C(Me)CHC(Me)CH_2$)), ($\eta^5$-cyclopentylcyclopentadienyl)($\eta^5$-2,4-dimethyl-2,4-pentadienyl)ruthenium (Ru($\eta^5$-$C_5{}^cPeH_4$)($\eta^5$-$CH_2C(Me)CHC(Me)CH_2$)), ($\eta^5$-2,4-dimethyl-2,4-pentadienyl)($\eta^5$-hexylcyclopentadienyl)ruthenium (Ru($\eta^5$-$C_5HxH_4$)($\eta^5$-$CH_2C(Me)CHC(Me)CH_2$)), ($\eta^5$-1,2-dimethylcyclopentadienyl)($\eta^5$-2,4-dimethyl-2,4-pentadienyl)ruthenium (Ru($\eta^5$-$C_5Me_2H_3$)($\eta^5$-$CH_2C(Me)CHC(Me)CH_2$)), ($\eta^5$-1,3-dimethylcyclopentadienyl)($\eta^5$-2,4-dimethyl-2,4-pentadienyl)ruthenium (Ru($\eta^5$-$C_5Me_2H_3$)($\eta^5$-$CH_2C(Me)CHC(Me)CH_2$)), ($\eta^5$-2,4-dimethyl-2,4-pentadienyl)($\eta^5$-1,3-di(isopropyl)cyclopentadienyl)ruthenium (Ru($\eta^5$-$C_5(^iPr)_2H_3$)($\eta^5$-$CH_2C(Me)CHC(Me)CH_2$)), ($\eta^5$-2,4-dimethyl-2,4-pentadienyl)($\eta^5$-1,2,4-tri(isopropyl)cyclopentadienyl)ruthenium (Ru($\eta^5$-$C_5(^iPr)_3H_2$)($\eta^5$-$CH_2C(Me)CHC(Me)CH_2$)), ($\eta^5$-1,3-di(tert-butyl)cyclopentadienyl)($\eta^5$-2,4-dimethyl-2,4-pentadienyl)ruthenium (Ru($\eta^5$-$C_5(^tBu)_2H_3$)($\eta^5$-$CH_2C(Me)CHC(Me)CH_2$)), and ($\eta^5$-2,4-dimethyl-2,4-pentadienyl)($\eta^5$-1,2,3,4,5-pentamethylcyclopentadienyl)ruthenium (Ru($\eta^5$-$C_5Me_5$)($\eta^5$-$CH_2C(Me)CHC(Me)CH_2$)).

Of these, bis($\eta^5$-cyclopentadienyl)ruthenium (($\eta^5$-$C_5H_5$)$_2$Ru), bis($\eta^5$-methylcyclopentadienyl)ruthenium (($\eta^5$-$C_5MeH_4$)$_2$Ru), bis($\eta^5$-ethylcyclopentadienyl)ruthenium (($\eta^5$-$C_5EtH_4$)$_2$Ru), bis($\eta^5$-propylcyclopentadienyl)ruthenium (($\eta^5$-$C_5PrH_4$)$_2$Ru), bis($\eta^5$-isopropylcyclopentadienyl)ruthenium (($\eta^5$-$C_5{}^iPrH_4$)$_2$Ru), bis($\eta^5$-butylcyclopentadienyl)ruthenium (($\eta^5$-$C_5BuH_4$)$_2$Ru), bis($\eta^5$-isobutylcyclopentadienyl)ruthenium (($\eta^5$-$C_5{}^iBuH_4$)$_2$Ru), bis($\eta^5$-sec-butylcyclopentadienyl)ruthenium (($\eta^5$-$C_5{}^sBuH_4$)$_2$Ru), bis($\eta^5$-tert-butylcyclopentadienyl)ruthenium (($\eta^5$-$C_5{}^tBuH_4$)$_2$Ru), ($\eta^5$-cyclopentadienyl)($\eta^5$-2,4-dimethyl-2,4-pentadienyl)ruthenium (Ru($\eta^5$-$C_5H_5$)($\eta^5$-$CH_2C(Me)CHC(Me)CH_2$)), ($\eta^5$-2,4-dimethyl-2,4-pentadienyl)($\eta^5$-methylcyclopentadienyl)ruthenium (Ru($\eta^5$-$C_5MeH_4$)($\eta^5$-$CH_2C(Me)CHC(Me)CH_2$)), ($\eta^5$-2,4-dimethyl-2,4-pentadienyl)($\eta^5$-ethylcyclopentadienyl)ruthenium (Ru($\eta^5$-$C_5EtH_4$)($\eta^5$-$CH_2C(Me)CHC(Me)CH_2$)), ($\eta^5$-2,4-dimethyl-2,4-pentadienyl)($\eta^5$-propylcyclopentadienyl)ruthenium (Ru($\eta^5$-$C_5PrH_4$)($\eta^5$-$CH_2C(Me)CHC(Me)CH_2$)), ($\eta^5$-2,4-dimethyl-2,4-pentadienyl)($\eta^5$-isopropylcyclopentadienyl)ruthenium (Ru($\eta^5$-$C_5{}^iPrH_4$)($\eta^5$-$CH_2C(Me)CHC(Me)CH_2$)), ($\eta^5$-butylcyclopentadienyl)($\eta^5$-2,4-dimethyl-2,4-pentadienyl)ruthenium (Ru($\eta^5$-$C_5BuH_4$)($\eta^5$-$CH_2C(Me)CHC(Me)CH_2$)), ($\eta^5$-2,4-dimethyl-2,4-pentadienyl)($\eta^5$-isobutylcyclopentadienyl)ruthenium (Ru($\eta^5$-$C_5{}^iBuH_4$)($\eta^5$-$CH_2C(Me)$ CHC(Me)CH$_2$)), ($\eta^5$-sec-butylcyclopentadienyl)($\eta^5$-2,4-dimethyl-2,4-pentadienyl)ruthenium (Ru($\eta^5$-C$_5{}^s$BuH$_4$)($\eta^5$-CH$_2$C(Me)CHC(Me)CH$_2$)), ($\eta^5$-tert-butylcyclopentadienyl)($\eta^5$-2,4-dimethyl-2,4-pentadienyl)ruthenium (Ru($\eta^5$-C$_5{}^t$BuH$_4$)($\eta^5$-CH$_2$C(Me)CHC(Me)CH$_2$)), etc. are preferred; bis($\eta^5$-cyclopentadienyl)ruthenium ($\eta^5$-C$_5$H$_5$)$_2$Ru), bis($\eta^5$-methylcyclopentadienyl)ruthenium ($\eta^5$-C$_5$MeH$_4$)$_2$Ru), bis($\eta^5$-ethylcyclopentadienyl)ruthenium ($\eta^5$-C$_5$EtH$_4$)$_2$Ru), bis($\eta^5$-propylcyclopentadienyl)ruthenium ($\eta^5$-C$_5$PrH$_4$)$_2$Ru), bis($\eta^5$-isopropylcyclopentadienyl)ruthenium ($\eta^5$-C$_5{}^i$PrH$_4$)$_2$Ru), bis($\eta^5$-butylcyclopentadienyl)ruthenium ($\eta^5$-C$_5$BuH$_4$)$_2$Ru), bis($\eta^5$-isobutylcyclopentadienyl)ruthenium ($\eta^5$-C$_5{}^i$BuH$_4$)$_2$Ru), bis($\eta^5$-sec-butylcyclopentadienyl)ruthenium ($\eta^5$-C$_5{}^s$BuH$_4$)$_2$Ru), bis($\eta^5$-tert-butylcyclopentadienyl)ruthenium ($\eta^5$-C$_5{}^t$BuH$_4$)$_2$Ru), etc. are more preferred; and bis($\eta^5$-cyclopentadienyl)ruthenium ($\eta^5$-C$_5$H$_5$)$_2$Ru), bis($\eta^5$-methylcyclopentadienyl)ruthenium ($\eta^5$-C$_5$MeH$_4$)$_2$Ru) and bis($\eta^5$-ethylcyclopentadienyl)ruthenium ($\eta^5$-C$_5$EtH$_4$)$_2$Ru) are still more preferred.

Specific examples of the benzene derivative (14) include benzene, 1,3,5-trimethylbenzene, 1,3,5-triethylbenzene, 1,3,5-tripropylbenzene, 1,3,5-tri(isopropyl)benzene, 1,3,5-butylbenzene, 1,3,5-tri(isobutyl)benzene, 1,3,5-tri(sec-butyl)benzene, and 1,3,5-tri(tert-butyl)benzene. In view of a high yield of the cationic arene complex (10), benzene or 1,3,5-trimethylbenzene is preferred.

The counter anion P$^-$ of the protonic acid that can be used in production method 7 includes, for example, a fluoro complex anion such as tetrafluoroborate ion (BF$_4{}^-$) and hexafluorophosphate ion (PF$_6{}^-$), a sulfonate ion such as trifluoromethanesulfonate ion (CF$_3$SO$_3{}^-$), sulfate ion (SO$_4{}^{2-}$) and hydrogen sulfate ion (HSO$_4{}^-$), and a halide ion such as chloride ion and bromide ion.

Specific examples of the protonic acid include a fluoro complex acid such as tetrafluoroboric acid and hexafluorophosphoric acid; a sulfonic acid such as sulfuric acid and trifluoromethanesulfonic acid; and a hydrogen halide such as hydrogen chloride. The protonic acid may form a complex with an ether such as dimethyl ether and diethyl ether. Examples of the protonic acid in the form of a complex include a tetrafluoroboric acid-dimethyl ether complex, a tetrafluoroboric acid-diethyl ether complex, and a hexafluorophosphoric acid-diethyl ether complex. In view of a high yield of the cationic arene complex (10), a tetrafluoroboric acid-diethyl ether complex, tetrafluoroboric acid, or trifluoromethanesulfonic acid is preferred.

As the protonic acid for use in production method 7, a fluoro complex acid produced in a reaction system by reacting a fluoro complex anion-containing salt with a strong acid may also be used. In this case, examples of the fluoro complex anion-containing salt that can be used include ammonium tetrafluoroborate, lithium tetrafluoroborate, sodium tetrafluoroborate, potassium tetrafluoroborate, ammonium hexafluorophosphate, lithium hexafluorophosphate, sodium hexafluorophosphate, and potassium hexafluorophosphate. Examples of the strong acid that can be used include sulfuric acid, methanesulfonic acid, trifluoromethanesulfonic acid, hydrogen chloride, and hydrogen bromide. Specific examples of the fluoro complex acid that can be produced in a reaction system include tetrafluoroboric acid and hexaluorophosphoric acid. In view of a high cost benefit and a high yield, any one of ammonium tetrafluoroborate, sodium tetrafluoroborate and ammonium hexafluorophosphate is preferably mixed with sulfuric acid and used.

Furthermore, as the protonic acid for use in production method 7, a fluoro complex acid produced in a reaction system by reacting boron trifluoride with a strong acid may also be used. In this case, examples of the strong acid that can be used include sulfuric acid, methanesulfonic acid, trifluoromethanesulfonic acid, hydrogen chloride, and hydrogen bromide.

The methods for obtaining the ruthenocene derivative (12) and the benzene derivative (14) are described below. The method for obtaining the ruthenocene derivative (12) includes the methods described, for example, in Organic Syntheses, Vol. 41, page 96 (1961), Organometallics, Vol. 8, page 298 (1989), and JP-A-2003-342286, other than the purchase of a commercial product. The method for obtaining the benzene derivative (14) includes the methods described, for example, in Tetrahedron, Vol. 68, page 6535 (2012), other than the purchase of a commercial product.

The molar ratio among the ruthenocene derivative (12), the benzene derivative (14) and the protonic acid used in production method 7 is described below. In view of a high yield of the cationic arene complex (10), 1 mol or more of the benzene derivative is preferably used per mol of the ruthenocene derivative. The preferable amount of the protonic acid used varies depending on the kind of the protonic acid. For example, in the case where the protonic acid is a monobasic acid, in view of a high yield, 1 mol or more of the protonic acid is preferably used per mol of the ruthenocene derivative, and in the case of a dibasic acid, 0.5 mol or more of the protonic acid is preferably used per mol of the ruthenocene derivative. In the case where a mixture of a fluoro complex anion-containing salt and a strong acid is used as the protonic acid, 1 mol or more of the fluoro complex anion-containing salt and from 0.5 to 2.0 mol of the strong acid are appropriately used per mol of the ruthenocene derivative, whereby the cationic arene complex (10) can be efficiently obtained.

For the reason that the yield of the cationic arene complex (10) is high, production method 7 is preferably performed in an inert gas. Specific examples of the inert gas include helium, neon, argon, krypton, xenon, and nitrogen gas, with argon or nitrogen gas being preferred.

For the reason that the yield of the cationic arene complex (10) is high, production method 7 is preferably performed in an organic solvent. In the case of performing production method 7 in an organic solvent, specific examples of the organic solvent include an aliphatic hydrocarbon such as pentane, hexane, heptane, octane, cyclohexane, methylcyclohexane, ethylcyclohexane and petroleum ether, an ether such as diethyl ether, diisopropyl ether, dibutyl ether, cyclopentyl methyl ether, cyclopentyl ethyl ether, tetrahydrofuran, dioxane and 1,2-dimethoxyethane, a ketone such as acetone, methyl ethyl ketone, 3-pentanone, cyclopentanone and cyclohexanone, an alcohol such as methanol, ethanol, propanol, isopropanol, tert-butanol and ethylene glycol, and a nitrile such as acetonitrile, propionitrile, butyronitrile, isobutyronitrile, cyclopropanecarbonitrile, pentylonitrile isopentylonitrile, 3-methylbutanenitrile, 2-methylbutanenitrile, pivalonitrile and cyclobutanecarbonitrile. Of these organic solvents, one kind may be used alone, or a plurality of kinds may be mixed in an arbitrary ratio and used. In view of a high yield of the cationic arene complex (10), as the organic solvent, diethyl ether, tetrahydrofuran, acetone, methanol and acetonitrile are preferred.

In production method 7, the reaction temperature and the reaction time are not particularly limited, and general conditions employed by one skilled in the art when producing a metal complex may be used. As a specific example, a reaction temperature appropriately selected from a temperature range of −80° C. to 150° C. and a reaction time appropriately selected from the range of 10 minutes to 120 hours are employed, whereby the cationic arene complex (10) can be efficiently produced.

The cationic arene complex (10) produced by production method 7 may be purified by appropriately selecting and using a general purification method employed by one skilled in the art when purifying a metal complex. The purification method specifically includes filtration, extraction, centrifugation, decantation, crystallization, etc.

The ruthenium complex (3) can also be produced by production method 8 of continuously performing production method 7 and production method 6. In this case, the cationic arene complex (10) produced by production method 7 may be used as a raw material for production in production method 6 without purifying it, or the cationic arene complex (10) that is purified by appropriately selecting and using a general purification method employed by one skilled in the art when purifying a metal complex may be used as a raw material for production in production method 6. Examples of the purification method include filtration, extraction, centrifugation, decantation, and crystallization.

The production method of a ruthenium-containing thin film characterized by using a ruthenium complex (1), (2) or (3a) is described in detail below.

The method for producing a ruthenium-containing thin film of the present invention is a method of vaporizing a ruthenium complex represented by formula (1), (2) or (3a) and decomposing the ruthenium complex on a substrate and includes normal technical means employed by one skilled in the art when producing a metal-containing thin film. Specific examples thereof include a vapor deposition method based on a chemical reaction, such as CVD method and ALD method, and a solution method such as dip coating method, spin coating method and inkjet method. In the description of the present invention, the vapor deposition method based on a chemical reaction encompasses technical means usually employed by one skilled in the art, for example, a CVD method such as thermal CVD method, plasma CVD method and optical CVD method, and an ALD method. In the case of producing a ruthenium-containing thin film by a vapor deposition method based on a chemical reaction, for the reason that a thin film is likely to be uniformly formed even on a substrate surface having a three-dimensional structure, a chemical vapor deposition method is preferred, and a CVD method or an ALD method is more preferred. The CVD method is more preferred in that the deposition rate is high, and the ALD method is more preferred in that the step coverage is good. For example, in the case of producing a ruthenium-containing thin film by a CVD method or an ALD method, the ruthenium complex (1), (2) or (3a) is vaporized and supplied to a reaction chamber, and the ruthenium complex (1) is decomposed on a substrate provided in the reaction chamber, whereby a ruthenium-containing thin film can be produced on the substrate. The method for decomposing the ruthenium complex (1), (2) or (3a) include normal technical means employed by one skilled in the art when producing a metal-containing thin film. Specifically, examples thereof include a method of reacting the ruthenium complex (1), (2) or (3a) with a reaction gas, and a method of causing heat, plasma, light, etc. to act on the ruthenium complex (1), (2) or (3a). By appropriately selecting and using such a decomposition method, a ruthenium-containing thin film can be produced. It is also possible to use a plurality of decomposition methods in combination. The method for supplying the ruthenium complex (1), (2) or (3a) to a reaction chamber includes, for example, bubbling and a liquid vaporization supply system but is not particularly limited.

The carrier gas and diluent gas when producing a ruthenium-containing thin film by a CVD method or an ALD method are preferably a rare gas such as helium, neon, argon, krypton and xenon, or a nitrogen gas, and among others, a nitrogen gas, helium, neon or argon is preferred for the economical reason. The flow rate of the carrier gas and diluent gas is appropriately adjusted according to the capacity of the reaction chamber, and the like. For example, in the case where the capacity of the reaction chamber is from 1 to 10 L, the flow rate of the carrier gas is not particularly limited and is preferably from 1 to 10,000 sccm for the economical reason. Here, sccm is a unit representing the flow rate of a gas, and in terms of an ideal gas, 1 sccm indicates that the gas is moving at a speed of 2.68 mmol/h.

The reaction gas when producing a ruthenium-containing thin film by a CVD method or an ALD method includes, for example, a reducing gas such as ammonia, hydrogen, monosilane and hydrazine, and an oxidizing gas such as oxygen, ozone, water vapor, hydrogen peroxide, laughter gas, hydrogen chloride, nitric acid gas, formic acid and acetic acid. From the standpoint that the restriction on the specification of a deposition apparatus is little and handling is easy, ammonia, hydrogen, oxygen, ozone and water vapor are preferred. In the case of producing a ruthenium-containing thin film under the conditions using, as the reaction gas, a reducing gas but not an oxidizing gas, ammonia is preferred in that the deposition rate of the ruthenium-containing thin film is high. The flow rate of the reaction gas is appropriately adjusted according to the reactivity of the material and the volume of the reaction chamber. For example, when the volume of the reaction chamber is from 1 to 10 L, the flow rate of the reaction gas is not particularly limited and is preferably from 1 to 10,000 sccm for the economical reason.

The substrate temperature when producing a ruthenium-containing thin film by a CVD method or an ALD method is appropriately selected according to use or non-use of heat, plasma, light, etc., the kind of the reaction gas, or the like. For example, in the case of using ammonia as the reaction gas without using light or plasma in combination, the substrate temperature is not particularly limited and is preferably from 200 to 1,000° C. for the economical reason. In view of a high deposition rate, the substrate temperature is preferably from 300 to 750° C., more preferably from 350 to 700° C. In addition, by appropriately using light, plasma, ozone, hydrogen peroxide, etc., the ruthenium-containing thin film can be produced in a temperature region of 200° C. or less.

As the ruthenium-containing thin film obtained by the production method of the present invention, for example, in the case of the ruthenium complex alone, a metallic ruthenium thin film, a ruthenium oxide thin film, a ruthenium nitride thin film, a ruthenium oxynitride thin film, etc. are obtained, and in the case of using the ruthenium complex in combination with other metallic materials, a ruthenium-containing composite thin film is obtained. For example, when the ruthenium complex is used in combination with a strontium material, an $SrRuO_3$ thin film is obtained. The strontium material includes, for example, strontium bis(dipivaloylmethanate), diethoxystrontium, strontium bis(1,1,1,5,5,5-hexafluoro-2,4-pentanedionate). In addition, when producing a ruthenium-containing composite thin oxide by a CVD method or an ALD method, the ruthenium complex (1), (2) or (3a) and other metallic materials may be supplied separately to the reaction chamber or may be mixed and then supplied.

The ruthenium complex (1a) may be formed into a ruthenium-containing thin film, similarly to the ruthenium complex (1).

By using the ruthenium-containing thin film of the present invention as a constituent member, a high-performance semiconductor device enhanced in the memory capacity or responsiveness can be produced. Examples of the semiconductor device includes a semiconductor memory device such as DRAM, FeRAM and ReRAM, and a field-effect transistor. Examples of the constituent member thereof include a capacitor electrode, a gate electrode, and copper wiring liner.

EXAMPLES

The present invention is described in greater detail below by referring to Examples, but the present invention is not limited thereto. Here, Me, Et, Bu and $^t$Bu stand for a methyl group, an ethyl group, a butyl group, and a tert-butyl group, respectively. The $^1$H and $^{13}$C NMR spectra were measured using VXR-500S NMR Spectrometer manufactured by Varian.

Example 1

[Chem. 17]

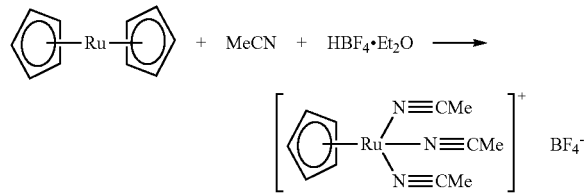

In an argon atmosphere, 2.35 g (14.5 mmol) of a tetrafluoroboric acid-diethyl ether complex was added at 0° C. to a suspension prepared by mixing 3.15 g (13.6 mmol) of bis($\eta^5$-cyclopentadienyl)ruthenium (($\eta^5$-C$_5$H$_5$)$_2$Ru) and 30 mL of acetonitrile. The resulting mixture was stirred at room temperature for 20 hours, and the solvent was then removed by distillation under reduced pressure. The remaining solid was washed with a mixture of dichloromethane and diethyl ether (dichloromethane:diethyl ether=1:13 (vol %)) to obtain [tris(acetonitrile)($\eta^5$-cyclopentadienyl)ruthenium(II)][tetrafluoroborate] ([Ru($\eta^5$-C$_5$H$_5$)(MeCN)$_3$][BF$_4$]) as a yellow solid (4.30 g, yield: 84%).

$^1$H-NMR (500 MHz, CDCl$_3$, δ): 4.21 (s, 5H), 2.43 (s, 9H).
$^{13}$C-NMR (125 MHz, CDCl$_3$, δ): 125.5, 68.8, 4.05.

Example 2

[Chem. 18]

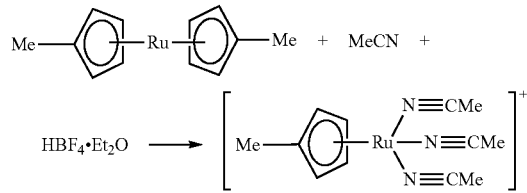

In an argon atmosphere, 4.28 g (26.4 mmol) of a tetrafluoroboric acid-diethyl ether complex was added at 0° C. to a solution prepared by mixing 6.52 g (25.1 mmol) of bis($\eta^5$-methylcyclopentadienyl)ruthenium (($\eta^5$-C$_5$MeH$_4$)$_2$Ru) and 50 mL of acetonitrile. The resulting mixture was stirred at room temperature for 20 hours, and the solvent was then removed by distillation under reduced pressure. The remaining solid was washed with a mixture of dichloromethane and diethyl ether (dichloromethane:diethyl ether=1:10 (vol %)) to obtain [tris(acetonitrile)($\eta^5$-methylcyclopentadienyl)ruthenium(II)][tetrafluoroborate] ([Ru($\eta^5$-C$_5$MeH$_4$)(MeCN)$_3$][BF$_4$]) as a yellow-brown solid (8.61 g, yield: 88%).

$^1$H-NMR (500 MHz, CDCl$_3$, δ): 4.13-4.16 (brs, 2H), 3.88-3.91 (brs, 2H), 2.42 (s, 9H), 1.70 (s, 3H).
$^{13}$C-NMR (125 MHz, CDCl$_3$, δ): 124.9, 92.2, 70.6, 63.5, 12.9, 4.0.

Example 3

[Chem. 19]

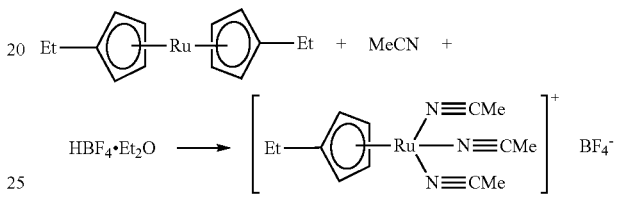

In an argon atmosphere, 2.55 g (15.7 mmol) of a tetrafluoroboric acid-diethyl ether complex was added at 0° C. to a solution prepared by mixing 4.31 g (15.0 mmol) of bis($\eta^5$-ethylcyclopentadienyl)ruthenium (($\eta^5$-C$_5$EtH$_4$)$_2$Ru) and 40 mL of acetonitrile. The resulting mixture was stirred at room temperature for 20 hours, and the solvent was then removed by distillation under reduced pressure. The remaining solid was washed with a mixture of dichloromethane and diethyl ether (dichloromethane:diethyl ether=1:10 (vol %)) to obtain [tris(acetonitrile)($\eta^5$-ethylcyclopentadienyl)ruthenium(II)][tetrafluoroborate] ([Ru($\eta^5$-C$_5$EtH$_4$)(MeCN)$_3$][BF$_4$]) as a yellow-brown solid (5.93 g, yield: 98%).

$^1$H-NMR (500 MHz, CDCl$_3$, δ): 4.10-4.15 (m, 2H), 3.89-3.94 (m, 2H), 2.40 (s, 9H), 2.03 (q, J=7.0 Hz, 2H), 1.07 (t, J=7.0 Hz, 3H).
$^{13}$C-NMR (125 MHz, CDCl$_3$, δ): 124.9, 96.7, 70.0, 63.4, 20.3, 13.6, 3.7.

Example 4

[Chem. 20]

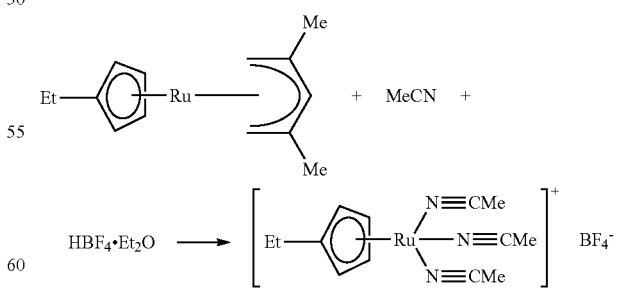

In an argon atmosphere, 5.98 g (36.9 mmol) of a tetrafluoroboric acid-diethyl ether complex was added at 0° C. to a solution prepared by mixing 10.2 g (35.2 mmol) of ($\eta^5$-2,4-dimethyl-2,4-pentadienyl)($\eta^5$-ethylcyclopentadienyl)ruthenium (Ru($\eta^5$-C$_5$EtH$_4$)($\eta^5$-CH$_2$C(Me)CHC(Me)CH$_2$)) and 40 mL of acetonitrile. The resulting mixture was stirred at room temperature for 20 hours, and the solvent was then removed by distillation under reduced pressure. The remaining solid was washed with a mixture of dichloromethane and diethyl ether (dichloromethane:diethyl ether=1:10 (vol %)) to obtain [tris(acetonitrile)($\eta^5$-ethylcyclopentadienyl)ruthenium(II)][tetrafluoroborate] ([Ru($\eta^5$-C$_5$EtH$_4$)(MeCN)$_3$][BF$_4$]) as a yellow-brown solid (14.1 g, yield: 99%). The thus-obtained [Ru($\eta^5$-C$_5$EtH$_4$)(MeCN)$_3$][BF$_4$] was measured for the $^1$H and $^{13}$C-NMR spectra, as a result, these spectra agreed with the spectra obtained in Example 3.

Example 5

[Chem. 21]

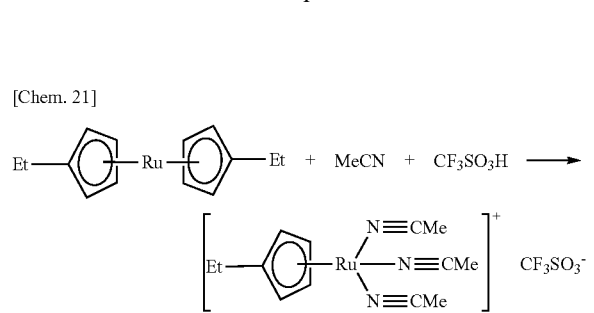

In an argon atmosphere, 603 mg (4.02 mmol) of trifluoromethanesulfonic acid was added at 0° C. to a solution prepared by dissolving 1.10 g (3.81 mmol) of bis($\eta^5$-ethylcyclopentadienyl)ruthenium (($\eta^5$-C$_5$EtH$_4$)$_2$Ru) in 5 mL of acetonitrile. The resulting mixture was stirred at room temperature for 20 hours, and the solvent was then removed by distillation under reduced pressure. The remaining solid was washed with diethyl ether to obtain [tris(acetonitrile)($\eta^5$-ethylcyclo-pentadienyl)ruthenium(II)][trifluoromethanesulfonate] ([Ru($\eta^5$-C$_5$EtH$_4$)(MeCN)$_3$][CF$_3$SO$_3$]) as a yellow-brown solid (1.61 g, yield: 90%).

$^1$H-NMR (500 MHz, CDCl$_3$, δ): 4.13-4.15 (m, 2H), 3.93-3.95 (m, 2H), 2.41 (s, 9H), 2.03 (q, J=7.0 Hz, 2H), 1.07 (t, J=7.0 Hz, 3H).

$^{13}$C-NMR (125 MHz, CDCl$_3$, δ): 124.9, 120.8 (q, J$_{C-F}$=318 Hz), 96.9, 70.2, 63.6, 20.4, 13.7, 4.04.

Example 6

[Chem. 22]

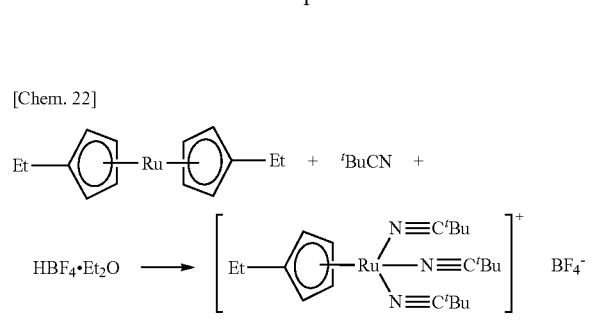

In an argon atmosphere, 903 mg (5.58 mmol) of a tetrafluoroboric acid-diethyl ether complex was added at 0° C. to a solution prepared by dissolving 1.53 g (5.32 mmol) of bis($\eta^5$-ethylcyclopentadienyl)ruthenium (($\eta^5$-C$_5$EtH$_4$)$_2$Ru) in 10 mL of pivalonitrile. The resulting mixture was stirred at room temperature for 20 hours, and the solvent was then removed by distillation under reduced pressure. The remaining solid was washed with a mixed solvent of tetrahydrofuran and hexane (tetrahydrofuran:hexane=1:10) to obtain [tris(pivalonitrile)($\eta^5$-ethylcyclopentadienyl)ruthenium(II)][tetrafluoroborate] ([Ru($\eta^5$-C$_5$EtH$_4$)($^t$BuCN)$_3$][BF$_4$]) as a red-brown oily matter (2.46 g, yield: 87%).

$^1$H-NMR (500 MHz, CDCl$_3$, δ): 4.16-4.18 (m, 2H), 3.94-3.96 (m, 2H), 2.05 (q, J=7.5 Hz, 2H), 1.45 (s, 27H), 1.10 (t, J=7.5 Hz, 3H).

$^{13}$C-NMR (125 MHz, CDCl$_3$, δ): 133.5, 97.8, 71.2, 63.7, 30.2, 28.3, 20.3, 13.6.

Example 7

[Chem. 23]

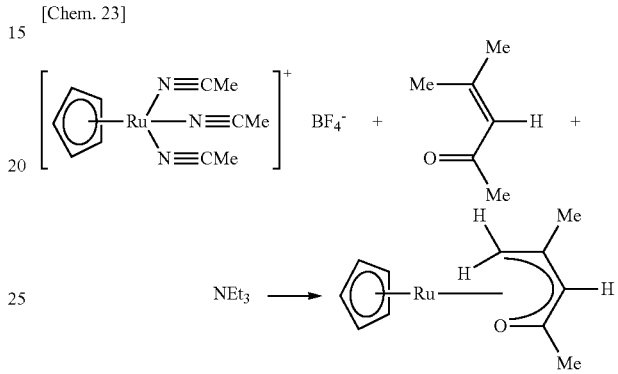

In an argon atmosphere, 13.0 g (132 mmol) of mesityl oxide and 4.22 g (41.7 mmol) of triethylamine were added to a suspension prepared by mixing 4.30 g (11.4 mmol) of [Ru($\eta^5$-C$_5$H$_5$)(MeCN)$_3$][BF$_4$] and 50 mL of hexane. The resulting mixture was stirred at room temperature for 20 minutes and then stirred at 50° C. for 10 hours. The reaction mixture was filtered, and the solvent was removed from the filtrate by distillation under reduced pressure. The remaining yellow solid was sublimated (heating temperature: 110° C./back pressure: 10 Pa) to obtain ($\eta^5$-cyclopentadienyl)($\eta^5$-2,4-dimethyl-1-oxa-2,4-pentadienyl)ruthenium (Ru($\eta^5$-C$_5$H$_5$)($\eta^5$-CH$_2$C(Me)CHC(Me)O)) as a yellow solid (1.27 g, yield: 42%).

$^1$H-NMR (500 MHz, CDCl$_3$, δ): 5.55 (s, 1H), 4.65 (s, 5H), 3.93 (s, 1H), 2.28 (s, 3H), 1.72 (s, 3H), 1.48 (s, 1H).

$^{13}$C-NMR (125 MHz, CDCl$_3$, δ): 134.4, 101.1, 84.0, 75.6, 51.9, 26.9, 24.3.

Example 8

[Chem. 24]

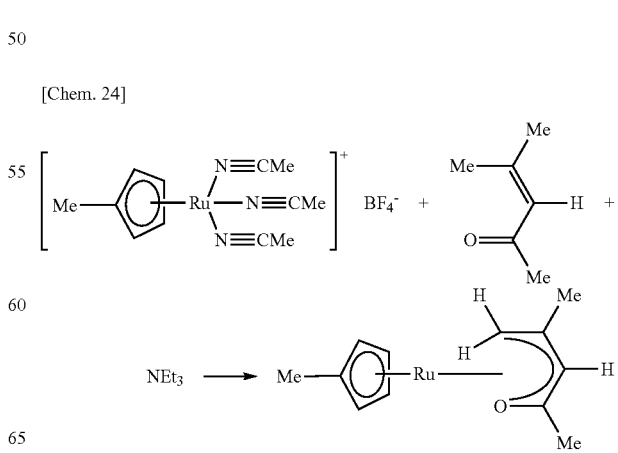

In an argon atmosphere, 8.61 g (22.1 mmol) of [Ru($\eta^5$-C$_5$MeH$_4$)(MeCN)$_3$][BF$_4$] was dissolved in 69.0 g (700 mmol) of mesityl oxide and the mixture was stirred at room temperature for 24 hours. Subsequently, 8.95 g (88.4 mmol) of triethylamine was added to the mixture at 0° C. and then the mixture was stirred at 50° C. for 8 hours. After removing the solvent by distillation under reduced pressure, the residue was added with 60 mL of hexane and vigorously stirred at room temperature. The produced suspension was filtered, and the solvent was removed from the filtrate by distillation under reduced pressure. The remaining solid was sublimated (heating temperature: 135° C./back pressure: 10 Pa) to obtain ($\eta^5$-2,4-dimethyl-1-oxa-2,4-pentadienyl)($\eta^5$-methylcyclopentadienyl)ruthenium (Ru($\eta^5$-C$_5$MeH$_4$)($\eta^5$-CH$_2$C(Me)CHC(Me)O)) as an orange solid (3.73 g, yield: 61%).

$^1$H-NMR (500 MHz, CDCl$_3$, δ): 5.43 (s, 1H), 4.56-4.61 (m, 2H), 4.49-4.52 (m, 2H), 3.79 (s, 1H), 2.25 (s, 3H), 1.80 (s, 3H), 1.72 (s, 3H), 1.55 (s, 1H).

$^{13}$C-NMR (125 MHz, CDCl$_3$, δ) 134.2, 101.4, 92.3, 84.3, 76.2, 76.1, 75.8, 74.6, 52.5, 26.6, 24.2, 13.5.

Example 9

[Chem. 25]

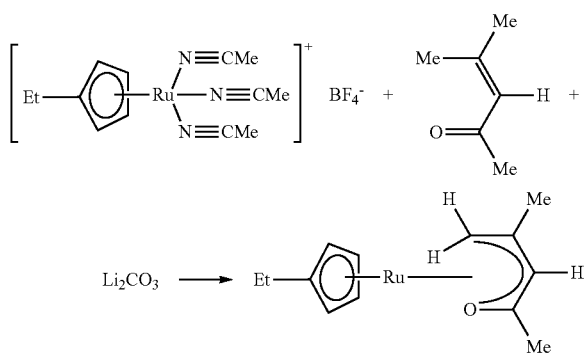

In an argon atmosphere, 1.49 g (3.68 mmol) of [Ru($\eta^5$-C$_5$EtH$_4$)(MeCN)$_3$][BF$_4$] was dissolved in 13.0 g (132 mmol) of mesityl oxide and after adding to the mixture 1.36 g (18.4 mmol) of lithium carbonate, the mixture was stirred at 50° C. for 8 hours. The solvent was removed by distillation under reduced pressure and thereafter, the residue was added with 60 mL of hexane and vigorously stirred at room temperature. The produced suspension was filtered, and the solvent was removed from the filtrate by distillation under reduced pressure. The remaining liquid was distilled under reduced pressure (distillation temperature: 88° C./back pressure: 5 Pa) to obtain ($\eta^5$-2,4-dimethyl-1-oxa-2,4-pentadienyl)($\eta^5$-ethylcyclopentadienyl)ruthenium (Ru($\eta^5$-C$_5$EtH$_4$)($\eta^5$-CH$_2$C(Me)CHC(Me)O)) as an orange liquid (0.93 g, yield: 86%).

$^1$H-NMR (500 MHz, CDCl$_3$, δ): 5.44 (s, 1H), 4.59-4.63 (m, 1H), 4.51-4.55 (m, 1H), 4.48-4.51 (m, 1H), 4.37-4.40 (m, 1H), 3.80 (s, 1H), 2.24 (s, 3H), 2.13 (q, J=7.5 Hz, 2H), 1.70 (s, 3H), 1.53 (s, 1H), 1.12 (t, J=7.5 Hz, 3H).

$^{13}$C-NMR (125 MHz, CDCl$_3$, δ): 134.2, 101.1, 100.3, 84.2, 75.7, 74.5, 74.4, 73.9, 52.3, 26.7, 24.1, 21.2, 14.8.

Example 10

[Chem. 26]

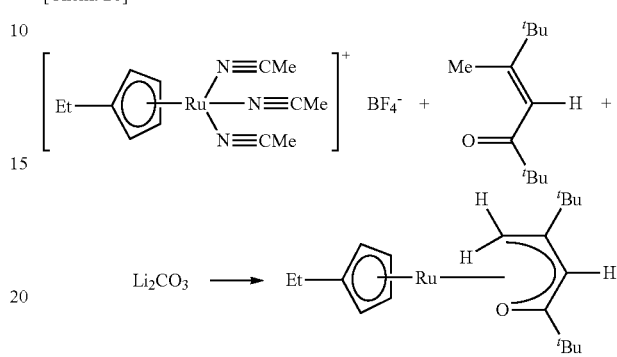

In an argon atmosphere, 2.60 g (35.2 mmol) of lithium carbonate and 11.0 g (60.6 mmol) of 2,2,5,6,6-pentamethyl-hept-4-en-3-one were added to a solution prepared by dissolving 2.84 g (7.03 mmol) of [Ru($\eta^5$-C$_5$EtH$_4$)(MeCN)$_3$][BF$_4$] in 20 mL of tetrahydrofuran. The resulting mixture was stirred at room temperature for 20 minutes and then stirred at 50° C. for 17 hours. After removing the solvent by distillation under reduced pressure, the residue was added with 150 mL of hexane and vigorously stirred at room temperature. The produced suspension was filtered, and the solvent was removed from the filtrate by distillation under reduced pressure to obtain ($\eta^5$-2,4-di-tert-butyl-1-oxa-2,4-pentadienyl)($\eta^5$-ethylcyclopentadienyl)ruthenium (Ru($\eta^5$-C$_5$EtH$_4$)($\eta^5$-CH$_2$C($^t$Bu)CHC($^t$Bu)O)) as an orange liquid (1.41 g, yield: 53%).

$^1$H-NMR (500 MHz, CDCl$_3$, δ): 5.68 (s, 1H), 4.74-4.78 (brs, 1H), 4.70-4.74 (brs, 1H), 4.36-4.40 (m, 1H), 4.07-4.10 (m, 1H), 4.01 (s, 1H), 2.34 (q, J=7.5 Hz, 2H), 1.40 (s, 1H), 1.26 (s, 9H), 1.23 (t, J=7.5 Hz, 3H), 1.03 (s, 9H).

$^{13}$C-NMR (125 MHz, CDCl$_3$, δ): 147.3, 116.0, 103.6, 76.5, 74.3, 72.5, 72.4, 71.4, 46.9, 37.4, 36.0, 31.0, 29.6, 21.9, 15.2.

Example 11

[Chem. 27]

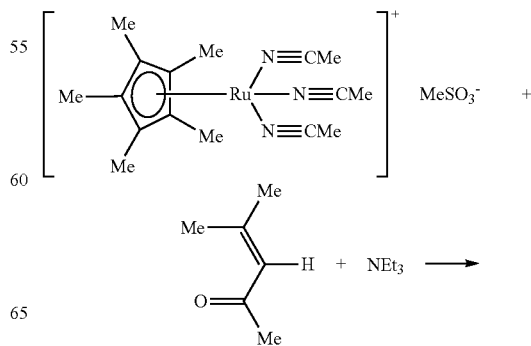

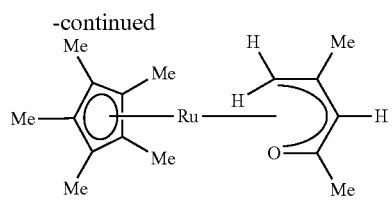

In an argon atmosphere, 5.81 g (59.2 mmol) of mesityl oxide and 1.82 g (18.0 mmol) of triethylamine were added to a suspension prepared by mixing 2.69 g (5.91 mmol) of [Ru($\eta^5$-C$_5$Me$_5$)(MeCN)$_3$][MeSO$_3$] and 30 mL of hexane. The resulting mixture was stirred at room temperature for 20 minutes and then stirred at 50° C. for 23 hours. After removing the solvent by distillation under reduced pressure, the residue was added with 150 mL of hexane and vigorously stirred at room temperature. The produced suspension was filtered, and the solvent was removed from the filtrate by distillation under reduced pressure. The remaining yellow solid was purified using column chromatography (alumina, tetrahydrofuran) to obtain ($\eta^5$-2,4-dimethyl-1-oxa-2,4-pentadienyl)($\eta^5$-1,2,3,4,5-pentamethylcyclopentadienyl)ruthenium (Ru($\eta^5$-C$_5$Me$_5$)($\eta^5$-CH$_2$C(Me)CHC(Me)O)) as a yellow solid (1.97 g, yield: 100%).

$^1$H-NMR (500 MHz, C$_6$D$_6$, δ): 4.88 (s, 1H), 3.17 (s, 1H), 2.04 (s, 3H), 1.75 (s, 15H), 1.64 (s, 1H), 1.61 (s, 3H).

$^{13}$C-NMR (125 MHz, C$_6$D$_6$, δ): 133.2, 101.7, 87.5, 84.6, 55.0, 25.2, 23.2, 10.7.

Example 12

[Chem. 28]

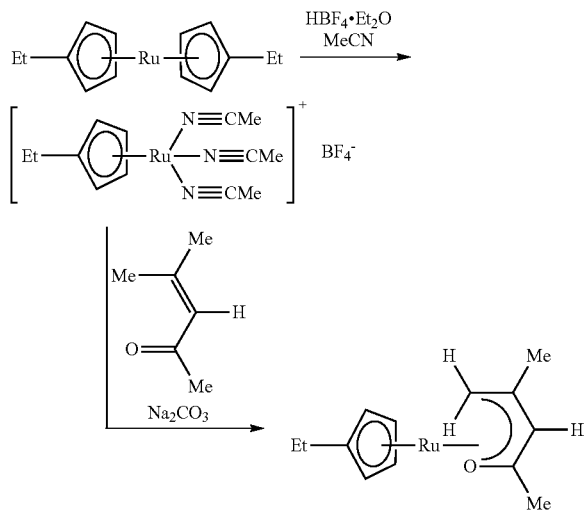

In an argon atmosphere, 2.88 g (10.0 mmol) of bis($\eta^5$-ethylcyclopentadienyl)ruthenium (($\eta^5$-C$_5$EtH$_4$)$_2$Ru) was dissolved in 30 mL of acetonitrile and after adding 1.70 g (10.5 mmol) of a tetrafluoroboric acid-diethyl ether complex to the mixture at 0° C., the mixture was stirred at room temperature for 8 hours. At this point, a part of the reaction mixture was sampled and analyzed using $^1$H-NMR, as a result, it was confirmed that [Ru($\eta^5$-C$_5$EtH$_4$)(MeCN)$_3$][BF$_4$] was produced. The solvent was removed from the reaction mixture by distillation under reduced pressure and after dissolving the remaining solid in 30 mL of acetone, 9.84 g (100 mmol) of mesityl oxide was added to the mixture at room temperature and the mixture was stirred at room temperature for 8 hours. Subsequently, 5.31 g (50.1 mmol) of sodium carbonate was added to the mixture and the mixture was stirred at 50° C. for 8 hours. After removing the solvent from the reaction mixture by distillation under reduced pressure, the residue was added with 60 mL of hexane and vigorously stirred at room temperature. The produced suspension was filtered, and the solvent was removed from the filtrate by distillation under reduced pressure. The remaining liquid was distilled under reduced pressure (distillation temperature: 88° C./back pressure: 5 Pa) to obtain ($\eta^5$-2,4-dimethyl-1-oxa-2,4-pentadienyl)($\eta^5$-ethylcyclopentadienyl)ruthenium (Ru($\eta^5$-C$_5$EtH$_4$)($\eta^5$-CH$_2$C(Me)CHC(Me)O)) as an orange liquid (2.06 g, yield: 70%). The thus-obtained Ru($\eta^5$-C$_5$EtH$_4$)($\eta^5$-CH$_2$C(Me)CHC(Me)O) was measured for $^1$H and $^{13}$C-NMR spectra, as a result, these spectra agreed with the spectra obtained in Example 9.

Example 13

[Chem. 29]

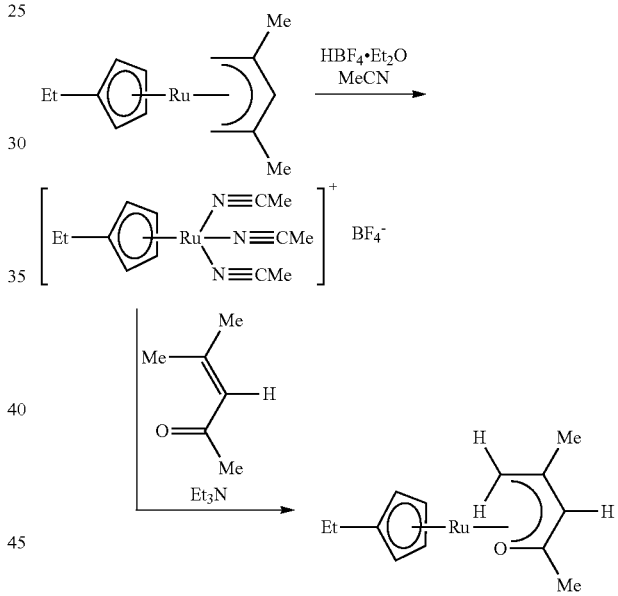

In an argon atmosphere, 3.25 g (11.2 mmol) of ($\eta^5$-2,4-dimethyl-2,4-pentadienyl)($\eta^5$-ethylcyclopentadienyl)ruthenium (Ru($\eta^5$-C$_5$EtH$_4$)($\eta^5$-CH$_2$C(Me)CHC(Me)CH$_2$)) was dissolved in 20 mL of acetonitrile and after adding 2.00 g (12.4 mmol) of a tetrafluoroboric acid-diethyl ether complex to the mixture at 0° C., the mixture was stirred at room temperature for 8 hours. At this point, a part of the reaction mixture was sampled and analyzed using $^1$H-NMR, as a result, it was confirmed that [Ru($\eta^5$-C$_5$EtH$_4$)(MeCN)$_3$][BF$_4$] was produced. The solvent was removed from the reaction mixture by distillation under reduced pressure and after dissolving the obtained residue in 20 mL of dichloromethane, 11.0 g (112 mmol) of mesityl oxide was added at room temperature and the mixture was stirred at room temperature for 8 hours. Subsequently, 1.25 g (12.4 mmol) of triethylamine was added to the mixture at 0° C. and the mixture was stirred at room temperature for 8 hours. After removing the solvent from the reaction mixture by distillation under reduced pressure, the residue was added with 60 mL of hexane and vigorously stirred at room temperature. The produced suspension was filtered, and the solvent was removed from the filtrate by distillation under reduced pressure. The remaining liquid was distilled under reduced pressure (distillation temperature: 88° C./back pressure: 5 Pa) to obtain ($\eta^5$-2,4-dimethyl-1-oxa-2,4-pentadienyl)($\eta^5$-ethylcyclopentadienyl)ruthenium ([Ru($\eta^5$-C$_5$EtH$_4$)($\eta^5$-CH$_2$C(Me)CHC(Me)O)]) as an orange liquid (1.90 g, yield: 58%). The thus-obtained Ru($\eta^5$-C$_5$EtH$_4$)($\eta^5$-CH$_2$C(Me)CHC(Me)O) was measured for $^1$H and $^{13}$C-NMR spectra, as a result, these spectra agreed with the spectra obtained in Example 9.

Production Example of Ruthenium-Containing Thin Film Using Ammonia as Reaction Gas Examples 14 to 17 and Comparative Examples 1 and 2

Ruthenium-containing thin films were produced by the thermal CVD method using the ruthenium complex (1) or ($\eta^5$-C$_5$EtH$_4$)$_2$Ru for the material. The apparatus used for the thin film production is sketched in FIG. 1. The deposition conditions are as shown in Table 6, and other conditions are as follows.

Total pressure in material container: 13.3 kPa, flow rate of carrier gas: 30 sccm, material feed rate: 0.012 sccm, flow rate of ammonia: 100 sccm, flow rate of diluent gas: 70 sccm, substrate: SiO$_2$/Si, and deposition time: 1 hour. As the carrier gas and diluent gas, argon was used. Here, the material feed rate to the reaction chamber can be determined based on the calculation formula: (flow rate of carrier gas×vapor pressure of material÷total pressure in material container).

In all of Examples 14 to 17, when the produced thin film was confirmed by X-ray fluorescence analysis, a characteristic X-ray based on ruthenium was detected. For the X-ray fluorescence analysis, 3370E manufactured by Rigaku Corporation was used. The measurement conditions were X-ray source: Rh, output: 50 kV 50 mA, and measurement diameter: 10 mm. The film thickness computed from the intensity of X-ray detected is shown in Table 6. The electrical properties of the ruthenium-containing thin film produced were measured by the four probe method, and the resistivity obtained is shown in Table 6. For the four probe method, LORESTA HP MCP-T410 manufactured by Mitsubishi Petrochemical Co., Ltd. was used.

The impurities contained in the film produced under the conditions of Example 15 (however, the deposition time was set to 2.5 hours) were quantitatively determined by the secondary ion mass spectrometry. For the secondary ion mass spectrometry, ADEPT1010 manufactured by PHI was used. The measurement conditions were primary ion species: Cs$^+$, primary ion acceleration voltage: 2 kV, secondary ion polarity: Positive, and charge compensation: E-gun.

C: 0.13 atm %, N: 0.08 atm %, O: 0.13 atm %.

Figure 2:
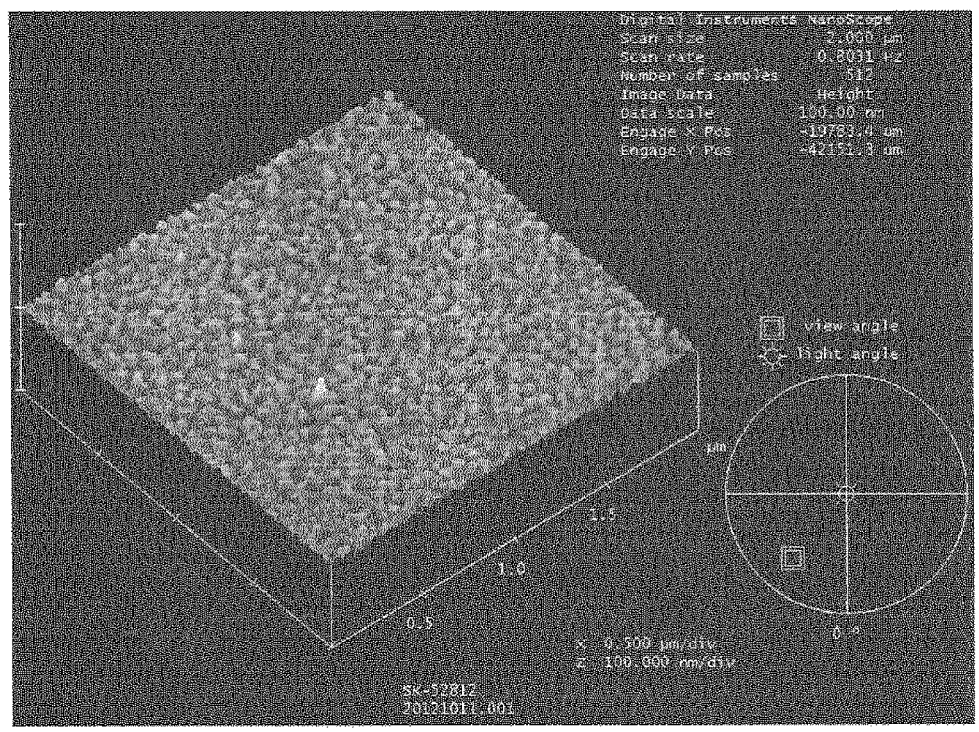
FIG. 2 is a view showing an atomic force microscope (hereinafter, AFM) image of the film obtained in Example 15.

The surface smoothness of the film produced under the conditions of Example 15 was evaluated by AFM, as a result, the arithmetic average roughness (Ra) of the film was 2.1 nm and the root-mean-square roughness (Rms) was 2.7 nm (FIG. 2). As the AFM, NanoScope IIa manufactured by Bruker•AXS was used. The measurement conditions were in tapping mode. The thin films produced in Comparative Examples 1 and 2 were confirmed by X-ray fluorescence analysis, as a result, a characteristic X-ray based on ruthenium was detected. The film thickness computed from the intensity of X-ray detected is shown in Table 6. The ruthenium-containing thin film produced was measured for electrical properties by the four probe method and found to be an insulating film.

[Table 20]

TABLE 6

|  | A | B | C | D | E | F |
|---|---|---|---|---|---|---|
| Example 14 | 1a-3 (Example 9) | 64 | 5.3 | 500 | 33 | 15 |
| Example 15 | 1a-3 (Example 9) | 64 | 5.3 | 450 | 29 | 15 |
| Example 16 | 1a-2 (Example 8) | 65 | 5.3 | 500 | 43 | 14 |
| Example 17 | 1a-2 (Example 8) | 65 | 5.3 | 450 | 17 | 38 |
| Comparative Example 1 | ($\eta^5$-C$_5$EtH$_4$)$_2$Ru | 62 | 5.3 | 500 | 47 | unmeasurable |
| Comparative Example 2 | ($\eta^5$-C$_5$EtH$_4$)$_2$Ru | 62 | 5.3 | 450 | 55 | unmeasurable |

A: Material,
B: material container temperature [° C.],
C: vapor pressure of material [Pa],
D: substrate temperature [° C.],
E: film thickness [nm],
F: resistivity [μΩ · cm].

Production Example of Ruthenium-Containing Thin Film Using Oxygen as Reaction Gas Examples 18 to 26 and Comparative Examples 3 and 4

Ruthenium-containing thin films were produced by the thermal CVD method using the ruthenium complex (1) or ($\eta^5$-C$_5$EtH$_4$)$_2$Ru for the material. The apparatus used for the thin film production is sketched in FIG. 1. The deposition conditions are as shown in Table 7, and other conditions are as follows.

Total pressure in material container: 13.3 kPa, flow rate of carrier gas: 30 sccm, material feed rate: 0.012 sccm, flow rate of oxygen: 0.16 sccm, flow rate of diluent gas: 169 sccm, substrate: SiO$_2$/Si, and deposition time: 1 hour. As the carrier gas and diluent gas, argon was used. In all of Examples 18 to 26, when the produced thin film was confirmed by X-ray fluorescence analysis, a characteristic X-ray based on ruthenium was detected. The film thickness computed from the intensity of X-ray detected is shown in Table 7. The electrical properties of the ruthenium-containing thin film produced were measured by the four probe method, and the resistivity obtained is shown in Table 7.

The thin films produced in Comparative Examples 3 and 4 were confirmed by X-ray fluorescence analysis, as a result, a characteristic X-ray based on ruthenium was detected in case of the thin film produced in Comparative Example 3, and a characteristic X-ray based on ruthenium was not detected in case of the thin film produced in Comparative Example 4. The film thickness computed from the intensity of X-ray detected is shown in Table 7. The ruthenium-containing thin film produced was measured for electrical properties by the four probe method, and the resistivity obtained is shown in Table 7.

[Table 21]

TABLE 7

|  | A | B | C | D | E | F |
|---|---|---|---|---|---|---|
| Example 18 | 1a-3 (Example 9) | 64 | 5.3 | 400 | 18 | 14 |
| Example 19 | 1a-3 (Example 9) | 64 | 5.3 | 300 | 17 | 321 |
| Example 20 | 1a-3 (Example 9) | 64 | 5.3 | 250 | 15 | 324 |
| Example 21 | 1a-3 (Example 9) | 64 | 5.3 | 225 | 7 | 568 |

TABLE 7-continued

| | A | B | C | D | E | F |
|---|---|---|---|---|---|---|
| Example 22 | 1a-2 (Example 8) | 65 | 5.3 | 400 | 28 | 10 |
| Example 23 | 1a-2 (Example 8) | 65 | 5.3 | 300 | 27 | 17 |
| Example 24 | 1a-2 (Example 8) | 65 | 5.3 | 250 | 23 | 31 |
| Example 25 | 1a-2 (Example 8) | 65 | 5.3 | 225 | 19 | 59 |
| Example 26 | 1a-2 (Example 8) | 65 | 5.3 | 200 | 6 | 296 |
| Comparative Example 3 | ($\eta^5$-$C_5EtH_4$)$_2$Ru | 62 | 5.3 | 400 | 26 | unmeasurable |
| Comparative Example 4 | ($\eta^5$-$C_5EtH_4$)$_2$Ru | 62 | 5.3 | 250 | 0 | unmeasurable |

A: Material,
B: material container temperature [° C.],
C: vapor pressure of material [Pa],
D: substrate temperature [° C.],
E: film thickness [nm],
F: resistivity [μΩ · cm].

Example 27

A ruthenium-containing thin film was produced by the thermal CVD method using the ruthenium complex (1) obtained in Example 9. The apparatus used for the thin film production is sketched in FIG. 1. The deposition conditions are as follows.

Material container temperature: 64° C., vapor pressure of material: 5.3 Pa, total pressure in material container: 3.3 kPa, substrate temperature: 350° C., flow rate of carrier gas: 30 sccm, material feed rate: 0.048 sccm, flow rate of ammonia: 30 sccm, substrate: $SiO_2$/Si, and deposition time: 5 hours. Argon was used as the carrier gas, and a diluent gas was not used.

Figure 3:
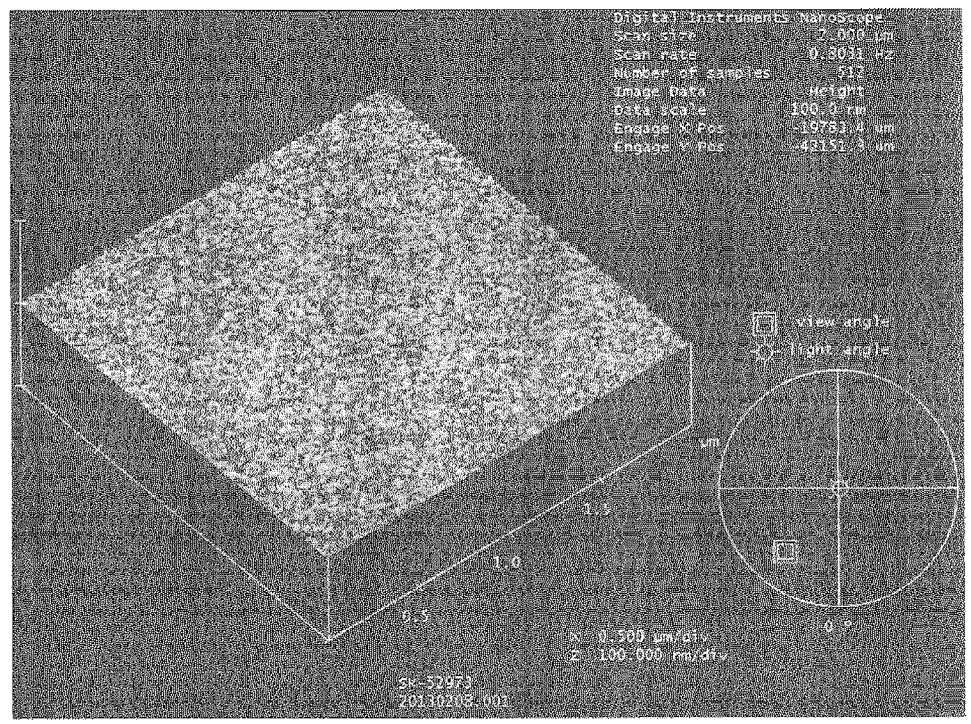
FIG. 3 is a view showing an AFM image of the film obtained in Example 27.

The produced thin film was confirmed by X-ray fluorescence analysis, as a result, a characteristic X-ray based on ruthenium was detected. The film thickness was computed from the intensity of X-ray detected and found to be 14 nm. The surface smoothness of the film obtained was evaluated by AFM, as a result, Ra of the film was 0.5 nm, and Rms was 0.6 nm (FIG. 3).

Comparative Example 5

A ruthenium-containing thin film was produced by the thermal CVD method using ($\eta^5$-$C_5EtH_4$)$_2$Ru for the material. The apparatus used for the thin film production is sketched in FIG. 1. The deposition conditions are as follows.

Material container temperature: 62° C., vapor pressure of material: 5.3 Pa, total pressure in material container: 3.3 kPa, substrate temperature: 350° C., flow rate of carrier gas: 30 sccm, material feed rate: 0.048 sccm, flow rate of ammonia: 30 sccm, substrate: $SiO_2$/Si, and deposition time: 5 hours. Argon was used as the carrier gas, and a diluent gas was not used.

The produced thin film was confirmed by X-ray fluorescence analysis, as a result, a characteristic X-ray based on ruthenium was not detected.

Example 28

A ruthenium-containing thin film was produced by the thermal CVD method using the ruthenium complex (1) obtained in Example 9. The apparatus used for the thin film production is sketched in FIG. 1. The deposition conditions are as follows.

Material container temperature: 100° C., vapor pressure of material: 69 Pa, total pressure in material container: 6.7 kPa, substrate temperature: 300° C., flow rate of carrier gas: 20 sccm, material feed rate: 0.21 sccm, flow rate of ammonia: 20 sccm, substrate: TaN/Ti/Si, and deposition time: 6 hours. Argon was used as the carrier gas, and a diluent gas was not used.

Figure 4:
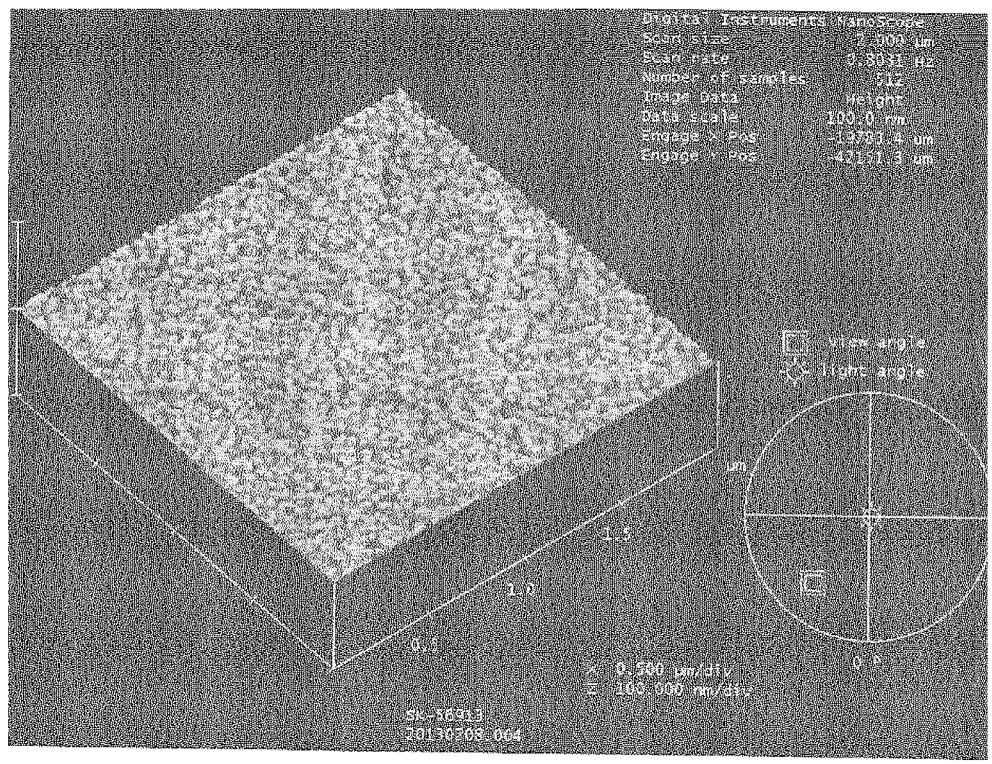
FIG. 4 is a view showing an AFM image of the film obtained in Example 28.

The produced thin film was confirmed by X-ray fluorescence analysis, as a result, a characteristic X-ray based on ruthenium was detected. The film thickness was computed from the intensity of X-ray detected and found to be 8 nm. The surface smoothness of the film obtained was evaluated by AFM, as a result, Ra of the film was 1.1 nm, and Rms was 1.4 nm (FIG. 4).

Comparative Example 6

A ruthenium-containing thin film was produced by the thermal CVD method using ($\eta^5$-$C_5EtH_4$)$_2$Ru for the material. The apparatus used for the thin film production is sketched in FIG. 1. The deposition conditions are as follows.

Material container temperature: 88° C., vapor pressure of material: 69 Pa, total pressure in material container: 6.7 kPa, substrate temperature: 300° C., flow rate of carrier gas: 20 sccm, material feed rate: 0.21 sccm, flow rate of ammonia: 20 sccm, substrate: TaN/Ti/Si, and deposition time: 6 hours. Argon was used as the carrier gas, and a diluent gas was not used.

The produced thin film was confirmed by X-ray fluorescence analysis, as a result, a characteristic X-ray based on ruthenium was not detected.

Examples 29 to 33

Ruthenium-containing thin films were produced by the thermal CVD method using the ruthenium complex (1) obtained in Example 9. The apparatus used for the thin film production is sketched in FIG. 1. The deposition conditions are as shown in Table 8, and other conditions are as follows.

Total pressure in material container: 6.7 kPa, flow rate of carrier gas: 30 sccm, material feed rate: 0.024 sccm, flow rate of ammonia: 50 sccm, flow rate of diluent gas: 20 sccm, substrate: $SiO_2$/Si, and deposition time: 2 hours (however, in Examples 29 and 30, 1 hour). As the carrier gas and diluent gas, argon was used.

In all of Examples 29 to 33, when the produced thin film was confirmed by X-ray fluorescence analysis, a characteristic X-ray based on ruthenium was detected. The film thickness computed from the intensity of X-ray detected is shown in Table 8. The electrical properties of the ruthenium-containing thin film produced were measured by the four probe method, and the resistivity obtained is shown in Table 8.

Figure 5:
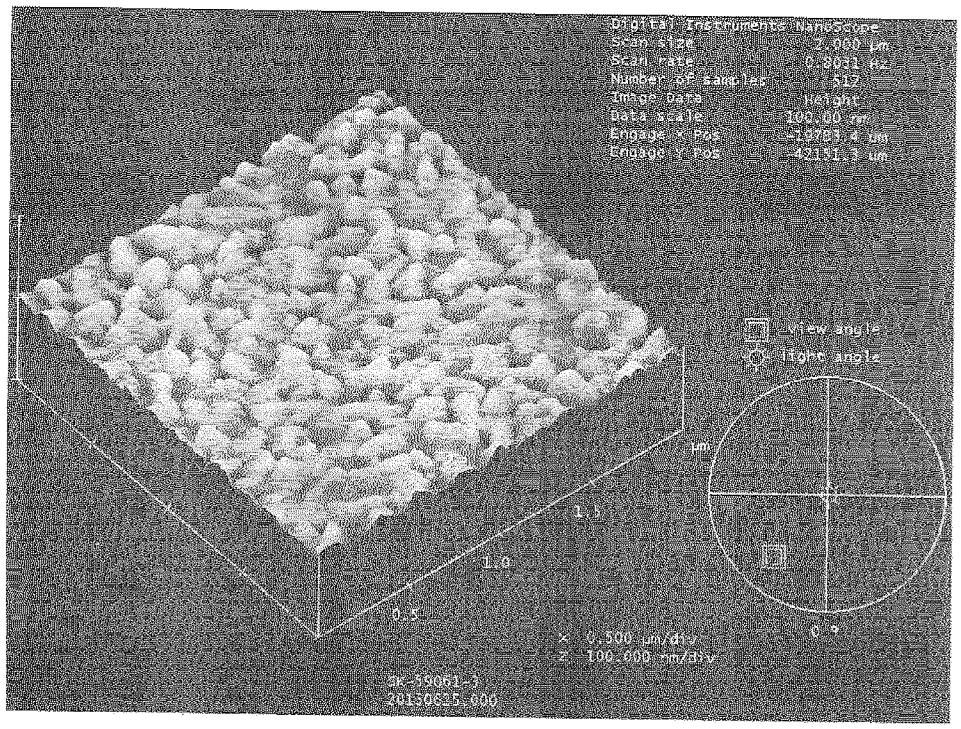
FIG. 5 is a view showing an AFM image of the film obtained in Example 29.

The surface smoothness of the film produced under the conditions of Example 29 was evaluated by AFM, as a result, Ra of the film was 3.6 nm, and Rms was 4.5 nm (FIG. 5). Furthermore, the impurities contained in the film produced under the conditions of Example 29 were quantitatively determined by the secondary ion mass spectrometry.

C: 0.13 atm %, N: 0.01 atm %, O: 0.13 atm %.

Figure 6:
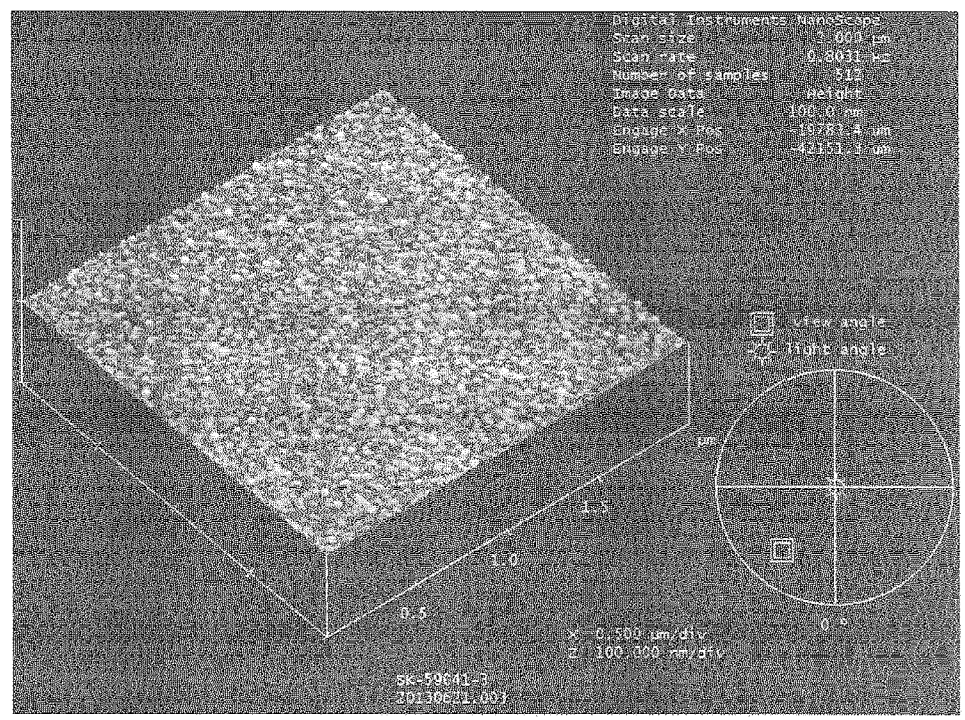
FIG. 6 is a view showing an AFM image of the film obtained in Example 31.

The surface smoothness of the film produced under the conditions of Example 31 was evaluated by AFM, as a result, Ra was 0.9 nm, and Rms was 1.2 nm (FIG. 6). Furthermore, the impurities contained in the film produced under the conditions of Example 31 were quantitatively determined by the secondary ion mass spectrometry.

C: 0.67 atm %, N: 0.07 atm %, O: 0.07 atm %.

Figure 7:
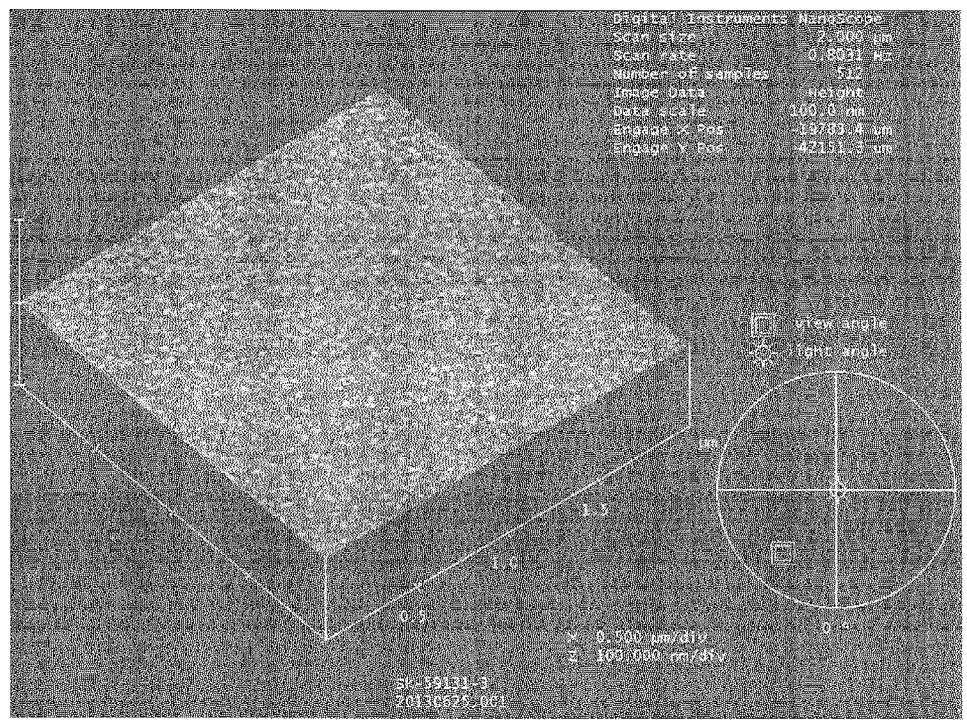
FIG. 7 is a view showing an AFM image of the film obtained in Example 33.

The surface smoothness of the film produced under the conditions of Example 33 was evaluated by AFM, as a result, Ra of the film was 0.4 nm, and Rms was 0.5 nm (FIG. 7).

[Table 22]

TABLE 8

|  | A | B | C | D | E | F |
|---|---|---|---|---|---|---|
| Example 29 | 1a-3 (Example 9) | 64 | 5.3 | 500 | 53 | 12 |
| Example 30 | 1a-3 (Example 9) | 64 | 5.3 | 450 | 55 | 11 |
| Example 31 | 1a-3 (Example 9) | 64 | 5.3 | 400 | 25 | 18 |
| Example 32 | 1a-3 (Example 9) | 64 | 5.3 | 375 | 12 | 68 |
| Example 33 | 1a-3 (Example 9) | 64 | 5.3 | 350 | 4 | 453 |

A: Material,
B: material container temperature [° C.],
C: vapor pressure of material [Pa],
D: substrate temperature [° C.],
E: film thickness [nm],
F: resistivity [μΩ · cm].

Examples 34 to 37

Ruthenium-containing thin films were produced by the thermal CVD method using the ruthenium complex (1) obtained in Example 9. The apparatus used for the thin film production is sketched in FIG. 1. The deposition conditions are as shown in Table 9, and other conditions are as follows.

Total pressure in material container: 6.7 kPa, flow rate of carrier gas: 30 sccm, material feed rate: 0.024 sccm, flow rate of hydrogen: 2 sccm, flow rate of diluent gas: 68 sccm, substrate: SiO$_2$/Si, and deposition time: 1 hour. As the carrier gas and diluent gas, argon was used.

In all of Examples 34 to 37, when the produced thin film was confirmed by X-ray fluorescence analysis, a characteristic X-ray based on ruthenium was detected. The film thickness computed from the intensity of X-ray detected is shown in Table 9. The electrical properties of the ruthenium-containing thin film produced were measured by the four probe method, and the resistivity obtained is shown in Table 9.

[Table 23]

TABLE 9

|  | A | B | C | D | E | F |
|---|---|---|---|---|---|---|
| Example 34 | 1a-3 (Example 9) | 64 | 5.3 | 500 | 20 | 313 |
| Example 35 | 1a-3 (Example 9) | 64 | 5.3 | 450 | 18 | 509 |
| Example 36 | 1a-3 (Example 9) | 64 | 5.3 | 400 | 13 | 1112 |
| Example 37 | 1a-3 (Example 9) | 64 | 5.3 | 375 | 3 | 633 |

A: Material,
B: material container temperature [° C.],
C: vapor pressure of material [Pa],
D: substrate temperature [° C.],
E: film thickness [nm],
F: resistivity [μΩ · cm].

The followings can be understood from these Examples. That is, as seen from Examples 14 to 17 and 27 to 37, the ruthenium complex (1) can produce a ruthenium-containing thin film even without using an oxidizing gas. It is also seen that by using the ruthenium complex (1) as the material, a metallic ruthenium film reduced in impurities can be produced even without using an oxidizing gas. Furthermore, it is seen that the ruthenium-containing thin film produced using the ruthenium complex (1) as the material has good electrical conductive properties. As seen from Examples 15, 27 and 28, by using the ruthenium complex (1) as the material, a metallic ruthenium film excellent in the surface smoothness can be produced even without using an oxidizing gas.

As seen from Examples 18 to 26, the ruthenium complex (1) can produce a ruthenium-containing thin film also when an oxidizing gas is used. Furthermore, comparison with Comparative Example 4 reveals that the ruthenium complex (1) can produce a ruthenium-containing thin film at a low temperature. Therefore, the ruthenium complex (1) is a useful material having a wide application range as a material for the thin film formation.

It is seen from comparison between Example 27 and Comparative Example 5 and comparison between Example 28 and Comparative Example 6 that the ruthenium complex (1) can produce a film excellent in the surface smoothness at a low temperature of 350° C. or less even without using an oxidizing gas.

Example 38

[Chem. 30]

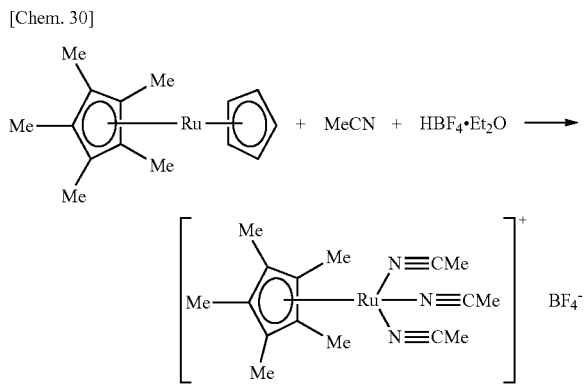

In an argon atmosphere, 3.21 g (19.8 mmol) of a tetrafluoroboric acid-diethyl ether complex was added at 0° C. to a suspension prepared by mixing 4.49 g (14.9 mmol) of (η$^5$-C$_5$H$_5$)(η$^5$-C$_5$Me$_5$)Ru that was synthesized by the method described in Organometallics, Vol. 5, page 2321 (1986), and 60 mL of acetonitrile. The resulting mixture was stirred at room temperature for 21 hours, and the solvent was then removed by distillation under reduced pressure. The remaining solid was washed with a mixture of dichloromethane and diethyl ether (dichloromethane:diethyl ether=1:13 (vol %)) to obtain [tris(acetonitrile)(η$^5$-1,2,3,4,5-pentamethylcyclopentadienyl)ruthenium(II)][tetrafluoroborate] ([Ru(η$^5$-C$_5$Me$_5$)(MeCN)$_3$][BF$_4$]) as a yellow solid (6.62 g, yield: 99%).

$^1$H-NMR (500 MHz, CDCl$_3$, δ): 2.30-2.46 (br, 9H), 1.58 (s, 15H).

Example 39

[Chem. 31]

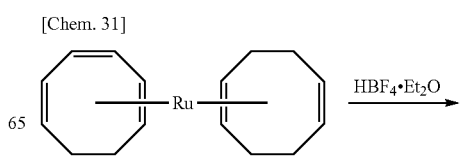

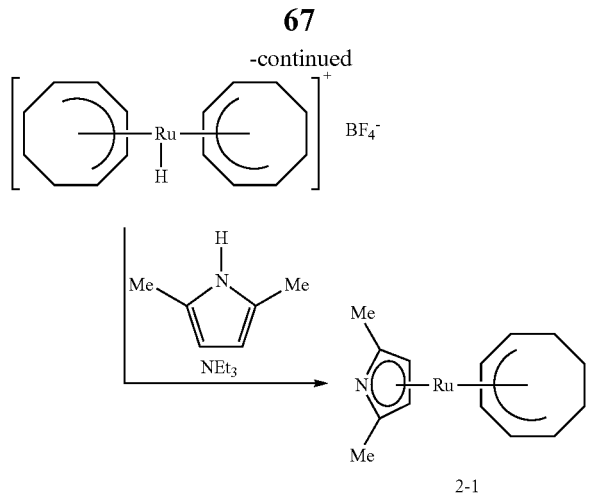

2-1

In an argon atmosphere, 6.39 g (39.5 mmol) of a tetrafluoroboric acid-diethyl ether complex was added at −78° C. to a solution prepared by mixing 11.8 g (37.6 mmol) of ($\eta^4$-1,5-cyclooctadiene)($\eta^6$-1,3,5-cyclooctatriene)ruthenium (Ru($\eta^4$-C$_4$H$_{12}$)($\eta^6$-C$_8$H$_{10}$)) that was synthesized according to the method described in Journal of Organometallic Chemistry, Vol. 272, page 179 (1984), and 120 mL of dichloromethane, and the mixture was stirred at 25° C. for 1 hour. At this point, a part of the reaction mixture was sampled and analyzed using $^1$H-NMR, as a result, it was confirmed that [RuH($\eta^5$-C$_8$H$_{11}$)$_2$][BF$_4$] was produced. Subsequently, 5.36 g (56.4 mmol) of 2,5-dimethylpyrrole was added at 25° C. and after stirring for 20 hours, 15.2 g (150.3 mmol) of triethylamine was added at 25° C. The resulting mixture was stirred for 22 hours, and the solvent was then removed by distillation under reduced pressure. The remaining liquid was distilled under reduced pressure (distillation temperature: 99° C./back pressure: 15 Pa) to obtain (1-5-$\eta^5$-cyclooctadienyl)($\eta^5$-2,5-dimethylpyrrolyl)ruthenium (Ru($\eta^5$-C$_8$H$_{11}$)($\eta^5$-NC$_4$Me$_2$H$_2$)) as a yellow-brown liquid (7.5 g, yield: 66%).

$^1$H-NMR (500 MHz, CDCl$_3$, δ): 5.76 (t, J=6.0 Hz, 1H), 5.09 (s, 2H), 4.00-4.10 (m, 2H), 3.43-3.55 (m, 2H), 2.02 (s, 6H), 1.69-1.76 (m, 2H), 1.25-1.36 (m, 2H), 1.03-1.12 (m, 1H), −0.21--0.097 (m, 1H).

$^{13}$C-NMR (125 MHz, CDCl$_3$, δ): 114.8, 102.1, 82.1, 75.3, 46.5, 29.3, 20.7, 15.1.

Examples 40 and 41 and Comparative Examples 7 and 8

Production Example of Ruthenium-Containing Thin Film Using Ammonia as Reaction Gas Ruthenium-containing thin films were produced by the thermal CVD method using the ruthenium complex (2) or Ru($\eta^5$-C$_5$EtH$_4$)$_2$ for the material. The apparatus used for the thin film production is sketched in FIG. 1. The deposition conditions are as shown in Table 10, and other conditions are as follows.

Total pressure in material container: 13.3 kPa, flow rate of carrier gas: 30 sccm, material feed rate: 0.012 sccm, flow rate of ammonia: 100 sccm, flow rate of diluent gas: 70 sccm, substrate: SiO$_2$/Si, and deposition time: 1 hour. As the carrier gas and diluent gas, argon was used. Here, the material feed rate to the reaction chamber can be determined based on the calculation formula: (flow rate of carrier gas×vapor pressure of material÷total pressure in material container).

In both of Examples 40 and 41, when the produced thin film was confirmed by X-ray fluorescence analysis, a characteristic X-ray based on ruthenium was detected. For the X-ray fluorescence analysis, 3370E manufactured by Rigaku Corporation was used. The measurement conditions were X-ray source: Rh, output: 50 kV 50 mA, and measurement diameter: 10 mm. The film thickness computed from the intensity of X-ray detected is shown in Table 10. The electrical properties of the ruthenium-containing thin film produced were measured by the four probe method, and the resistivity obtained is shown in Table 10. For the four probe method, LORESTA HP MCP-T410 manufactured by Mitsubishi Petrochemical Co., Ltd. was used.

The impurities contained in the film produced under the conditions of Example 41 (however, the deposition time was set to 1.5 hours) were quantitatively determined by the secondary ion mass spectrometry. For the secondary ion mass spectrometry, ADEPT1010 manufactured by PHI was used. The measurement conditions were primary ion species: Cs$^+$, primary ion acceleration voltage: 2 kV, secondary ion polarity: Positive, and charge compensation: E-gun.

C: 0.13 atm %, N: 0.27 atm %, O: 0.53 atm %.

Figure 8:
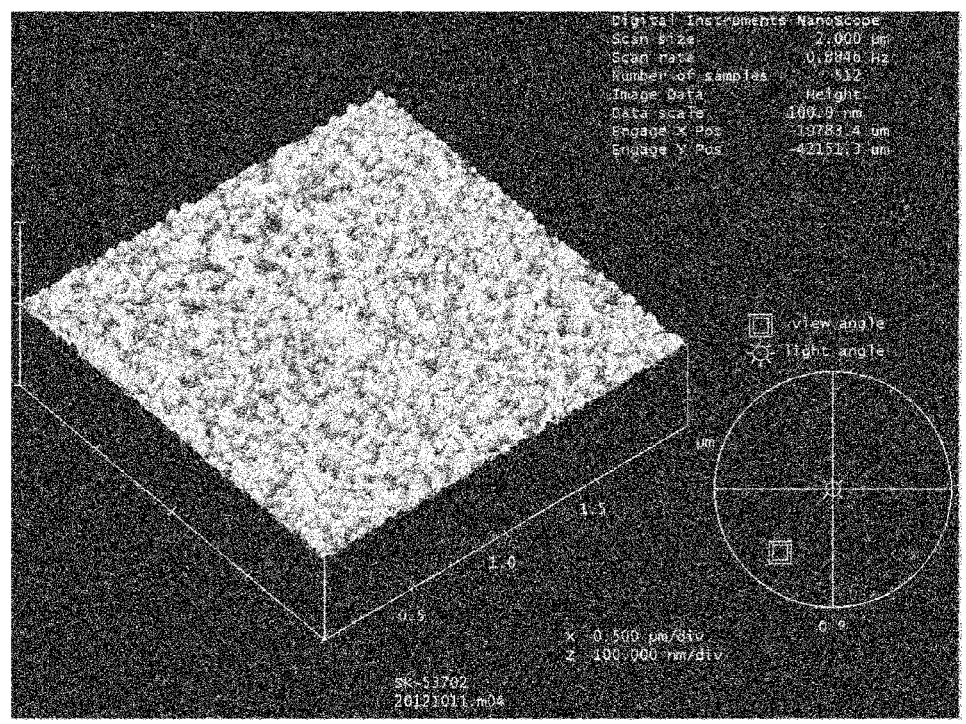
FIG. 8 is a view showing an atomic force microscope (hereinafter, AFM) image of the film obtained in Example 41.

The surface smoothness of the film produced obtained in Example 41 was evaluated by AFM, as a result, the arithmetic average roughness (Ra) of the film was 2.0 nm and the root-mean-square roughness (Rms) was 2.7 nm (FIG. 8). As the AFM, NanoScope Ma manufactured by Bruker•AXS was used. The measurement conditions were in tapping mode.

The thin films produced in Comparative Examples 7 and 8 were confirmed by X-ray fluorescence analysis, as a result, a characteristic X-ray based on ruthenium was detected. The film thickness computed from the intensity of X-ray detected is shown in Table 10. The ruthenium-containing thin film produced was measured for electrical properties by the four probe method and found to be an insulating film.

[Table 24]

TABLE 10

| | A | B | C | D | E | F |
|---|---|---|---|---|---|---|
| Example 40 | 2-1 (Example 39) | 83 | 5.3 | 500 | 49 | 46 |
| Example 41 | 2-1 (Example 39) | 83 | 5.3 | 450 | 39 | 22 |
| Comparative Example 7 | Ru($\eta^5$-C$_5$EtH$_4$)$_2$ | 62 | 5.3 | 500 | 47 | 10$^6$ or more |
| Comparative Example 8 | Ru($\eta^5$-C$_5$EtH$_4$)$_2$ | 62 | 5.3 | 450 | 55 | 10$^6$ or more |

A: Material,
B: material container temperature [° C.],
C: vapor pressure of material [Pa],
D: substrate temperature [° C.],
E: film thickness [nm],
F: resistivity [μΩ · cm].

Examples 42 to 45 and Comparative Examples 9 and 10

Production Example of Ruthenium-Containing Thin Film Using Oxygen as Reaction Gas Ruthenium-containing thin films were produced by the thermal CVD method using the ruthenium complex (2) or Ru($\eta^5$-C$_5$EtH$_4$)$_2$ for the material. The apparatus used for the thin film production is sketched in FIG. 1. The deposition conditions are as shown in Table 11, and other conditions are as follows.

Total pressure in material container: 13.3 kPa, flow rate of carrier gas: 30 sccm, material feed rate: 0.012 sccm, flow rate of oxygen: 0.16 sccm, flow rate of diluent gas: 169 sccm, substrate: SiO$_2$/Si, and deposition time: 1 hour. As the carrier gas and diluent gas, argon was used. In all of Examples 42 to 45, when the produced thin film was confirmed by X-ray fluorescence analysis, a characteristic X-ray based on ruthenium was detected. The film thickness computed from the intensity of X-ray detected is shown in Table 11. The electrical properties of the ruthenium-containing thin film produced were measured by the four probe method, and the resistivity obtained is shown in Table 11.

The thin films produced in Comparative Examples 9 and 10 were confirmed by X-ray fluorescence analysis, as a result, a characteristic X-ray based on ruthenium was detected in case of the thin film produced in Comparative Example 9 and a characteristic X-ray based on ruthenium was not detected in case of the thin film produced in Comparative Example 10. The film thickness computed from the intensity of X-ray detected is shown in Table 11. The electrical properties of the ruthenium-containing thin film produced were measured by the four probe method, and the resistivity obtained is shown in Table 11.

[Table 25]

TABLE 11

|  | A | B | C | D | E | F |
|---|---|---|---|---|---|---|
| Example 42 | 2-1 (Example 39) | 83 | 5.3 | 400 | 27 | 13 |
| Example 43 | 2-1 (Example 39) | 83 | 5.3 | 300 | 27 | 17 |
| Example 44 | 2-1 (Example 39) | 83 | 5.3 | 250 | 24 | 56 |
| Example 45 | 2-1 (Example 39) | 83 | 5.3 | 225 | 25 | 91 |
| Comparative Example 9 | Ru(η$^5$-C$_5$EtH$_4$)$_2$ | 262 | 5.3 | 400 | 26 | 10$^6$ or more |
| Comparative Example 10 | Ru(η$^5$-C$_5$EtH$_4$)$_2$ | 262 | 5.3 | 250 | 0 | unmeasurable |

A: Material,

B: material container temperature [° C.],

C: vapor pressure of material [Pa],

D: substrate temperature [° C.],

E: film thickness [nm],

F: resistivity [μΩ · cm].

The followings can be understood from these Examples. That is, as seen from Examples 40 and 41, the ruthenium complex (2) is a material capable of producing a ruthenium-containing thin film even without using an oxidizing gas. It is also seen that a ruthenium-containing thin film producing using the ruthenium complex (2) as the material has good electrical conductive properties. As seen from Example 41, by using the ruthenium complex (2) as the material, a metallic ruthenium film reduced in impurities can be produced even without using an oxidizing gas. In addition, as seen from Example 41, by using the ruthenium complex (2) as the material, a metallic ruthenium film excellent in the surface smoothness can be produced even without using an oxidizing gas.

As seen from Examples 42 to 45, the ruthenium complex (2) can produce a ruthenium-containing thin film also when an oxidizing gas is used. Furthermore, comparison with Comparative Examples 9 and 10 reveals that the ruthenium complex (2) is a material capable of producing a ruthenium-containing thin film at a low temperature and is a useful material having a wide application range as a material for the thin film formation.

Reference Example 1

[Chem. 32]

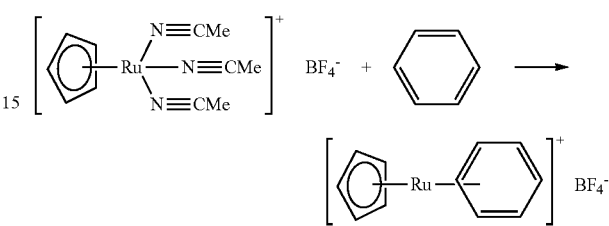

In an argon atmosphere, 1.84 g (23.6 mmol) of benzene was added to a solution prepared by mixing 5.98 g (15.9 mmol) of [tris(acetonitrile)(η$^5$-cyclopentadienyl)ruthenium(II)][tetrafluoroborate] ([Ru(η$^5$-C$_5$H$_5$)(MeCN)$_3$][BF$_4$]) and 40 mL of tetrahydrofuran. The resulting mixture was stirred at room temperature for 20 hours and then cooled to −78° C., and the produced solid was filtered to obtain [(η$^6$-benzene)(η$^5$-cyclopentadienyl)ruthenium(II)][tetrafluoroborate] ([Ru(η$^5$-C$_5$H$_5$)(η$^6$-C$_6$H$_6$)][BF$_4$]) as a yellow solid (3.27 g, yield: 62%).

$^1$H-NMR (500 MHz, CDCl$_3$, δ): 6.21 (s, 6H), 5.46 (s, 5H).

$^{13}$C-NMR (125 MHz, CDCl$_3$, δ): 86.1, 80.8.

Reference Example 2

[Chem. 33]

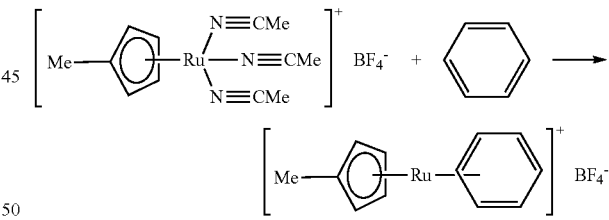

In an argon atmosphere, 2.19 g (28.1 mmol) of benzene was added to a solution prepared by mixing 9.01 g (23.1 mmol) of [tris(acetonitrile)(η$^5$-methylcyclopentadienyl)ruthenium(II)][tetrafluoroborate] ([Ru(η$^5$-C$_5$MeH$_4$)(MeCN)$_3$][BF$_4$]) and 40 mL of tetrahydrofuran. The resulting mixture was stirred at room temperature for 20 hours and then cooled to −78° C., and the produced solid was filtered to obtain [(η$^6$-benzene)(η$^5$-methylcyclopentadienyl)ruthenium(II)][tetrafluoroborate] ([Ru(η$^5$-C$_5$MeH$_4$)(η$^6$-C$_6$H$_6$)][BF$_4$]) as a brown solid (4.94 g, yield: 62%).

$^1$H-NMR (500 MHz, CDCl$_3$, δ): 6.15 (s, 6H), 5.40-5.43 (m, 2H), 5.30-5.33 (m, 2H), 2.08 (s, 3H).

$^{13}$C-NMR (125 MHz, CDCl$_3$, δ): 100.2, 86.4, 81.9, 80.2, 13.9.

Example 46

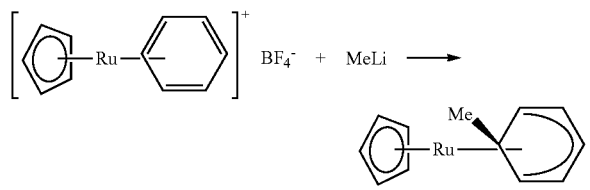

In an argon atmosphere, 9.8 mL (1.11 mol/L, 10.9 mmol) of a diethyl ether solution of methyllithium was added at −78° C. to a solution prepared by dissolving 3.27 g (9.88 mmol) of [Ru($\eta^5$-C$_5$H$_5$)($\eta^6$-C$_6$H$_6$)][BF$_4$] obtained in Reference Example 1 in 30 mL of tetrahydrofuran. The resulting mixture was stirred at room temperature for 20 hours and after removing the solvent by distillation under reduced pressure, the residue was added with 125 mL of hexane and vigorously stirred at room temperature. The produced suspension was filtered, and the solvent was removed from the filtrate by distillation under reduced pressure. The remaining solid was purified using column chromatography (alumina, hexane) to obtain ($\eta^5$-cyclopentadienyl)($\eta^5$-6-exo-methylcyclohexadienyl)ruthenium (Ru($\eta^5$-C$_5$H$_5$)($\eta^5$-C$_6$H$_6$Me)) as a yellow solid (850 mg, yield: 33%).

$^1$H-NMR (500 MHz, CDCl$_3$, δ): 5.64-5.72 (m, 1H), 4.73 (s, 5H), 4.28-4.38 (m, 2H), 2.83-2.92 (m, 2H), 2.28 (sext, J=6.4 Hz, 1H), 0.21 (d, J=6.5 Hz, 3H).

$^{13}$C-NMR (125 MHz, CDCl$_3$, δ): 79.5, 76.1, 74.9, 34.7, 32.5, 28.5.

Example 47

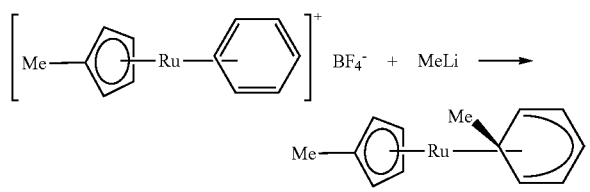

In an argon atmosphere, 14 mL (1.10 mol/L, 15.4 mmol) of a diethyl ether solution of methyllithium was added at −78° C. to a solution prepared by dissolving 4.94 g (14.3 mmol) of [Ru($\eta^5$-C$_5$MeH$_4$)($\eta^6$-C$_6$H$_6$)][BF$_4$] obtained in Reference Example 2 in 40 mL of tetrahydrofuran. The resulting mixture was stirred at room temperature for 21 hours and after removing the solvent by distillation under reduced pressure, the residue was added with 300 mL of hexane and vigorously stirred at room temperature. The produced suspension was filtered, and the solvent was removed from the filtrate by distillation under reduced pressure. The remaining liquid was purified using column chromatography (alumina, hexane) to obtain ($\eta^5$-6-exo-methylcyclohexadienyl)($\eta^5$-methylcyclopentadienyl)ruthenium (Ru($\eta^5$-C$_5$MeH$_4$)($\eta^5$-C$_6$H$_6$Me)) as a yellow liquid (860 mg, yield: 22%).

$^1$H-NMR (500 MHz, CDCl$_3$, δ): 5.59-5.62 (m, 1H), 4.74-4.77 (m, 2H), 4.51-4.54 (m, 2H), 4.24-4.29 (m, 2H), 2.71-2.76 (m, 2H), 2.30 (sext, J=6.4 Hz, 1H), 1.94 (s, 3H), 0.21 (d, J=6.5 Hz, 3H).

$^{13}$C-NMR (125 MHz, CDCl$_3$, δ): 92.0, 79.5, 76.7, 76.5, 74.2, 34.8, 33.8, 28.4, 14.6.

Example 48

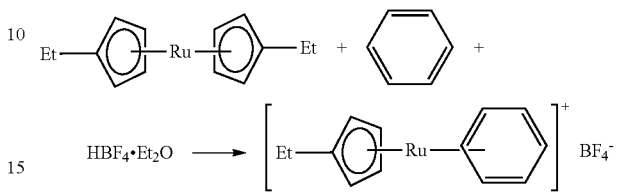

In an argon atmosphere, 2.63 g (33.7 mmol) of benzene was added to a solution prepared by mixing 835 mg (2.91 mmol) of bis($\eta^5$-ethylcyclopentadienyl)ruthenium (($\eta^5$-C$_5$EtH$_4$)$_2$Ru) produced by Aldrich and 7 mL of acetonitrile. To this solution, 516 mg (3.19 mmol) of a tetrafluoroboric acid-diethyl ether complex was added at 0° C. The resulting mixture was stirred at room temperature for 20 minutes and then stirred at 80° C. for 8 hours. The solvent was removed from the reaction mixture by distillation under reduced pressure, and the remaining solid was washed with a mixture of tetrahydrofuran and hexane (tetrahydrofuran:hexane=1:3) to obtain [($\eta^6$-benzene)($\eta^5$-ethylcyclopentadienyl)ruthenium (II)][tetrafluoroborate] ([Ru($\eta^5$-C$_5$EtH$_4$)($\eta^6$-C$_6$H$_6$)][BF$_4$]) as a yellow-brown solid (1.02 g, yield: 98%).

$^1$H-NMR (500 MHz, CDCl$_3$, δ): 6.15 (s, 6H), 5.36-5.40 (m, 2H), 5.30-5.34 (m, 2H), 2.33 (q, J=7.5 Hz, 2H), 1.09 (t, J=7.5 Hz, 3H).

$^{13}$C-NMR (125 MHz, CDCl$_3$, δ): 106.9, 86.2, 80.3, 80.0, 21.0, 14.5.

Example 49

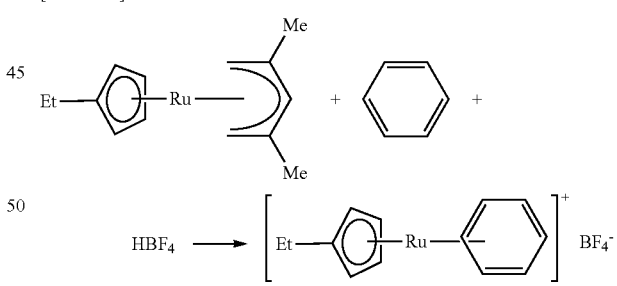

In an argon atmosphere, 7.5 g (96.0 mmol) of benzene was added to a solution prepared by mixing 20.2 g (69.6 mmol) of ($\eta^5$-2,4-dimethyl-2,4-pentadienyl)($\eta^5$-ethylcyclopentadienyl)ruthenium (Ru($\eta^5$-C$_5$EtH$_4$)($\eta^5$-CH$_2$C(Me)CHC(Me)CH$_2$)) that was synthesized according to the method described in JP-A-2003-342286, and 80 mL of tetrahydrofuran. To this solution, 15 mL (42%, 99.0 mmol) of an aqueous tetrafluoroboric acid solution was added at −78° C. The resulting mixture was stirred at room temperature for 20 hours and then cooled to −78° C., and the produced solid was filtered to obtain [($\eta^6$-benzene)($\eta^5$-ethylcyclopentadienyl)ruthenium(II)][tetrafluoroborate] ([Ru($\eta^5$-C$_5$EtH$_4$)($\eta^6$-C$_6$H$_6$)][BF$_4$]) as a white solid (19.4 g, yield: 78%). The [Ru ($\eta^5$-C$_5$EtH$_4$)($\eta^6$-C$_6$H$_6$)][BF$_4$] obtained was measured for the $^1$H and $^{13}$C-NMR spectra, as a result, these spectra agreed with the spectra obtained in Example 48.

Example 50

[Chem. 38]

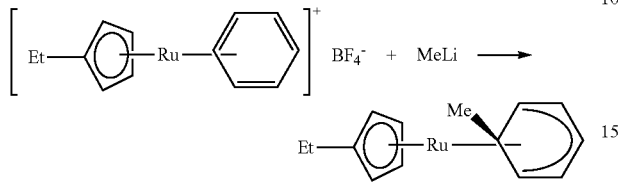

In an argon atmosphere, 47 mL (1.10 mol/L, 51.7 mmol) of a diethyl ether solution of methyllithium was added at −78° C. to a solution prepared by dissolving 16.4 g (45.7 mmol) of [Ru($\eta^5$-C$_5$EtH$_4$)($\eta^6$-C$_6$H$_6$)][BF$_4$] obtained in Example 49 in 140 mL of tetrahydrofuran. The resulting mixture was stirred at room temperature for 20 hours and after removing the solvent by distillation under reduced pressure, the residue was added with 200 mL of hexane and vigorously stirred at room temperature. The produced suspension was filtered, and the solvent was removed from the filtrate by distillation under reduced pressure. The remaining liquid was purified using column chromatography (alumina, hexane) and then distilled under reduced pressure (distillation temperature: 80° C./back pressure: 1.5 Pa) to obtain ($\eta^5$-ethylcyclopentadienyl)($\eta^5$-6-exo-methylcyclohexadienyl)ruthenium (Ru($\eta^5$-C$_5$EtH$_4$)($\eta^5$-C$_6$H$_6$Me)) as a yellow liquid (5.33 g, yield: 41%).

$^1$H-NMR (500 MHz, CDCl$_3$, δ): 5.60-5.65 (m, 1H), 4.70-4.73 (m, 2H), 4.55-4.58 (m, 2H), 4.26-4.31 (m, 2H), 2.74-2.79 (m, 2H), 2.30 (sext, J=6.5 Hz, 1H), 2.25 (q, J=7.5 Hz, 2H), 1.09 (t, J=7.5 Hz, 3H), 0.20 (d, J=6.5 Hz, 3H).

$^{13}$C-NMR (125 MHz, CDCl$_3$, δ): 99.8, 79.4, 76.6, 74.8, 73.9, 34.8, 33.4, 28.4, 22.0, 15.0.

Example 51

[Chem. 39]

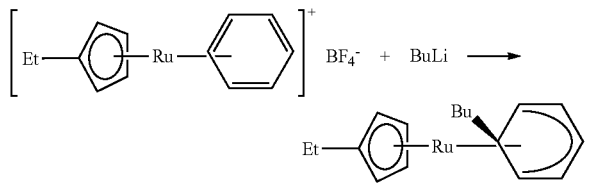

In an argon atmosphere, 7.0 mL (2.69 mol/L, 18.8 mmol) of a hexane solution of n-butyllithium was added at −78° C. to a solution prepared by dissolving 6.16 g (17.2 mmol) of [Ru($\eta^5$-C$_5$EtH$_4$)($\eta^6$-C$_6$H$_6$)][BF$_4$] obtained in Example 49 in 50 mL of tetrahydrofuran. The resulting mixture was stirred at room temperature for 20 hours and after removing the solvent by distillation under reduced pressure, the residue was added with 125 mL of hexane and vigorously stirred at room temperature The produced suspension was filtered, and the solvent was removed from the filtrate by distillation under reduced pressure. The remaining liquid was purified using column chromatography (alumina, hexane) and then distilled under reduced pressure (distillation temperature: 112° C./back pressure: 37 Pa) to obtain ($\eta^5$-ethylcyclopentadienyl)($\eta^5$-6-exo-butylcyclohexadienyl)ruthenium (Ru($\eta^5$-C$_5$EtH$_4$)($\eta^5$-C$_6$H$_6$Bu)) as a yellow liquid (3.66 g, yield: 65%).

$^1$H-NMR (500 MHz, CDCl$_3$, δ): 5.57-5.68 (m, 1H), 4.72 (brs, 2H), 4.57 (brs, 2H), 4.24-4.37 (m, 2H), 2.73-2.83 (m, 2H), 2.25 (q, J=7.5 Hz, 2H), 2.14-2.21 (m, 1H), 1.04-1.16 (m, 5H), 0.92-1.01 (m, 2H), 0.78 (t, J=7.5 Hz, 3H), 0.45-0.54 (m, 2H).

$^{13}$C-NMR (125 MHz, CDCl$_3$, δ): 99.8, 79.6, 76.7, 74.9, 73.9, 42.3, 40.1, 32.2, 26.3, 22.7, 22.0, 15.0, 14.3.

Example 52

[Chem. 40]

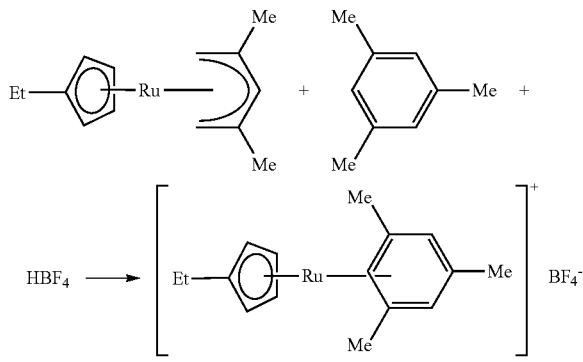

In an argon atmosphere, 515 mg (4.28 mmol) of 1,3,5-trimethylbenzene was added to a solution prepared by mixing 1.01 g (3.50 mmol) of ($\eta^5$-2,4-dimethyl-2,4-pentadienyl)($\eta^5$-ethylcyclopentadienyl)ruthenium (Ru($\eta^5$-C$_5$EtH$_4$)($\eta^5$-CH$_2$C(Me)CHC(Me)CH$_2$)) that was synthesized according to the method described in JP-A-2003-342286, and 10 mL of tetrahydrofuran. To this solution, 0.6 mL (42%, 3.96 mmol) of an aqueous tetrahydrofluoroboric acid solution was added at −78° C. The resulting mixture was stirred at room temperature for 3 days and then cooled to −78° C., and the produced solid was filtered to obtain [($\eta^5$-ethylcyclopentadienyl)($\eta^6$-1,3,5-trimethylbenzene)ruthenium(II)][tetrafluoroborate] ([Ru($\eta^5$-C$_5$EtH$_4$)($\eta^6$-C$_6$Me$_3$H$_3$)][BF$_4$]) as a white solid (717 mg, yield: 51%).

$^1$H-NMR (500 MHz, CDCl$_3$, δ): 6.00 (s, 3H), 5.11-5.20 (m, 4H), 2.31 (s, 9H), 2.23 (q, J=7.5 Hz, 2H), 1.12 (t, J=7.5 Hz, 3H).

$^{13}$C-NMR (125 MHz, CDCl$_3$, δ): 104.8, 101.1, 87.5, 80.9, 80.4, 20.5, 20.0, 14.7.

Example 53

[Chem. 41]

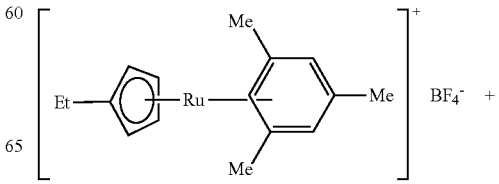

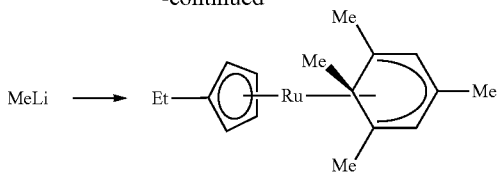

In an argon atmosphere, 1.8 mL (1.10 mol/L, 1.98 mmol) of a diethyl ether solution of methyllithium was added at −78° C. to a solution prepared by dissolving 717 mg (1.79 mmol) of [Ru($\eta^5$-C$_5$EtH$_4$)($\eta^6$-C$_6$Me$_3$H$_3$)][BF$_4$] obtained in Example 52 in 10 mL of tetrahydrofuran. The resulting mixture was stirred at room temperature for 16 hours and after removing the solvent by distillation under reduced pressure, the residue was added with 20 mL of tetrahydofuran and vigorously stirred at room temperature. The produced suspension was filtered, and the solvent was removed from the filtrate by distillation under reduced pressure. The remaining liquid was purified using column chromatography (alumina, tetrahydrofuran) and then distilled under reduced pressure (distillation temperature: 97° C./back pressure: 29 Pa) to obtain ($\eta^5$-ethylcyclopentadienyl)($\eta^5$-1,3,5,6-exo-tetramethylcyclohexadienyl)ruthenium (Ru($\eta^5$-C$_5$EtH$_4$)($\eta^5$-C$_6$H$_3$Me$_4$)) as a yellow liquid (382 mg, yield: 65%).

$^1$H-NMR (500 MHz, CDCl$_3$, δ): 4.38-4.41 (m, 2H), 4.36-4.38 (m, 2H), 4.13 (s, 2H), 2.34 (q, J=6.5 Hz, 1H), 2.22 (s, 3H), 2.17 (q, J=7.5 Hz, 2H), 1.48 (s, 6H), 1.09 (t, J=7.5 Hz, 3H), 0.25 (d, J=6.5 Hz, 3H).

$^{13}$C-NMR (125 MHz, CDCl$_3$, δ): 98.6, 90.3, 78.4, 76.6, 76.0, 46.9, 43.7, 24.1, 21.2, 21.1, 21.0, 15.1.

Example 54

[Chem. 42]

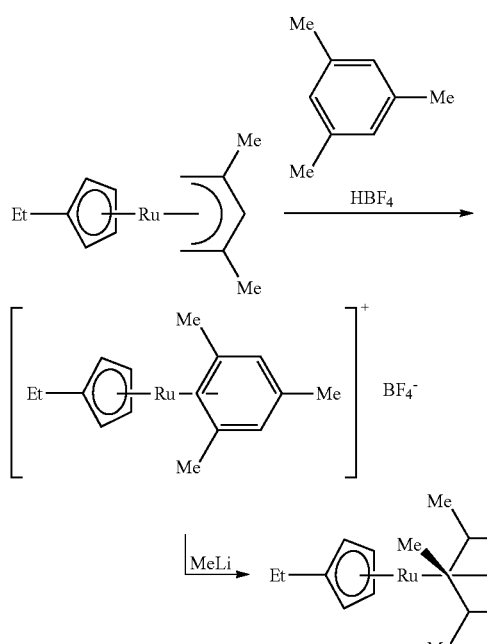

In an argon atmosphere, 20.0 g (166 mmol) of 1,3,5-trimethylbenzene was added to a solution prepared by dissolving 38.7 g (134 mmol) of ($\eta^5$-2,4-dimethyl-2,4-pentadienyl)($\eta^5$-ethylcyclopentadienyl)ruthenium (Ru($\eta^5$-C$_5$EtH$_4$)($\eta^5$-CH$_2$C(Me)CHC(Me)CH$_2$)) that was synthesized according to the method described in JP-A-2003-342286, in 200 mL of tetrahydrofuran. To this solution, 25 mL (42%, 165 mmol) of an aqueous tetrahydrofluoroboric acid solution was added at −78° C., and the mixture was stirred at room temperature for 3 days. At this point, a part of the reaction mixture was sampled and analyzed using $^1$H-NMR, as a result, it was confirmed that [Ru($\eta^5$-C$_5$EtH$_4$)($\eta^6$-C$_6$Me$_3$H$_3$)][BF$_4$] was produced. The solvent was removed from the reaction mixture by distillation under reduced pressure, and the residue was washed with 100 mL of hexane and dissolved in 150 mL of tetrahydrofuran. Subsequently, 90 mL (1.10 mol/L, 99.0 mmol) of a diethyl ether solution of methyllithium was added thereto at −78° C. and the mixture was stirred at room temperature for 20 hours. After removing the solvent from the reaction mixture by distillation under reduced pressure, 250 mL of hexane was added to the residue and the mixture was vigorously stirred at room temperature. The produced suspension was filtered, and the solvent was removed from the filtrate by distillation under reduced pressure. The remaining liquid was purified using column chromatography (alumina, hexane) and then distilled under reduced pressure (distillation temperature: 97° C./back pressure: 29 Pa) to obtain ($\eta^5$-ethylcyclopentadienyl)($\eta^5$-1,3,5,6-exo-tetramethylcyclohexadienyl)ruthenium (Ru($\eta^5$-C$_5$EtH$_4$)($\eta^5$-C$_6$H$_3$Me$_4$)) as a yellow liquid (20.0 g, yield: 61%). The obtained Ru($\eta^5$-C$_5$EtH$_4$)($\eta^5$-C$_6$H$_3$Me$_4$) was measured for $^1$H and $^{13}$C-NMR spectra, as a result, these spectra agreed with the spectra obtained in Example 53.

Production Example of Ruthenium-Containing Thin Film Using Ammonia as Reaction Gas Examples 55 to 57

Ruthenium-containing thin films were produced by the thermal CVD method using the ruthenium complex (3a) of the present invention for the material. The apparatus used for the thin film production is sketched in FIG. 1. The deposition conditions are as shown in Table 12, and other conditions are as follows.

Total pressure in material container: 13.3 kPa, flow rate of carrier gas: 30 sccm, material feed rate: 0.012 sccm, flow rate of ammonia: 100 sccm, flow rate of diluent gas: 70 sccm, substrate: SiO$_2$/Si, and deposition time: 1 hour. As the carrier gas and diluent gas, argon was used. Here, the material feed rate to the reaction chamber can be determined based on the calculation formula: (flow rate of carrier gas×vapor pressure of material÷total pressure in material container).

In all of Examples 55 to 57, when the produced thin film was confirmed by X-ray fluorescence analysis, a characteristic X-ray based on ruthenium was detected. The film thickness computed from the intensity of X-ray detected is shown in Table 12.

[Table 26]

TABLE 12

| | A | B | C | D | E |
|---|---|---|---|---|---|
| Example 55 | 3-3 (Example 50) | 68 | 5.3 | 500 | 8 |
| Example 56 | 3-3 (Example 50) | 68 | 5.3 | 450 | 3 |
| Example 57 | 3-46 (Example 54) | 67 | 5.3 | 500 | 2 |

A: Material, B: material container temperature [° C.], C: vapor pressure of material [Pa], D: substrate temperature [° C.], E: film thickness [nm].

Production Example of Ruthenium-Containing Thin Film Using Oxygen as Reaction Gas Examples 58 to 65

Ruthenium-containing thin films were produced by the thermal CVD method using the ruthenium complex (3a) for the material. The apparatus used for the thin film production is sketched in FIG. 1. The deposition conditions are as shown in Table 13, and other conditions are as follows.

Total pressure in material container: 13.3 kPa, flow rate of carrier gas: 30 sccm, material feed rate: 0.012 sccm, flow rate of oxygen: 0.16 sccm, flow rate of diluent gas: 169 sccm, substrate: $SiO_2$/Si, and deposition time: 1 hour. As the carrier gas and diluent gas, argon was used. In all of Examples 13 to 20, when the produced thin film was confirmed by X-ray fluorescence analysis, a characteristic X-ray based on ruthenium was detected. The film thickness computed from the intensity of X-ray detected is shown in Table 13.

[Table 27]

TABLE 13

|  | A | B | C | D | E |
| --- | --- | --- | --- | --- | --- |
| Example 58 | 3-3 (Example 50) | 68 | 5.3 | 400 | 3 |
| Example 59 | 3-3 (Example 50) | 68 | 5.3 | 300 | 2 |
| Example 60 | 3-3 (Example 50) | 68 | 5.3 | 250 | 37 |
| Example 61 | 3-3 (Example 50) | 68 | 5.3 | 225 | 19 |
| Example 62 | 3-46 (Example 54) | 67 | 5.3 | 400 | 1 |
| Example 63 | 3-46 (Example 54) | 67 | 5.3 | 300 | 46 |
| Example 64 | 3-46 (Example 54) | 67 | 5.3 | 250 | 32 |
| Example 65 | 3-46 (Example 54) | 67 | 5.3 | 225 | 7 |

A: Material, B: material container temperature [° C.], C: vapor pressure of material [Pa], D: substrate temperature [° C.], E: film thickness [nm].

The followings can be understood from these Examples. That is, as seen from Examples 55 to 57, the ruthenium complex (3a) is a material capable of producing a ruthenium-containing thin film even without using an oxidizing gas. In addition as seen from Examples 58 to 65, the ruthenium complex (3a) can produce a ruthenium-containing thin film also when an oxidizing gas is used.

Evaluation Example 1

A ruthenium-containing thin film was produced by the thermal CVD method using the ruthenium complex (1) obtained in Example 9. The apparatus used for the thin film production is sketched in FIG. 1. The deposition conditions are as follows.

Material container temperature: 64° C., vapor pressure of material: 5.3 Pa, total pressure in material container: 6.7 kPa, substrate temperature: 400° C., flow rate of carrier gas: 30 sccm, material feed rate: 0.024 sccm, flow rate of ammonia: 100 sccm, flow rate of diluent gas: 70 sccm, hole substrate: $SiO_2$/Si (hole diameter: 400 nm, hole depth: 1,000 nm), and deposition time: 5 hours. Argon was used as the carrier gas.

Figure 9:
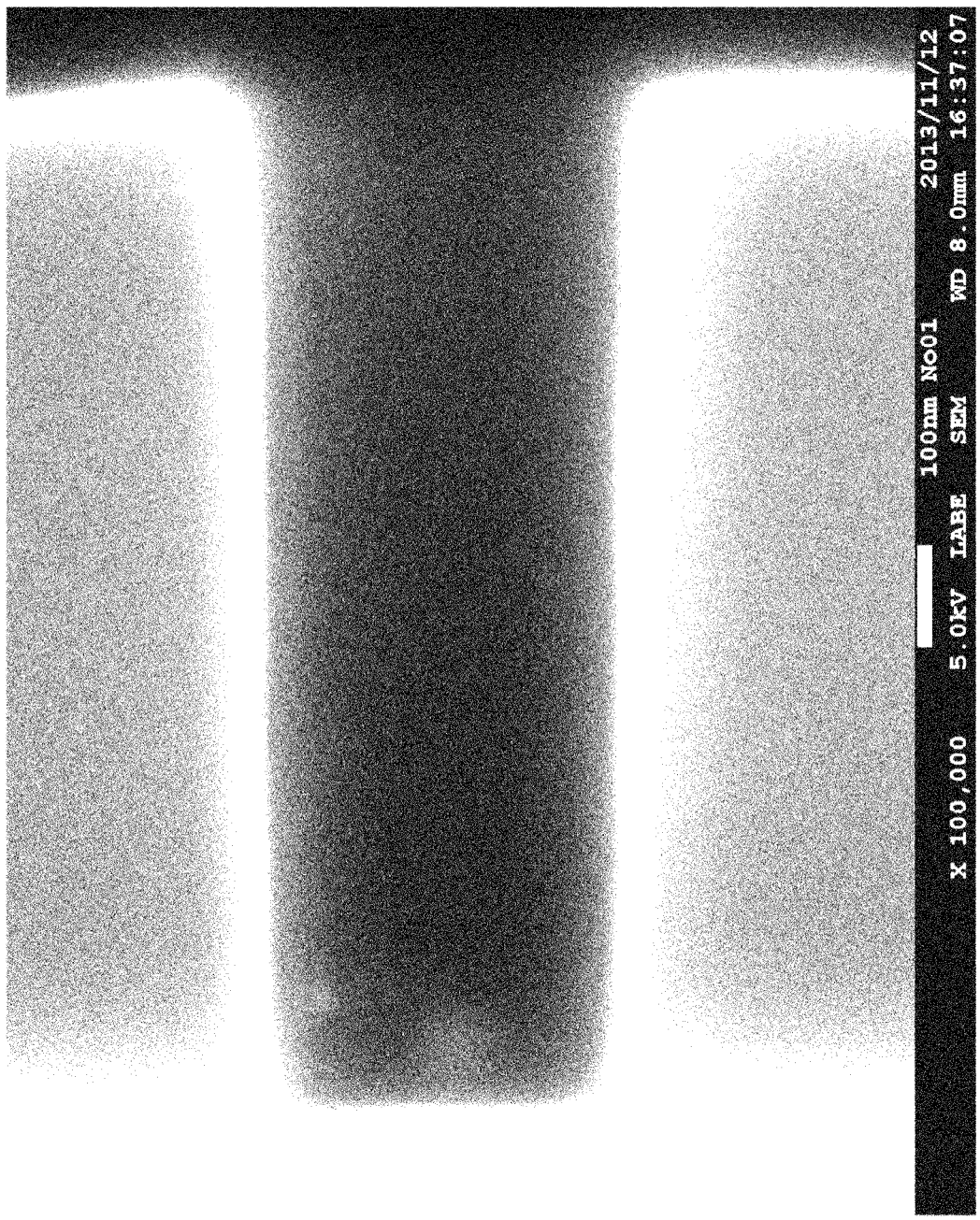
FIG. 9 is a view showing a cross-sectional FE-SEM image of the film obtained in Evaluation Example 1.

The produced thin film was confirmed by X-ray fluorescence analysis, as a result, a characteristic X-ray based on ruthenium was detected. The film thickness was computed from the intensity of X-ray detected and found to be 8 nm. The electrical properties of the ruthenium-containing thin film produced were measured by the four probe method, and the resistivity was found to be 123 µΩ·cm. When the cross-section of the film was observed by FE-SEM (field-emission scanning electron microscope), the film thickness was the same between the hole opening and the hole bottom (FIG. 9). As FE-SEM, JSM-7600F manufactured by JEOL Ltd. was used. The measurement conditions were acceleration voltage: 5 kV, observation magnitude: 100,000 times, and sample pretreatment: cutting of sample→resin embedding→ion milling processing of cross-section.

Evaluation Example 2

A ruthenium-containing thin film was produced by the thermal CVD method using the ruthenium complex (1) obtained in Example 9. The apparatus used for the thin film production is sketched in FIG. 1. The deposition conditions are as follows.

Material container temperature: 64° C., vapor pressure of material: 5.3 Pa, total pressure in material container: 6.7 kPa, substrate temperature: 400° C., flow rate of carrier gas: 30 sccm, material feed rate: 0.024 sccm, flow rate of ammonia: 50 sccm, flow rate of diluent gas: 20 sccm, hole substrate: $SiO_2$/Si (hole diameter: 400 nm, hole depth: 800 nm), and deposition time: 5 hours. Argon was used as the carrier gas.

Figure 10:
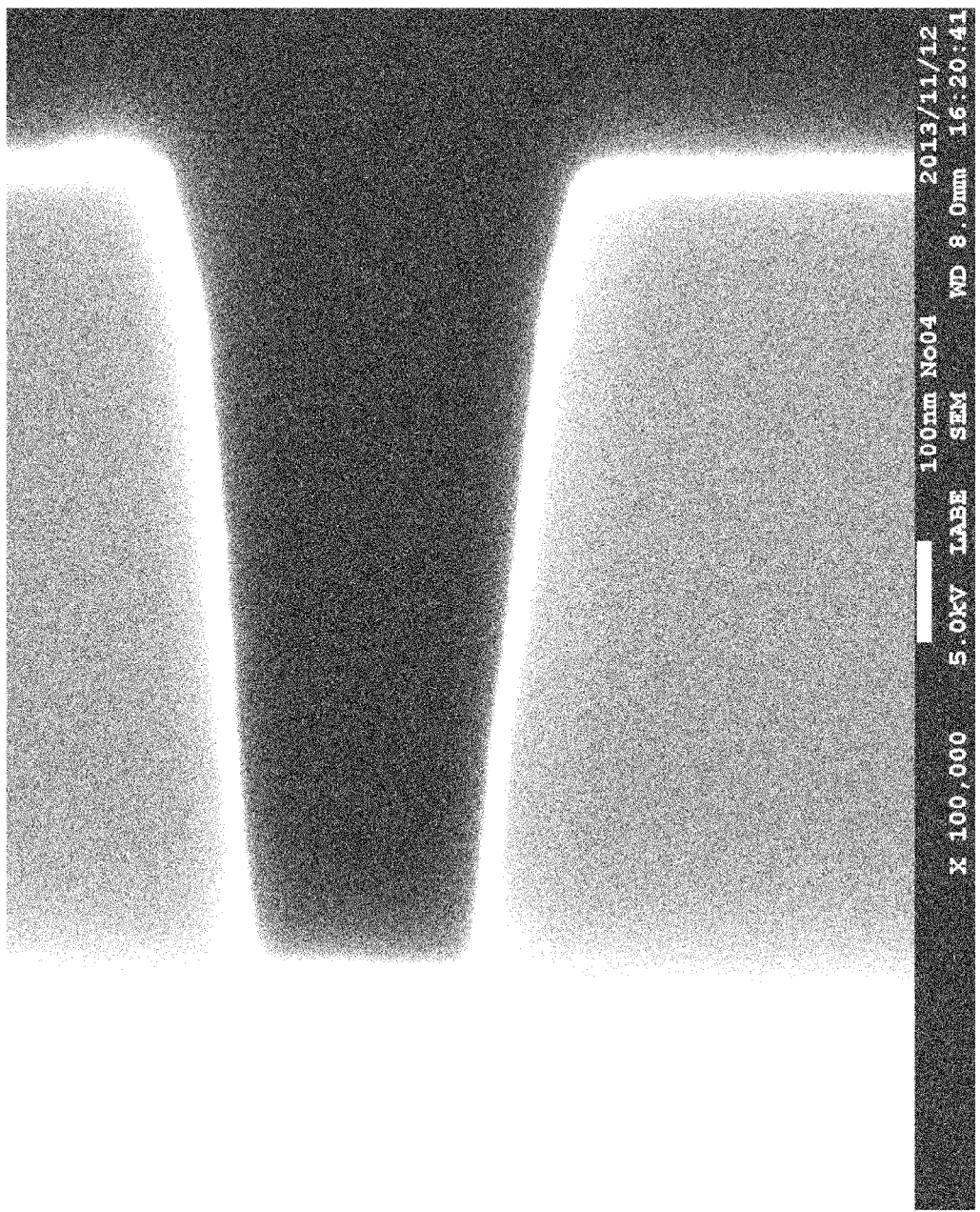
FIG. 10 is a view showing a cross-sectional FE-SEM image of the film obtained in Evaluation Example 2.

The produced thin film was confirmed by X-ray fluorescence analysis, as a result, a characteristic X-ray based on ruthenium was detected. The film thickness was computed from the intensity of X-ray detected and found to be 7 nm. The electrical properties of the ruthenium-containing thin film produced were measured by the four probe method, and the resistivity was found to be 712 µΩ·cm. When the cross-section of the film was observed by FE-SEM, the film thickness was the same between the hole opening and the hole bottom (FIG. 10). It is understood from Evaluation Examples 1 and 2 that the ruthenium complex of the present invention can produce a uniform film on an uneven surface at a low temperature of 400° C. or less even without using an oxidizing gas.

While the invention has been described in detail and with reference to specific embodiments thereof, it will be apparent to one skilled in the art that various changes and modifications can be made therein without departing from the spirit and scope of the invention.

This application is based on Japanese Patent Application (Patent Application No. 2012-268396) filed on Dec. 7, 2012, Japanese Patent Application (Patent Application No. 2013-133480) filed on Jun. 26, 2013, and Japanese Patent Application (Patent Application No. 2013-156294) filed on Jul. 29, 2013, the entirety of which is incorporated herein by way of reference. All references cited herein are incorporated in their entirety.

INDUSTRIAL APPLICABILITY

The novel ruthenium complex of the present invention is useful for the production of a ruthenium-containing thin film.

EXPLANATIONS OF REFERENCE SIGNS

1 denotes a material container.
2 denotes a constant-temperature bath.
3 denotes a reaction chamber.
4 denotes a substrate.
5 denotes reaction gas.
6 denotes diluent gas.
7 denotes carrier gas.
8 denotes a mass flow controller.
9 denotes a mass flow controller.
10 denotes a mass flow controller.
11 denotes an oil rotary pump.
12 denotes an exhaust.

The invention claimed is:

1. A ruthenium complex represented by formula (A):

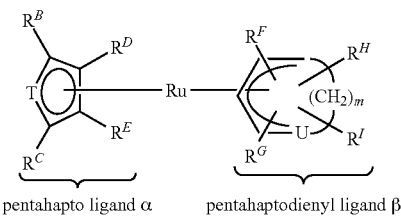

pentahapto ligand α   pentahaptodienyl ligand β wherein T represents $CR^A$ or a nitrogen atom; U represents an oxygen atom or CH; each of $R^A$, $R^B$, $R^C$, $R^D$, $R^E$, $R^F$, $R^G$, $R^H$ and $R^I$ independently represents a hydrogen atom or an alkyl group having a carbon number of 1 to 6; m represents any one integer of 0, 1 and 3; and the pentahaptodienyl ligand β has a cyclic structure when m is 1 or 3, and has a non-cyclic structure when m is 0, provided that when m is 0, T is $CR^A$, U is an oxygen atom, $R^F$ and $R^G$ are an alkyl group having a carbon number of 1 to 6, and $R^H$ and $R^I$ are a hydrogen atom, excluding a case where all of $R^A$, $R^B$, $R^C$, $R^D$ and $R^E$ are a methyl group at the same time, that when m is 1, T is $CR^A$, U is CH and $R^I$ is an alkyl group having a carbon number of 1 to 6, excluding a case where all of $R^F$, $R^G$ and $R^H$ are a hydrogen atom at the same time and all of $R^A$, $R^B$, $R^C$, $R^D$, $R^E$ and $R^I$ are a methyl group at the same time, and that when m is 3, T is a nitrogen atom, U is CH, $R^B$ and $R^C$ are an alkyl group having a carbon number of 1 to 6, $R^D$, $R^E$, $R^F$ and $R^G$ are a hydrogen atom, and $R^H$ and $R^I$ are a hydrogen atom or a methyl group.

2. The ruthenium complex according to claim 1, which is represented by formula (1a):

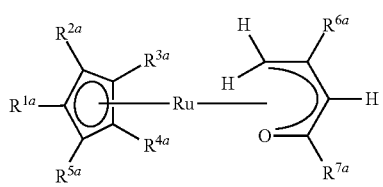

wherein each of $R^{1a}$, $R^{2a}$, $R^{3a}$, $R^{4a}$ and $R^{5a}$ independently represents a hydrogen atom or an alkyl group having a carbon number of 1 to 6, excluding a case where all of $R^{1a}$, $R^{2a}$, $R^{3a}$, $R^{4a}$ and $R^{5a}$ are a methyl group at the same time; and each of $R^{6a}$ and $R^{7a}$ independently represents an alkyl group having a carbon number of 1 to 6.

3. The ruthenium complex according to claim 2, wherein $R^{1a}$ is an alkyl group having a carbon number of 1 to 6; $R^{2a}$, $R^{3a}$, $R^{4a}$ and $R^{5a}$ are a hydrogen atom; and $R^{6a}$ and $R^{7a}$ are a methyl group.

4. The ruthenium complex according to claim 2, wherein $R^{1a}$ is a methyl group or an ethyl group; $R^{2a}$, $R^{3a}$, $R^{4a}$ and $R^{5a}$ are a hydrogen atom; and $R^{6a}$ and $R^{7a}$ are a methyl group.

5. The ruthenium complex according to claim 1, which is represented by formula (2):

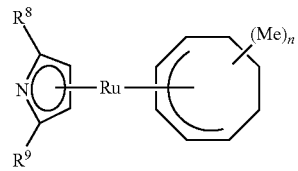

wherein each of $R^8$ and $R^9$ independently represents an alkyl group having a carbon number of 1 to 6; and n represents an integer of 0 to 2.

6. The ruthenium complex according to claim 5, wherein n is 0.

7. The ruthenium complex according to claim 5, wherein $R^8$ and $R^9$ are a methyl group.

8. The ruthenium complex according to claim 1, which is represented by formula (3):

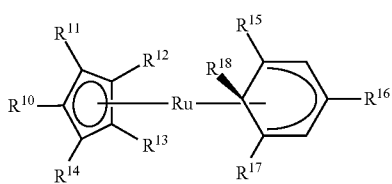

wherein each of $R^{10}$, $R^{11}$, $R^{12}$, $R^{13}$, $R^{14}$, $R^{15}$, $R^{16}$ and $R^{17}$ independently represents a hydrogen atom or an alkyl group having a carbon number of 1 to 6; and $R^{18}$ represents an alkyl group having a carbon number of 1 to 6, excluding a case where all of $R^{15}$, $R^{16}$ and $R^{17}$ are a hydrogen atom at the same time and all of $R^{10}$, $R^{11}$, $R^{12}$, $R^{13}$, $R^{14}$ and $R^{18}$ are a methyl group at the same time.

9. The ruthenium complex according to claim 8, wherein $R^{10}$ is an alkyl group having a carbon number of 1 to 6; $R^{11}$, $R^{12}$, $R^{13}$ and $R^{14}$ are a hydrogen atom; all of $R^{15}$, $R^{16}$ and $R^{17}$ are a hydrogen atom or a methyl group at the same time; and $R^{18}$ is a methyl group.

10. The ruthenium complex according to claim 8, wherein $R^{10}$ is an ethyl group; $R^{11}$, $R^{12}$, $R^{13}$ and $R^{14}$ are a hydrogen atom; all of $R^{15}$, $R^{16}$ and $R^{17}$ are a hydrogen atom or a methyl group at the same time; and $R^{18}$ is a methyl group.

11. A method for producing a ruthenium complex, comprising:
reacting a cationic tris(nitrile) complex represented by formula (4):

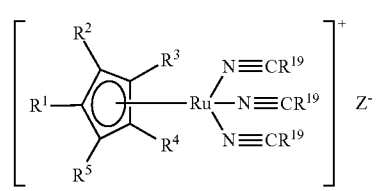

wherein each of $R^1$, $R^2$, $R^3$, $R^4$ and $R^5$ independently represents a hydrogen atom or an alkyl group having a carbon number of 1 to 6; $R^{19}$ represents an alkyl group having a carbon number of 1 to 4; and $Z^-$ represents a counter anion, with an enone derivative represented by formula (5):

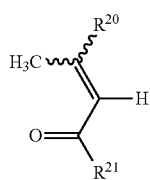
(5)

wherein each of $R^{20}$ and $R^{21}$ independently represents an alkyl group having a carbon number of 1 to 6, in the presence of a base to produce a ruthenium complex represented by formula (1):

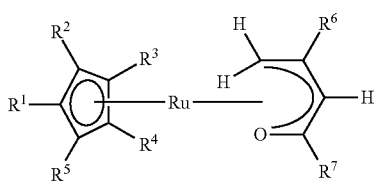
(1)

wherein each of $R^1$, $R^2$, $R^3$, $R^4$ and $R^5$ independently represents a hydrogen atom or an alkyl group having a carbon number of 1 to 6; and each of $R^6$ and $R^7$ independently represents an alkyl group having a carbon number of 1 to 6.

12. The method for producing a ruthenium complex according to claim 11,
wherein $R^1$ is an alkyl group having a carbon number of 1 to 6; $R^2$, $R^3$, $R^4$ and $R^5$ are a hydrogen atom; and $R^6$ and $R^7$ are a methyl group.

13. The method for producing a ruthenium complex according to claim 11,
wherein $R^1$ is a methyl group or an ethyl group; $R^2$, $R^3$, $R^4$ and $R^5$ are a hydrogen atom; and $R^6$ and $R^7$ are a methyl group.

14. The method for producing a ruthenium complex according to claim 11,
wherein the base is an alkali metal carboxylate or an alkylamine.

15. A cationic tris(nitrile) complex represented by formula (4b):

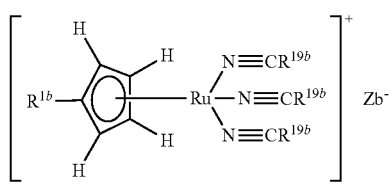
(4b)

wherein $R^{1b}$ represents an alkyl group having a carbon number of 2 to 6; $R^{19b}$ represents an alkyl group having a carbon number of 1 to 4; and $Zb^-$ represents a counter anion.

16. The cationic tris(nitrile) complex according to claim 15,
wherein $R^{19b}$ is a methyl group.

17. The cationic tris(nitrile) complex according to claim 15,
wherein $R^{1b}$ is an ethyl group; and $R^{19b}$ is a methyl group.

18. A method for producing a cationic tris(nitrile) complex, comprising:
reacting a ruthenocene derivative represented by formula (6):

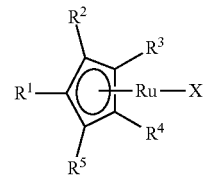
(6)

wherein each of $R^1$, $R^2$, $R^3$, $R^4$ and $R^5$ independently represents a hydrogen atom or an alkyl group having a carbon number of 1 to 6; and X represents an $\eta^5$-(unsubstituted or substituted)cyclopentadienyl ligand represented by formula (7):

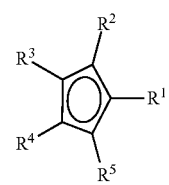
(7)

wherein $R^1$, $R^2$, $R^3$, $R^4$ and $R^5$ have the same meanings as above, or an $\eta^5$-2,4-dimethyl-2,4-pentadienyl ligand,
a nitrile represented by the formula: $R^{19}CN$ wherein $R^{19}$ represents an alkyl group having a carbon number of 1 to 4, and
a protonic acid represented by the formula: $H^+Z^-$ wherein $Z^-$ represents a counter anion, to produce a cationic tris(nitrile) complex represented by formula (4):

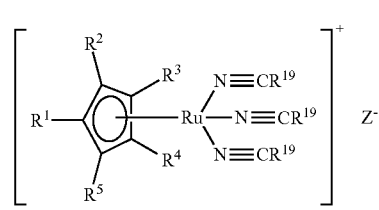
(4)

wherein $R^1$, $R^2$, $R^3$, $R^4$, $R^5$, $R^{19}$ and $Z^-$ have the same meanings as above.

19. The method for producing a cationic tris(nitrile) complex according to claim 18,
wherein X is an $\eta^5$-(unsubstituted or substituted)cyclopentadienyl ligand represented by formula (7):

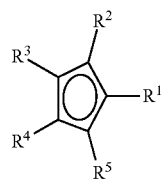

(7)

wherein each of $R^1$, $R^2$, $R^3$, $R^4$ and $R^5$ independently represents a hydrogen atom or an alkyl group having a carbon number of 1 to 6.

20. The method for producing a cationic tris(nitrile) complex according to claim 18,
wherein $R^{19}$ is a methyl group.

21. A method for producing a ruthenium complex, comprising:
reacting a ruthenocene derivative represented by formula (6):

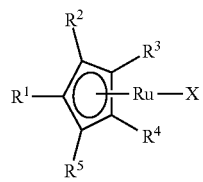

(6)

wherein each of $R^1$, $R^2$, $R^3$, $R^4$ and $R^5$ independently represents a hydrogen atom or an alkyl group having a carbon number of 1 to 6; and X represents an $\eta^5$-(unsubstituted or substituted)cyclopentadienyl ligand represented by formula (7):

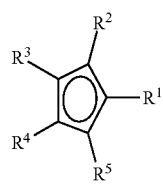

(7)

wherein $R^1$, $R^2$, $R^3$, $R^4$ and $R^5$ have the same meanings as above, or an $\eta^5$-2,4-dimethyl-2,4-pentadienyl ligand,
a nitrile represented by the formula: $R^{19}CN$ wherein $R^{19}$ represents an alkyl group having a carbon number of 1 to 4, and
a protonic acid represented by the formula: $H^+Z^-$ wherein $Z^-$ represents a counter anion, to produce a cationic tris(nitrile) complex represented by formula (4):

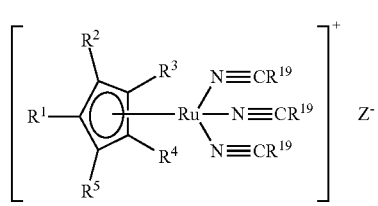

(4)

wherein $R^1$, $R^2$, $R^3$, $R^4$, $R^5$, $R^{19}$ and $Z^-$ have the same meanings as above; and
further reacting the cationic tris(nitrile) complex with an enone derivative represented by formula (5):

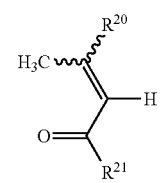

(5)

wherein each of $R^{20}$ and $R^{21}$ independently represents an alkyl group having a carbon number of 1 to 6, in the presence of a base to produce a ruthenium complex represented by formula (1):

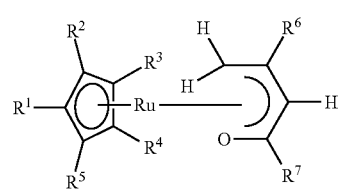

(1)

wherein $R^1$, $R^2$, $R^3$, $R^4$, $R^5$, $R^6$ and $R^7$ have the same meanings as above.

22. The method for producing a ruthenium complex according to claim 21,
wherein X is an $\eta^5$-(unsubstituted or substituted)cyclopentadienyl ligand represented by formula (7):

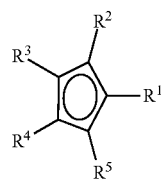

(7)

wherein each of $R^1$, $R^2$, $R^3$, $R^4$ and $R^5$ independently represents a hydrogen atom or an alkyl group having a carbon number of 1 to 6.

23. The method for producing a ruthenium complex according to claim 21,
wherein $R^{19}$ is a methyl group.

24. A method for producing the ruthenium complex according to claim 5, comprising:
reacting a cationic bis(cyclooctadienyl) complex represented by formula (8):

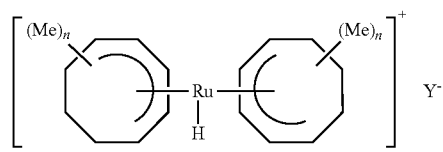

(8)

wherein n represents an integer of 0 to 2; and $Y^-$ represents a counter anion, with a substituted pyrrole represented by formula (9):

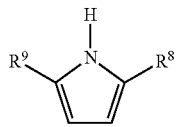
(9)

wherein each of $R^8$ and $R^9$ independently represents an alkyl group having a carbon number of 1 to 6, in the presence of a base.

25. The method for producing a ruthenium complex according to claim 24,
wherein the base is an organic base.

26. A method for producing the ruthenium complex according to claim 8, comprising:
reacting a cationic arene complex represented by formula (10):

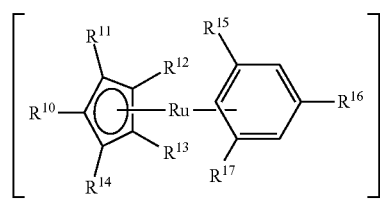
(10)

wherein $R^{10}$ to $R^{17}$ have the same meanings as $R^{10}$ to $R^{17}$ of formula (3); and $P^-$ represents a counter anion, with an alkyllithium represented by formula (11): $R^{18}Li$ wherein $R^{18}$ has the same meaning as $R^{18}$ of formula (3).

27. A method for producing a ruthenium-containing thin film, comprising:
vaporizing a ruthenium complex represented by formula (1):

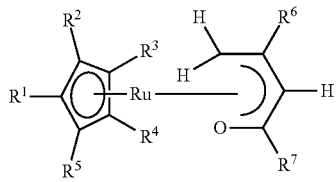
(1)

wherein each of $R^1$, $R^2$, $R^3$, $R^4$ and $R^5$ independently represents a hydrogen atom or an alkyl group having a carbon number of 1 to 6; and each of $R^6$ and $R^7$ independently represents an alkyl group having a carbon number of 1 to 6; and
decomposing the ruthenium complex on a substrate.

28. A method for producing a ruthenium-containing thin film, comprising:
vaporizing the ruthenium complex according to claim 5; and
decomposing the ruthenium complex on a substrate.

29. A method for producing a ruthenium-containing thin film, comprising:
vaporizing a ruthenium complex represented by formula (3a):

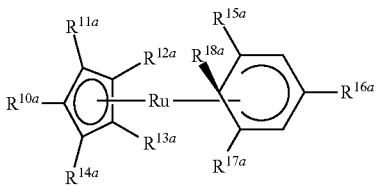
(3a)

wherein each of $R^{10a}$, $R^{11a}$, $R^{12a}$, $R^{13a}$, $R^{14a}$, $R^{15a}$, $R^{16a}$ and $R^{17a}$ independently represents a hydrogen atom or an alkyl group having a carbon number of 1 to 6; and $R^{18a}$ represents an alkyl group having a carbon number of 1 to 6; and
decomposing the ruthenium complex on a substrate.

* * * * *